(12) United States Patent
Lefebvre et al.

(10) Patent No.: US 9,518,899 B2
(45) Date of Patent: Dec. 13, 2016

(54) AUTOMATED REAGENT DISPENSING SYSTEM AND METHOD OF OPERATION

(75) Inventors: Gilles Lefebvre, San Clemente, CA (US); Patrick P. Jennings, Lomita, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 1075 days.

(21) Appl. No.: 11/349,663

(22) Filed: Feb. 7, 2006

(65) Prior Publication Data

US 2006/0173575 A1 Aug. 3, 2006

Related U.S. Application Data

(63) Continuation-in-part of application No. 10/639,021, filed on Aug. 11, 2003, now Pat. No. 7,501,283.

(Continued)

(51) Int. Cl.
*G06F 17/00* (2006.01)
*G01N 1/31* (2006.01)
(Continued)

(52) U.S. Cl.
CPC ............... *G01N 1/31* (2013.01); *G01N 1/312* (2013.01); *G01N 35/0092* (2013.01);
(Continued)

(58) Field of Classification Search
CPC .... G01N 1/31; G01N 1/312; G01N 35/00584; G01N 35/0092; G01N 35/1002; G01N 2035/00881
(Continued)

(56) References Cited

U.S. PATENT DOCUMENTS 1,621,097 A 3/1927 Zammataro
2,709,025 A 5/1955 Scott
(Continued)

FOREIGN PATENT DOCUMENTS

AU 2004266226 3/2005
CN 2390207 Y 8/2000
(Continued)

OTHER PUBLICATIONS

PCT Search Report for PCT Appln No. PCT/US04/25960, mailed Aug. 8, 2006 (10 pages).
(Continued)

*Primary Examiner* — Brian R Gordon
(74) *Attorney, Agent, or Firm* — Blakely Sokoloff Taylor & Zafman LLP

(57) ABSTRACT

A system and method that enables automated reagent dispensing for tissue stainers. The stainers receive staining protocols from a central controller. The central controller may control a plurality of stainers simultaneously. The stainers obtain information provided on slide identifiers which is communicated to the central controller. The central controller determines a particular staining protocol to apply to a particular slide. The staining protocol is downloaded to the stainer which enables the stainer to operate without additional communication with the central controller. A user may manually initiate a staining protocol or the central controller may operate the stainers on a scheduled basis.

20 Claims, 53 Drawing Sheets

Related U.S. Application Data

(60) Provisional application No. 60/652,432, filed on Feb. 11, 2005, provisional application No. 60/678,682, filed on May 6, 2005.

(51) Int. Cl.
*G01N 35/00* (2006.01)
*G01N 35/10* (2006.01)

(52) U.S. Cl.
CPC ... *G01N 35/00584* (2013.01); *G01N 35/1002* (2013.01); *G01N 2035/0093* (2013.01); *G01N 2035/00881* (2013.01)

(58) Field of Classification Search
USPC ............... 422/100, 68.1, 500–501, 509, 517, 521,422/536; 436/43, 46, 174, 180; 700/236, 242, 700/244–245, 265–266, 285

See application file for complete search history.

(56) References Cited

U.S. PATENT DOCUMENTS

| | | | |
|---|---|---|---|
| 2,772,817 A | 12/1956 | Jauch | |
| 3,008,611 A | 11/1961 | Mancusi, Jr. | |
| 3,066,832 A | 12/1962 | Rossetti | |
| 3,116,747 A | 1/1964 | Cowles et al. | |
| 3,232,496 A | 2/1966 | Rockwell, Jr. et al. | |
| 3,294,290 A | 12/1966 | Erickson et al. | |
| 3,504,699 A | 4/1970 | Grise | |
| 3,741,439 A | 6/1973 | Vehrs | |
| 3,752,366 A | 8/1973 | Lawrence, Jr. | |
| 3,794,213 A | 2/1974 | Schwartzman | |
| 3,870,201 A | 3/1975 | Asplund | |
| 3,881,641 A | 5/1975 | Pliml, Jr. et al. | |
| 3,904,079 A | 9/1975 | Kross | |
| 3,987,938 A | 10/1976 | Cooprider et al. | |
| 4,018,363 A | 4/1977 | Cassia | |
| 4,025,241 A | 5/1977 | Clemens | |
| 4,039,775 A | 8/1977 | Andra | |
| 4,067,414 A | 1/1978 | Funke | |
| 4,099,483 A | 7/1978 | Henderson | |
| 4,130,224 A | 12/1978 | Norman et al. | |
| 4,134,853 A | 1/1979 | Ehrlich et al. | |
| 4,135,649 A | 1/1979 | Baldwin et al. | |
| 4,149,573 A | 4/1979 | Cassia | |
| 4,149,633 A | 4/1979 | Nilson | |
| 4,199,558 A | 4/1980 | Henderson | |
| 4,256,242 A | 3/1981 | Christine | |
| 4,258,759 A | 3/1981 | Achen | |
| 4,334,640 A | 6/1982 | van Overbruggen et al. | |
| 4,345,627 A | 8/1982 | Cassia | |
| 4,349,133 A | 9/1982 | Christine | |
| 4,356,727 A | 11/1982 | Brown et al. | |
| 4,394,938 A | 7/1983 | Frassanito | |
| 4,440,323 A | 4/1984 | Benson | |
| 4,513,885 A | 4/1985 | Hogan | |
| 4,515,294 A | 5/1985 | Udall | |
| 4,561,571 A | 12/1985 | Chen | |
| 4,573,612 A | 3/1986 | Maddison et al. | |
| 4,601,411 A | 7/1986 | van Overbruggen | |
| 4,604,964 A | 8/1986 | Gordon et al. | |
| 4,607,764 A | 8/1986 | Christine | |
| 4,615,476 A | 10/1986 | Hobbs et al. | |
| 4,621,749 A | 11/1986 | Kanfer | |
| 4,646,945 A | 3/1987 | Steiner et al. | |
| 4,651,898 A | 3/1987 | Bell | |
| 4,667,854 A | 5/1987 | McDermott et al. | |
| 4,673,109 A | 6/1987 | Cassia | |
| 4,678,752 A | 7/1987 | Thorne et al. | |
| 4,722,372 A | 2/1988 | Hoffman et al. | |
| 4,731,335 A | 3/1988 | Brigati | |
| 4,741,461 A | 5/1988 | Williamson et al. | |
| 4,741,898 A | 5/1988 | Mallik et al. | |
| 4,764,342 A | 8/1988 | Kelln et al. | |
| 4,776,495 A | 10/1988 | Vignot | |
| 4,790,640 A | 12/1988 | Nason | |
| 4,798,311 A | 1/1989 | Workum | |
| 4,801,431 A | 1/1989 | Cuomo et al. | |
| 4,834,019 A | 5/1989 | Gordon et al. | |
| 4,838,457 A | 6/1989 | Swahl et al. | |
| 4,846,636 A | 7/1989 | Danby et al. | |
| 4,849,176 A * | 7/1989 | Sakagami | G01N 35/0095 422/64 |
| 4,867,347 A | 9/1989 | Wass et al. | |
| 4,880,149 A | 11/1989 | Scholefield et al. | |
| 4,886,192 A | 12/1989 | Cassia | |
| 4,895,276 A | 1/1990 | Maldonado | |
| 4,917,265 A | 4/1990 | Chiang | |
| 4,921,136 A | 5/1990 | Roggenburg, Jr. | |
| 4,927,061 A | 5/1990 | Leigh et al. | |
| 4,932,624 A | 6/1990 | Holm | |
| 4,946,076 A | 8/1990 | Hackmann et al. | |
| 4,955,512 A | 9/1990 | Sharples | |
| 4,961,508 A | 10/1990 | Weimer et al. | |
| 4,967,940 A | 11/1990 | Blette et al. | |
| 4,969,581 A | 11/1990 | Seifert et al. | |
| 4,972,978 A | 11/1990 | DeLuca | |
| 4,974,754 A | 12/1990 | Wirz | |
| 4,978,036 A | 12/1990 | Burd | |
| 4,978,502 A | 12/1990 | Dole et al. | |
| 4,985,206 A | 1/1991 | Bowman et al. | |
| 5,002,736 A | 3/1991 | Babbitt et al. | |
| 5,033,656 A | 7/1991 | Blette et al. | |
| 5,033,943 A | 7/1991 | Durrum et al. | |
| 5,035,350 A | 7/1991 | Blette et al. | |
| 5,042,691 A | 8/1991 | Maldonado | |
| 5,068,091 A | 11/1991 | Toya | |
| 5,073,504 A | 12/1991 | Bogen | |
| 5,082,150 A | 1/1992 | Steiner et al. | |
| 5,105,992 A | 4/1992 | Fender et al. | |
| 5,225,325 A | 7/1993 | Miller et al. | |
| 5,232,664 A | 8/1993 | Krawzak et al. | |
| 5,242,081 A | 9/1993 | van der Heyden et al. | |
| 5,242,083 A | 9/1993 | Christine et al. | |
| 5,244,787 A | 9/1993 | Key et al. | |
| 5,252,293 A | 10/1993 | Drbal et al. | |
| 5,253,774 A | 10/1993 | Honig et al. | |
| 5,255,822 A | 10/1993 | Mease et al. | |
| 5,265,770 A | 11/1993 | Matkovich et al. | |
| 5,273,905 A | 12/1993 | Muller et al. | |
| 5,275,309 A | 1/1994 | Baron et al. | |
| 5,316,452 A | 5/1994 | Bogen et al. | |
| 5,322,771 A | 6/1994 | Rybski et al. | |
| 5,338,358 A | 8/1994 | Mizusawa et al. | |
| 5,355,439 A | 10/1994 | Bernstein et al. | |
| 5,356,039 A | 10/1994 | Christine et al. | |
| 5,390,822 A | 2/1995 | Lataix | |
| 5,405,580 A | 4/1995 | Palmer | |
| 5,418,138 A | 5/1995 | Miller et al. | |
| 5,421,489 A | 6/1995 | Holzner, Sr. et al. | |
| 5,424,036 A | 6/1995 | Ushikubo | |
| 5,425,918 A | 6/1995 | Healey et al. | |
| 5,433,351 A | 7/1995 | Okuyama et al. | |
| 5,439,645 A * | 8/1995 | Saralegui | B01F 11/0014 366/128 |
| 5,439,649 A | 8/1995 | Tseung et al. | |
| 5,464,125 A | 11/1995 | Daansen | |
| 5,474,212 A | 12/1995 | Ichikawa et al. | |
| 5,492,247 A | 2/1996 | Shu et al. | |
| 5,501,372 A | 3/1996 | Daansen | |
| 5,525,300 A | 6/1996 | Danssaert et al. | |
| 5,534,114 A | 7/1996 | Cutright et al. | |
| 5,561,556 A | 10/1996 | Weissman et al. | |
| 5,578,452 A | 11/1996 | Shi et al. | |
| 5,579,945 A | 12/1996 | Ichikawa et al. | |
| 5,580,523 A | 12/1996 | Bard | |
| 5,595,707 A | 1/1997 | Copeland et al. | |
| 5,597,093 A | 1/1997 | Lee | |
| 5,602,674 A | 2/1997 | Weissman et al. | |
| 5,609,822 A | 3/1997 | Carey et al. | |
| 5,626,262 A | 5/1997 | Fitten et al. | |
| 5,639,423 A | 6/1997 | Northrup et al. | |

(56) References Cited

U.S. PATENT DOCUMENTS

| | | |
|---|---|---|
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,675,715 A | 10/1997 | Bernstein et al. |
| 5,700,346 A | 12/1997 | Edwards |
| 5,810,204 A | 9/1998 | Devlin et al. |
| 5,819,842 A | 10/1998 | Potter et al. |
| 5,836,482 A | 11/1998 | Ophardt et al. |
| 5,839,091 A * | 11/1998 | Rhett et al. ............ 702/19 |
| 5,843,700 A | 12/1998 | Kerrod et al. |
| 5,846,396 A | 12/1998 | Zanzucchi et al. |
| 5,851,488 A | 12/1998 | Saul et al. |
| 5,855,302 A | 1/1999 | Fisscher |
| 5,857,595 A | 1/1999 | Nilson |
| 5,885,530 A * | 3/1999 | Babson et al. ............ 422/65 |
| 5,909,828 A | 6/1999 | Salisbury |
| 5,938,414 A | 8/1999 | Kayahara et al. |
| 5,947,167 A | 9/1999 | Bogen et al. |
| 5,948,359 A | 9/1999 | Kalra et al. |
| 5,950,874 A | 9/1999 | Sindoni |
| 5,950,878 A | 9/1999 | Wade et al. |
| 5,954,167 A | 9/1999 | Richardson et al. |
| 5,958,341 A | 9/1999 | Chu |
| 5,964,454 A | 10/1999 | Volpel |
| 5,965,454 A | 10/1999 | Farmilo et al. |
| 5,968,731 A * | 10/1999 | Layne et al. ............ 435/5 |
| 5,971,223 A | 10/1999 | Fisscher |
| 6,001,309 A | 12/1999 | Gamble et al. |
| 6,012,613 A | 1/2000 | Chen |
| 6,017,495 A | 1/2000 | Ljungmann |
| 6,020,995 A | 2/2000 | Dreyer et al. |
| 6,045,759 A | 4/2000 | Ford et al. |
| 6,068,162 A | 5/2000 | De Winter et al. |
| 6,076,583 A | 6/2000 | Edwards |
| 6,092,695 A | 7/2000 | Loeffler |
| 6,093,574 A * | 7/2000 | Druyor-Sanchez et al. .. 436/180 |
| 6,096,271 A | 8/2000 | Bogen et al. |
| 6,131,773 A | 10/2000 | Wade et al. |
| 6,142,343 A | 11/2000 | Wade et al. |
| 6,152,330 A | 11/2000 | Polan |
| 6,180,061 B1 | 1/2001 | Bogen et al. |
| 6,183,693 B1 | 2/2001 | Bogen et al. |
| 6,189,740 B1 | 2/2001 | Wade et al. |
| 6,192,945 B1 | 2/2001 | Ford et al. |
| 6,206,238 B1 | 3/2001 | Ophardt |
| 6,216,916 B1 | 4/2001 | Maddox et al. |
| 6,238,910 B1 | 5/2001 | Custance et al. |
| 6,244,474 B1 | 6/2001 | Loeffler |
| 6,259,956 B1 * | 7/2001 | Myers et al. ............ 700/80 |
| 6,273,298 B1 | 8/2001 | Post |
| 6,286,725 B1 | 9/2001 | Gerber |
| 6,296,809 B1 | 10/2001 | Richards et al. |
| 6,335,166 B1 | 1/2002 | Ammann et al. |
| 6,343,716 B1 | 2/2002 | Baudin et al. |
| 6,349,264 B1 | 2/2002 | Rhett et al. |
| 6,352,861 B1 * | 3/2002 | Copeland et al. ............ 436/46 |
| 6,387,326 B1 | 5/2002 | Edwards et al. |
| 6,415,961 B2 | 7/2002 | Bonningue |
| 6,416,713 B1 * | 7/2002 | Ford et al. ............ 422/63 |
| 6,451,551 B1 | 9/2002 | Zhan et al. |
| 6,472,217 B1 | 10/2002 | Richards et al. |
| 6,489,171 B1 | 12/2002 | Aghassi et al. |
| 6,495,106 B1 | 12/2002 | Kalra et al. |
| 6,516,620 B2 | 2/2003 | Lang |
| 6,534,008 B1 | 3/2003 | Angros |
| 6,540,117 B2 | 4/2003 | Powling |
| 6,541,261 B1 | 4/2003 | Bogen et al. |
| 6,543,652 B1 | 4/2003 | Kelder et al. |
| 6,544,798 B1 | 4/2003 | Christensen et al. |
| 6,553,145 B1 | 4/2003 | Kang et al. |
| 6,568,561 B2 | 5/2003 | Studer et al. |
| 6,580,056 B1 | 6/2003 | Tacha |
| 6,582,962 B1 | 6/2003 | Richards et al. |
| 6,594,537 B1 | 7/2003 | Bernstein et al. |
| 6,605,213 B1 | 8/2003 | Ammann et al. |
| 6,607,103 B2 | 8/2003 | Gerenraich et al. |
| 6,632,598 B1 | 10/2003 | Zhang et al. |
| 6,635,225 B1 | 10/2003 | Thiem et al. |
| 6,656,428 B1 | 12/2003 | Clark et al. |
| 6,673,620 B1 | 1/2004 | Loeffler et al. |
| 6,703,247 B1 | 3/2004 | Chu |
| 6,707,873 B2 | 3/2004 | Thompson et al. |
| 6,720,888 B2 | 4/2004 | Eagleson et al. |
| 6,729,502 B2 | 5/2004 | Lewis et al. |
| 6,735,531 B2 | 5/2004 | Rhett et al. |
| 6,746,851 B1 | 6/2004 | Tseung et al. |
| 6,758,360 B2 | 7/2004 | Van Giezen et al. |
| 6,783,733 B2 | 8/2004 | Bogen et al. |
| 6,805,264 B2 | 10/2004 | Houvras |
| 6,814,262 B1 | 11/2004 | Adams et al. |
| 6,827,900 B2 | 12/2004 | Thiem et al. |
| 6,827,901 B2 | 12/2004 | Copeland et al. |
| 6,855,292 B2 | 2/2005 | Angros |
| 6,855,552 B2 | 2/2005 | Towne et al. |
| 6,855,559 B1 | 2/2005 | Christensen et al. |
| 6,899,283 B2 | 5/2005 | Ohnishi et al. |
| 6,943,029 B2 | 9/2005 | Copeland et al. |
| 6,945,128 B2 | 9/2005 | Ford et al. |
| 6,991,934 B2 | 1/2006 | Walton et al. |
| 6,998,270 B2 | 2/2006 | Tseung et al. |
| 7,004,356 B1 | 2/2006 | Sayers |
| 7,007,824 B2 | 3/2006 | Danby et al. |
| 7,025,937 B2 | 4/2006 | Plank |
| 7,057,808 B2 | 6/2006 | Dooling |
| 7,070,951 B2 | 7/2006 | Zhang et al. |
| 7,083,106 B2 | 8/2006 | Albany |
| 7,118,918 B2 | 10/2006 | Copeland et al. |
| 7,156,814 B1 | 1/2007 | Williamson et al. |
| 7,165,722 B2 | 1/2007 | Shafer et al. |
| 7,169,601 B1 | 1/2007 | Northrup |
| 7,178,416 B2 | 2/2007 | Whelan et al. |
| 7,179,424 B2 | 2/2007 | Williamson, IV et al. |
| 7,187,286 B2 | 3/2007 | Morris et al. |
| 7,199,712 B2 | 4/2007 | Tafas et al. |
| 7,201,295 B1 | 4/2007 | Sitzberger |
| 7,209,042 B2 | 4/2007 | Martin et al. |
| 7,217,392 B2 | 5/2007 | Bogen et al. |
| 7,220,589 B2 | 5/2007 | Richards et al. |
| 7,226,788 B2 | 6/2007 | De La Torre-Bueno |
| 7,233,250 B2 | 6/2007 | Forster |
| 7,250,301 B2 | 7/2007 | Angros |
| 7,264,142 B2 | 9/2007 | Py |
| 7,270,785 B1 | 9/2007 | Lemme et al. |
| 7,275,682 B2 | 10/2007 | Excoffier et al. |
| 7,278,554 B2 | 10/2007 | Armstrong |
| 7,294,478 B1 | 11/2007 | Hinchcliffe |
| 7,303,725 B2 | 12/2007 | Reinhardt et al. |
| 7,314,238 B2 | 1/2008 | Robert |
| 7,323,491 B2 | 1/2008 | Lohray et al. |
| 7,338,803 B2 | 3/2008 | Mizzer et al. |
| 7,378,055 B2 | 5/2008 | Lemme et al. |
| 7,382,258 B2 | 6/2008 | Oldham et al. |
| 7,395,974 B2 | 7/2008 | Albany |
| 7,400,983 B2 | 7/2008 | Feingold et al. |
| 7,405,056 B2 | 7/2008 | Lam et al. |
| 7,425,306 B1 | 9/2008 | Kram |
| 7,435,381 B2 | 10/2008 | Pugia et al. |
| 7,435,383 B2 * | 10/2008 | Tseung et al. ............ 422/67 |
| 7,468,161 B2 * | 12/2008 | Reinhardt et al. ............ 422/63 |
| 7,470,401 B2 | 12/2008 | Morales |
| 7,470,541 B2 | 12/2008 | Copeland et al. |
| 7,476,362 B2 | 1/2009 | Angros |
| 7,501,283 B2 | 3/2009 | Hersch et al. |
| 7,553,672 B2 | 6/2009 | Bogen |
| 7,584,019 B2 | 9/2009 | Feingold et al. |
| 7,593,787 B2 | 9/2009 | Feingold et al. |
| 7,603,201 B2 | 10/2009 | Feingold et al. |
| 7,622,077 B2 | 11/2009 | Angros |
| 7,632,461 B2 | 12/2009 | Angros |
| 7,639,139 B2 | 12/2009 | Tafas et al. |
| 7,642,093 B2 | 1/2010 | Tseung et al. |
| 7,651,010 B2 | 1/2010 | Orzech et al. |
| 7,665,360 B2 | 2/2010 | Kurihara |

(56) References Cited

U.S. PATENT DOCUMENTS

| | | |
|---|---|---|
| 7,677,417 B2 | 3/2010 | Leiner et al. |
| 7,718,435 B1 | 5/2010 | Bogen et al. |
| 7,722,811 B2 | 5/2010 | Konrad et al. |
| 7,735,694 B2 | 6/2010 | Brown et al. |
| 7,744,817 B2* | 6/2010 | Bui .................... 422/68.1 |
| 7,760,428 B2 | 7/2010 | Sieckmann |
| 7,806,301 B1 | 10/2010 | Ciavarella et al. |
| 7,838,283 B2 | 11/2010 | Erickson et al. |
| 7,850,912 B2 | 12/2010 | Favuzzi et al. |
| 7,861,890 B2 | 1/2011 | McGill |
| 7,880,617 B2 | 2/2011 | Morris et al. |
| 7,887,755 B2 | 2/2011 | Mingerink et al. |
| 7,897,106 B2 | 3/2011 | Angros |
| 7,901,941 B2 | 3/2011 | Tseung et al. |
| 7,922,986 B2 | 4/2011 | Byrnard et al. |
| 7,937,228 B2 | 5/2011 | Feingold et al. |
| 7,951,612 B2 | 5/2011 | Angros |
| 7,960,178 B2 | 6/2011 | Key et al. |
| 7,980,425 B2 | 7/2011 | Baron et al. |
| 8,007,720 B2 | 8/2011 | Angros |
| 8,007,721 B2 | 8/2011 | Angros |
| 8,039,262 B2 | 10/2011 | Konrad et al. |
| 8,052,927 B2 | 11/2011 | Angros |
| 8,058,010 B2 | 11/2011 | Erickson et al. |
| 8,071,023 B2 | 12/2011 | Angros |
| 8,071,026 B2 | 12/2011 | Rapp et al. |
| 8,092,742 B2 | 1/2012 | Angros |
| 8,118,183 B2 | 2/2012 | Iwahashi et al. |
| 8,137,619 B2 | 3/2012 | Ford et al. |
| 8,142,739 B2 | 3/2012 | Tseung et al. |
| 8,216,846 B2 | 7/2012 | Ljungmann et al. |
| 8,236,255 B2 | 8/2012 | Takayama et al. |
| 8,257,968 B2 | 9/2012 | Sweet et al. |
| 8,283,176 B2 | 10/2012 | Bland et al. |
| 8,288,086 B2 | 10/2012 | Metzner et al. |
| 8,298,815 B2 | 10/2012 | Buchanan et al. |
| 8,315,899 B2 | 11/2012 | Samuhel et al. |
| 8,386,195 B2 | 2/2013 | Feingold et al. |
| 8,394,322 B2 | 3/2013 | Windeyer et al. |
| 8,394,635 B2 | 3/2013 | Key et al. |
| 8,396,669 B2 | 3/2013 | Cocks |
| 8,486,714 B2 | 7/2013 | Favuzzi et al. |
| 8,529,836 B2 | 9/2013 | Winther et al. |
| 8,554,372 B2 | 10/2013 | Windeyer et al. |
| 8,585,985 B2 | 11/2013 | Lihl et al. |
| 8,609,023 B1 | 12/2013 | Druyor-Sanchez et al. |
| 8,663,978 B2 | 3/2014 | Sweet et al. |
| 8,673,642 B2 | 3/2014 | Key et al. |
| 8,676,509 B2 | 3/2014 | De La Torre-Bueno |
| 8,887,964 B2 | 11/2014 | Jokitalo et al. |
| 8,969,086 B2 | 3/2015 | Key et al. |
| 8,969,087 B2 | 3/2015 | Bland et al. |
| 2001/0044603 A1 | 11/2001 | Harrold |
| 2002/0013194 A1 | 1/2002 | Kitano et al. |
| 2002/0079318 A1 | 6/2002 | Wurzinger |
| 2002/0110494 A1* | 8/2002 | Lemme et al. ............. 422/100 |
| 2002/0114733 A1 | 8/2002 | Copeland et al. |
| 2002/0182115 A1 | 12/2002 | Aghassi et al. |
| 2002/0192806 A1 | 12/2002 | Custance et al. |
| 2003/0100043 A1 | 5/2003 | Kalra et al. |
| 2003/0157545 A1 | 8/2003 | Jevons et al. |
| 2003/0203493 A1 | 10/2003 | Lemme et al. |
| 2004/0033163 A1 | 2/2004 | Tseung et al. |
| 2004/0033169 A1 | 2/2004 | Shah |
| 2004/0091395 A1 | 5/2004 | Ward et al. |
| 2004/0120862 A1 | 6/2004 | Lang et al. |
| 2004/0191128 A1 | 9/2004 | Bogen et al. |
| 2004/0197230 A1 | 10/2004 | Lemme et al. |
| 2004/0266015 A1 | 12/2004 | Favuzzi et al. |
| 2005/0019902 A1 | 1/2005 | Mathies et al. |
| 2005/0035156 A1 | 2/2005 | Hersch et al. |
| 2005/0064535 A1 | 3/2005 | Favuzzi et al. |
| 2005/0135972 A1 | 6/2005 | Lemme et al. |
| 2005/0150911 A1 | 7/2005 | Bach |
| 2005/0153453 A1 | 7/2005 | Copeland et al. |
| 2005/0164374 A1 | 7/2005 | Kram |
| 2005/0186114 A1* | 8/2005 | Reinhardt et al. ............. 422/65 |
| 2005/0191214 A1* | 9/2005 | Tseung et al. ................. 422/100 |
| 2005/0250211 A1 | 11/2005 | Reinhardt et al. |
| 2005/0281711 A1 | 12/2005 | Testa et al. |
| 2006/0019332 A1 | 1/2006 | Zhang et al. |
| 2006/0040341 A1 | 2/2006 | Bland et al. |
| 2006/0045806 A1 | 3/2006 | Winther et al. |
| 2006/0049208 A1 | 3/2006 | Daansen |
| 2006/0063265 A1 | 3/2006 | Welcher et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0120921 A1 | 6/2006 | Elliot et al. |
| 2006/0127283 A1 | 6/2006 | Tseung et al. |
| 2006/0134793 A1 | 6/2006 | Key et al. |
| 2006/0147351 A1 | 7/2006 | Falb et al. |
| 2006/0148063 A1* | 7/2006 | Fauzzi et al. ............. 435/286.4 |
| 2006/0151051 A1 | 7/2006 | Py et al. |
| 2006/0169719 A1 | 8/2006 | Bui |
| 2006/0171857 A1 | 8/2006 | Stead et al. |
| 2006/0172426 A1 | 8/2006 | Buchanan |
| 2006/0190185 A1 | 8/2006 | Ford et al. |
| 2006/0191952 A1 | 8/2006 | Kalra et al. |
| 2006/0239858 A1 | 10/2006 | Becker |
| 2006/0252025 A1 | 11/2006 | Nitta et al. |
| 2006/0263268 A9 | 11/2006 | Tseung et al. |
| 2006/0265133 A1 | 11/2006 | Cocks et al. |
| 2006/0269985 A1 | 11/2006 | Kitayama |
| 2006/0275889 A1 | 12/2006 | Angros et al. |
| 2007/0010912 A1* | 1/2007 | Feingold et al. ............. 700/245 |
| 2007/0038491 A1 | 2/2007 | Samuhel et al. |
| 2007/0068969 A1 | 3/2007 | Orzech et al. |
| 2007/0160494 A1 | 7/2007 | Sands |
| 2007/0270714 A1 | 11/2007 | Cushner et al. |
| 2007/0272710 A1 | 11/2007 | Bui |
| 2008/0035677 A1 | 2/2008 | Daansen |
| 2008/0102006 A1 | 5/2008 | Kram et al. |
| 2008/0118378 A1 | 5/2008 | Baron et al. |
| 2008/0135583 A1 | 6/2008 | Caswell et al. |
| 2008/0215625 A1 | 9/2008 | Veitch et al. |
| 2008/0217246 A1 | 9/2008 | Benn et al. |
| 2008/0226508 A1 | 9/2008 | Byrnard et al. |
| 2008/0235055 A1 | 9/2008 | Mattingly et al. |
| 2008/0254503 A1 | 10/2008 | Ljungmann et al. |
| 2008/0286753 A1 | 11/2008 | Erickson et al. |
| 2008/0305515 A1 | 12/2008 | Burgart et al. |
| 2009/0004691 A1 | 1/2009 | Erickson et al. |
| 2009/0028757 A1 | 1/2009 | Lihl et al. |
| 2009/0108033 A1 | 4/2009 | Quinn et al. |
| 2009/0241751 A1 | 10/2009 | Walter |
| 2009/0308887 A1 | 12/2009 | Woo et al. |
| 2009/0325309 A1 | 12/2009 | Favuzzi et al. |
| 2010/0017030 A1 | 1/2010 | Feingold et al. |
| 2010/0028978 A1 | 2/2010 | Angros |
| 2010/0068757 A1 | 3/2010 | Angros |
| 2010/0089921 A1 | 4/2010 | Ellenkamp-Van Olst et al. |
| 2010/0099133 A1 | 4/2010 | Egle et al. |
| 2010/0178668 A1 | 7/2010 | Elliot et al. |
| 2011/0056991 A1 | 3/2011 | Brown et al. |
| 2011/0079615 A1 | 4/2011 | Ophardt et al. |
| 2011/0167930 A1 | 7/2011 | Feingold et al. |
| 2011/0176977 A1 | 7/2011 | Tseung et al. |
| 2011/0269238 A1 | 11/2011 | Key et al. |
| 2011/0297703 A1 | 12/2011 | Wilson et al. |
| 2012/0003679 A1 | 1/2012 | Haberkorn |
| 2012/0179293 A1 | 7/2012 | Feingold et al. |
| 2012/0309044 A1 | 12/2012 | Ljungmann et al. |
| 2013/0029409 A1 | 1/2013 | Sweet et al. |
| 2013/0084567 A1 | 4/2013 | Buchanan et al. |
| 2013/0203103 A1 | 8/2013 | Feingold et al. |
| 2013/0217108 A1 | 8/2013 | Key et al. |
| 2013/0330252 A1 | 12/2013 | Winther et al. |
| 2014/0038232 A1 | 2/2014 | Key et al. |
| 2015/0031073 A1 | 1/2015 | Lemme et al. |

(56) References Cited

U.S. PATENT DOCUMENTS

FOREIGN PATENT DOCUMENTS

| CN | 1847821 | 10/2006 |
|---|---|---|
| DE | 385159 | 11/1923 |
| DE | 3902476 | 8/1990 |
| EP | 0185330 | 6/1986 |
| EP | 0557871 | 9/1993 |
| EP | 1 028 320 A2 | 8/2000 |
| GB | 2037255 | 7/1980 |
| JP | 61200966 | 12/1986 |
| JP | 3148067 | 6/1991 |
| JP | 6-510860 | 12/1994 |
| JP | 9-503060 | 3/1997 |
| JP | 10-501167 | 2/1998 |
| JP | 11170558 | 6/1999 |
| JP | 11258243 | 9/1999 |
| JP | 2000167318 | 6/2000 |
| JP | 2001095495 | 4/2001 |
| JP | 2001-509727 | 7/2001 |
| JP | 2001-512823 | 8/2001 |
| JP | 2001-522033 | 11/2001 |
| JP | 2002507738 | 3/2002 |
| JP | 2002510247 | 4/2002 |
| JP | 2002-522065 | 7/2002 |
| JP | 2003-057246 | 2/2003 |
| JP | 2004-533605 | 11/2004 |
| JP | 2009538426 | 11/2009 |
| JP | 2010510430 | 4/2010 |
| WO | WO 95/08774 | 3/1995 |
| WO | WO 95/26796 | 10/1995 |
| WO | WO 96/39260 | 12/1996 |
| WO | WO 99/08090 | 2/1999 |
| WO | WO 99/22867 | 5/1999 |
| WO | WO 00/09650 | 2/2000 |
| WO | WO 00/12994 | 3/2000 |
| WO | WO 01/41918 | 6/2001 |
| WO | WO 02/072264 | 9/2002 |
| WO | WO 03/054553 | 7/2003 |
| WO | WO 03/091710 | 11/2003 |
| WO | WO 03/106033 | 12/2003 |
| WO | WO 2004/059288 A2 | 7/2004 |
| WO | WO 2004/074847 A1 | 9/2004 |
| WO | WO 2005/000731 | 1/2005 |
| WO | WO-2015051295 | 4/2015 |

OTHER PUBLICATIONS

PCT Search Report for PCT Appln No. PCT/US2007/012400, mailed Nov. 16, 2007 (13 pages).
Office Action for Japanese Application No. 2006-34571 dated Feb. 27, 2008 (4 pages).
Office Action for European Application No. 06101498.1 dated Jun. 27, 2008 (9 pages).
Office Action for Japanese Application No. 2006-354547 dated Dec. 26, 2008 (7 pages).
Office Action for Chinese Application No. 200610007366.7 dated May 8, 2009 (21 pages).
Sakura Fineteck U.S.A. Inc., CN Office Action dated May 10, 2010 for Chinese Appln. No. 200610007366.7.
Sakura Fineteck U.S.A. Inc., Final office action dated May 25, 2010 for U.S. Appl. No. 11/441,668.
English Translation of DE385159, 2 Pages.
Sakura Finetek, Non -final Office Action mailed Aug. 2, 2011 for U.S. Appl. No. 11/441,668.
Sakura Finetek U.S.A., Japanese office action dated Jul. 6, 2011 for JP Appln. No. 2008-141687.
Sakura Finetek U.S.A., Sixth Office Action mailed Mar. 31, 2011 for Chinese Appln. No. 200610007366.7, 6 pages.
Sakura Finetek U.S.A., Third Office Action mailed Jun. 9, 2011 for CN Appln. No. 200610007365.2, 6 pages.
Sakura Finetek U.S.A., First Office Action mailed Mar. 31, 2011 for EP Appln. No. 04780745.8, 3 pages.
Sakura Finetek, Australian Office Action mailed Jan. 3, 2012 for 2007267881., 5 pages.
Sakura Finetek, Chinese office action dated Jan. 18, 2012 for CN 200780019204.8.
Sakura Finetek, Japanese Office Action mailed Mar. 1, 2012 for App No. 2008-141687., 8 pages.
Sakura Finetek, Chinese Office Action mailed Feb. 16, 2012 for Chinese App 200610004479.1., 23 pages.
Sakura Finetek, Japanese Office Action mailed Mar. 12, 2012 for Application No. 2008-141687., 7 pages.
Sakura Finetek, Non-Final Office Action mailed Mar. 27, 2012 for U.S. Appl. No. 11/441,668., 15 pages.
Sakura Finetek, Japanese Office Action mailed Jan. 30, 2012 for Application No. 2009-512152, 6 pages.
Sakura Finetek USA, Inc., Canadian Office Action dated Feb. 25, 2013 for Appln. No. 2652898.
Sakura Finetek USA, Inc., Final Office Action dated Mar. 14, 2013 for U.S. Appl. No. 13/018,609.
Sakura Finetek, Extended Search Report mailed Jun. 4, 2012 for EP Appln. No. 12153210.5, 6 pages.
Sakura Finetek, Japanese Office Action dated Jul. 19, 2012 for Appln. No. 2009-512152 with English translation, 4 pages.
Sakura Finetek, Office Action mailed Jun. 25, 2012; EP Appln No. 07795292.7, 6 pp.
Sakura Finetek, CN Notification of Reexamination dated Sep. 18, 2012 for Chinese Appln. No. 200610007366.7.
Sakura Finetek, Australian Office Action mailed Sep. 21, 2012 for Application No. 2007267881.
Sakura Finetek, Non-Final Office Action dated Oct. 23, 2012 for U.S. Appl. No. 13/018,609.
Sakura Finetek U.S.A., Inc., "Australian Examination Report", AU Application No. 2012202090, (Mar. 28, 2014).
Sakura Finetek U.S.A., Inc., "Brazilian Office Action", BR Application No. PI0602274-0, (Feb. 2, 2016).
Sakura Finetek U.S.A., Inc., "Chinese Office Action", CN Application No. 2012103596084, with English translation (Jan. 12, 2016), 12 pages.
Sakura Finetek U.S.A., Inc., "European office action", EP Application No. 12153210.5, (Jan. 7, 2015), 4 pages.
Sakura Finetek U.S.A., Inc., "European Office Action", EP Appln. No. 04780745.8, (Oct. 20, 2015), 6 pages.
Sakura Finetek U.S.A., Inc., "Final office action", U.S. Appl. No. 13/238,511, (Apr. 5, 2013).
Sakura Finetek U.S.A., Inc., "Final office action", U.S. Appl. No. 13/018,609, (Oct. 9, 2013).
Sakura Finetek U.S.A., Inc., "Final office action", U.S. Appl. No. 14/579,858, (Apr. 12, 2016).
Sakura Finetek U.S.A., Inc., "Japanese Office Action", JP Application No. 2009-512152, (Jul. 19, 2012).
Sakura Finetek U.S.A., Inc., "Japanese Office Action", JP Appln. No. 2012-012269, with English translation, (Jul. 7, 2015), 31 pages.
Sakura Finetek U.S.A., Inc., "Non-final office action", U.S. Appl. No. 14/579,858, (Dec. 22, 2015).
Sakura Finetek U.S.A., Inc., "Non-final office action", U.S. Appl. No. 13/238,511, (Jun. 13, 2014).
Sakura Finetek U.S.A., Inc., "Non-final office action", U.S. Appl. No. 14/297,537, (Aug. 21, 2014).
Sakura Finetek U.S.A., Inc., "Non-final office action", U.S. Appl. No. 13/238,511, (Nov. 29, 2012).
Sakura Finetek U.S.A., Inc., "Non-final office action", U.S. Appl. No.13/238,575, (Jan. 25, 2013).
Sakura Finetek U.S.A., Inc., "Non-final office action", U.S. Appl. No. 13/018,608, (Jul. 1, 2013).
Sakura Finetek U.S.A., Inc., "Notice of Allowance", U.S. Appl. No. 13/018,609, (Feb. 14, 2014).
Sakura Finetek U.S.A., Inc., "Notice of Allowance", U.S. Appl. No. 13/238,511, (Nov. 14, 2014).
Sakura Finetek U.S.A., Inc., "Notice of Allowance", U.S. Appl. No. 14/297,537, (Dec. 24, 2015).
Sakura Finetek U.S.A., Inc., "Office Action", BR Application No. PI0602274-0, (Aug. 18, 2015).
Sakura Finetek U.S.A., Inc., "Office Action", AU Application No. 2008229802 (Jul. 21, 2010).

(56) References Cited

OTHER PUBLICATIONS

Sakura Finetek U.S.A., Inc., "Office Action", AU Application No. 2008229802 (Aug. 13, 2010).
Sakura Finetek U.S.A., Inc., "Office Action", EP Application No. 07795292.7-1234 (Oct. 11, 2010).
European Search Report for EP Appln No. 06101495.7, mailed Dec. 18, 2006 (10 pages).
European Search Report for EP Appln No. 06101497.3, mailed Jun. 20, 2006 (6 pages).
Zhang, Guangrong, et al., "Deparaffinization compositions and methods for their use," U.S. Reissue Appl. No. 11/250,142, filed Oct. 13, 2005.
Shi, Shan-Rong, et al., "Enhancement of immunochemical staining in aldehyde-fixed tissue," U.S. Reissue Appl. No. 11/249,180, filed Oct. 11, 2005.
Sakura Finetek U.S.A., Inc., CN Office Action dated Mar. 31, 2011 for Chinese Appln. No. 200610007366.7, 6 pages.
Sakura Finetek U.S.A., Inc., Non-final Office Action mailed Feb. 18, 2011 for U.S. Appl. No. 11/441,668, 13 pages.
Sakura Finetek U.S.A., Inc., Office Action mailed Oct. 11, 2010; European Appln No. 07795292.7-1234, 7 pages.

* cited by examiner

Setup Slide Information Tables ✕

Please setup table name and description

| Name | Description |
|---|---|
| Patient | Patient Information |
| Physician | Physician Information |
|  |  |
|  |  |
|  |  |
|  |  |
|  |  |
|  |  |
|  |  |

[ Save ]   [ Exit ]

1500, 1510 (Name), 1520 (Description), 1530 (Save)

FIG. 16

Setup Slide Barcode Format ✕

Please enter the barcode date field destination

| Number | Length | Data Format |
|---|---|---|
| 1 | 1 | Alpha ▼ |
| 2 | 2 | Numerics ▼ |
| 3 |  | ▼ |
| 4 |  | ▼ |
| 5 |  | ▼ |
| 6 |  | ▼ |
| 7 |  | ▼ |
| 8 |  | ▼ |

Total data length: 3

[ Save ]   [ Exit ]

1600, 1610 (Number), 1620 (Length), 1630 (Data Format), 1640 (Save)

Cartridge Information

Module Name

| Location | ID | Abbreviated Name | Tests Left | On Board Expiry Date |
|----------|----|--------------------|------------|----------------------|

Exit

*FIG. 26*

Create/Edit Macro

Macro Data Fields

| | | |
|---|---|---|
| Macro ID | 3 | Emergency Substitution Solution Name |
| Macro Name | | Emergency Substitution Solution Temp (°C) |
| Revision | | Extended Incubation (%) |
| Reagent A | Bulk | Minimum Hold Times (Sec.) |
| Reagent B | | Maximum Hold Times (Sec.) |
| Water Bottle ID | w1 | |

Reagent A
- Cartridge Reagent ID
- Cartridge Reagent Abbreviated Name
- Bulk Solution ID
- Bulk Solution Abbreviated Name

| | | |
|---|---|---|
| Minimum Cycles | | bulk1 | Default Hold Times [Sec] |
| Maximum Cycles | | | Maximum Hold Temp (°C) |
| Default Cycles | | | Maximum Hold Temp (°C) |
| Variability | | | Default Hold Temp (°C) |

Reagent B
- Cartridge Reagent ID
- Cartridge Reagent Abbreviated Name
- Bulk Solution ID
- Bulk Solution Abbreviated Name

| Step Sequence No. | Action | Total Units | Platen Temp (°C) | Pellet Recess Temp (°C) | Cycle Step | Criticality Factor | Time |
|---|---|---|---|---|---|---|---|
| | Heat | | | 1 | bulk1 | Yes | |

[Add] [Edit] 3130 [Delete] [Undo] [Clear] [Save] [Exit]

Select Tray Reagent

Tray Reagent ID: 1 — 3410
Tray Reagent Abbreviated Name: atest1 — 3420

3430: [Create] [Edit] [Delete] [Exit]

Add New Tray Reagent

◉ Sakura Provided Tray Reagent — 3510
○ User Defined Tray Reagent — 3540

| Field | Field |
|---|---|
| Tray Reagent ID | Detection System |
| Full Name | Hazard Level |
| Abbreviated Name | Waste Type: Biohazard |
| Antibody Type | Stability |
| Antibody Source | Price |
| Clone | Inventory |
| Dilution | Minimum Stock Quantity |
| Primary Pre-Treatment | Last Received Date: 01/01/00 |
| Incubation Time | |

MSDS — 3520

[Save] [Exit] — 3530

3500

Edit Tray Reagent

○ Sakura Provided Tray Reagent     ○ User Defined Tray Reagent

| | | | |
|---|---|---|---|
| Tray Reagent ID | | Detection System | aa |
| Full Name | reagent1 | Hazard Level | aa |
| Abbreviated Name | latest1 | Waste Type | poison ▼ |
| Antibody Type | aa | Stability | 60 |
| Antibody Source | aa | Price | 11 |
| Clone | aa | Inventory | 1 |
| Dilution | aa | Minimum Stock Quantity | 1 |
| Primary Pre-Treatment | aa | Last Received Date | 01/01/00 ▼ |
| Incubation Time | aa | | |

MSDS [ aa ]

[ Save ] [ Exit ]

Select Cartridge Reagents

Cartridge Reagent ID [ ▼ ]     Cartridge Reagent Abbreviated Name [ rtest1 ▼ ]

[ Create ] [ Edit ] [ Delete ] [ Exit ]

*FIG. 37*

Add New Cartridge Reagent

⦿ Sakura Provided Cartridge Reagent     ○ User Defined Cartridge Reagent

Cartridge Reagent Data Fields

| | | | |
|---|---|---|---|
| Cartridge ID | [ ] | Package Size (ml) | [ ] |
| Full Name | [ ] | Stability (days) | [ ] |
| Abbreviated Name | [ ] | On-board Stability (days) | [ ] |
| Reagent Type | [ ] | Price | [ ] |
| Reagent Source | [ ] | Inventory (Bottles) | [ ] |
| Hazard Level | [ ] | Minimum Stock Quantity | [ ] |
| Waste Type | Biohazard ▼ | Last Received Date | 01/01/2000 ▼ |
| Product Code | [ ] | | |
| MSDS | | | |

[ Save ]     [ Exit ]

FIG. 38

Edit Cartridge Reagent

◉ Sakura Provided Cartridge Reagent  ○ User Defined Cartridge Reagent

Cartridge Reagent Data Fields

| Cartridge ID | | Package Size (ml) | 0 |
| Full Name | | Stability (days) | 0 |
| Abbreviated Name | rtest | On-board Stability (days) | 2 |
| Reagent Type | | Price | |
| Reagent Source | | Inventory (Bottles) | 0 |
| Hazard Level | | Minimum Stock Quantity | |
| Waste Type | Biohazard ▼ | Last Received Date | 01/01/2000 ▼ |
| Product Code | | | |
| MSDS | | | |

[ Save ]   [ Exit ]

FIG. 39

Select Bulk Solutions

Bulk Solution ID          Bulk Solution Abbreviated Name

[ Create ] [ Edit ] [ Delete ] [ Exit ]

Add New Bulk Solution  ☒

⦿ Sakura Provided Bulk Solutions  _4110_   ○ User Defined Bulk Solutions  _4140_

Bulk Solution Data Fields

| Solution ID | | Package Size (ml) | |
| Full Name | | Stability (days) | |
| Abbreviated Name | | Price | |
| Solution Type | | Inventory | |
| Hazard Level | | Minimum Stock Quantity | |
| Waste Type | ▼ | Last Received Date | 11/14/03 ▼ |
| Product Code | | | |

MSDS

_4120_

[ Save ]   [ Exit ]
_4130_

Edit Bulk Solution

○ Sakura Provided Bulk Solutions          ○ User Defined Bulk Solutions — *4240*

Bulk Solution Data Fields

| | | | |
|---|---|---|---|
| Solution ID | | Package Size (ml) | |
| Full Name | | Stability (days) | |
| Abbreviated Name | | Price | |
| Solution Type | | Inventory | |
| Hazard Level | | Minimum Stock Quantity | |
| Waste Type | [▼] | Last Received Date | 11/14/03 [▼] |
| Product Code | | | |

MSDS

*4210*
*4220*

[ Save ]     [ Exit ]

Setup Bulk Solution Bottles

| *4310* Bottle ID | *4320* Bulk Solution ID | *4330* Bulk Solution Abbreviated Name | *4340* Source | *4350* Capacity (L) |
|---|---|---|---|---|
| B1 | [▼] | [▼] | [▼] | |
| B2 | [▼] | [▼] | [▼] | |
| B3 | [▼] | [▼] | [▼] | |
| B4 | [▼] | [▼] | [▼] | |

[ Save ] *4360*     [ Exit ]

FIG. 43

Setup Waste Bottles

| Bottle ID (4410) | Waste Type ID (4420) | Waste Type (4430) | Location (4440) | Capacity (L) (4450) |
|---|---|---|---|---|
| W1 | 2 | Poison | | |
| W2 | | | | |
| W3 | | | | |
| W4 | | | | |

Save (4460)  Exit

FIG. 44

Create Worklist (4510)

WORKLIST: Worklist ID (4540)

| Na | Slide Information | Tray Information | | | | |
|---|---|---|---|---|---|---|
| | Slide ID | Tray Reagent ID | Tray Reagent ID Abbreviated Name | Program ID | Program Abbreviated Name | Changed? |

(4530)

SELECT ROW TO MAKE CHANGES DOUBLE CLICK TO DISPLAY SLIDE DETAILS (4520)

Display Slide Details | Adjust Program Variables | Delete Entry | Print Worklist | Close Worklist (4550)

FIG. 45

View Bulk Solution Bottles

| Bulk1 | Bulk2 | Bulk3 | Bulk4 |
|---|---|---|---|
| E☐☐☐☐☐☐☐☐ F | E☐☐☐☐☐☐☐☐ F | E☐☐☐☐☐☐☐☐ F | E☐☐☐☐☐☐☐☐ F |
| B1 | B2 | B3 | B4 |

Bottle Name

- Solution ID
- Solution Name
- Remaining Volume
  - (mL)
  - (%)
- Source
- Capacity (mL)
- Replenish Exit

*FIG. 51*

AUTOMATED REAGENT DISPENSING SYSTEM AND METHOD OF OPERATION

Priority is claimed to U.S. Provisional Patent Application Ser. No. 60/652,432, filed Feb. 11, 2005, and entitled "Automated Reagent Dispensing System and Method of Operation"; and U.S. Provisional Patent Application Ser. No. 60/678,682, filed May 6, 2005, and entitled "Automated Reagent Dispensing System and Method of Operation," the contents of both which are incorporated in their entireties herein by reference. This application is also a continuation-in-part of U.S. patent application Ser. No. 10/639,021, filed on Aug. 11, 2003, which issued on Feb. 17, 2005 as U.S. Pat. No. 7,501,283, and entitled "Fluid Dispensing Apparatus", which is incorporated in its entirety herein by reference.

FIELD OF THE INVENTION

The present invention is directed generally to tissue sample processing systems and in particular to systems and methods of dispensing reagents.

BACKGROUND OF THE INVENTION

Tissue processors can be operated with varying levels of automation to process human or animal tissue specimens for histology or pathology uses. Various types of chemical reagents can be used at various stages of tissue processing and various systems have been developed for delivering reagents to microscope slides containing specimens. Examples of known reagent delivery systems include small quantity release dispensers, technicians manually pouring reagents into reagent vats, and bulk containers connected with a specimen processor via tubing.

There are various disadvantages of known systems. For example, a technician manually pouring reagents into, or draining, reagent vats suffers the disadvantages of being time consuming and requiring pouring accuracy which decreases the overall efficiency of the tissue processing system. Another disadvantage is that manually pouring and draining reagents can be sloppy, requiring clean-up of spills and consequential instrument down-time. A further disadvantage is that selecting the correct reagent requires operator attention and accuracy and there is an increased possibility of reagent application errors, which decreases test accuracy and operational efficiency.

In the previously known automated systems, there are also disadvantages. In those systems, reagents are selected and administered to slides during processing, frequently via gravity promoted dispensing from above. Such delivery systems require specialized equipment for reagent delivery such as specialized reagent dispensers, drivers or automated pipetting systems. Such systems suffer various drawbacks such as the amount of effort required to set up and dispense the reagents, the possibilities of evaporation during processing or contamination and difficulties in handling minute quantities of large numbers of reagents.

SUMMARY OF THE INVENTION

The present invention alleviates to a great extent the disadvantages of the known automated slide staining systems. The invention reduces errors and increases efficiency in tissue processing by providing a central controller that may simultaneously operate multiple stainers in a scheduled manner. The central controller initiates tissue processing either automatically, for example, on a scheduled basis, or manually upon receiving a start event condition. The stainers undergo an inventory procedure that determines the number and types of tissue samples provided on slides that have been placed on trays in the stainers. This procedure may include scanning a bar code or otherwise obtaining patient, tissue, reagent, and/or other types of information from the slides and/or trays provided in the stainer.

The stainer transmits all or a portion of this information to the central controller. Preferably, the central controller at least receives primary reagent information regarding the tissue samples. Based on the primary reagent information, the central controller determines a staining protocol to be applied to the tissue samples. The staining protocols are communicated to and stored by the stainer. The stainer may then operate independently of the central controller.

The central controller enables a user to obtain a status regarding one or more tissue processes, generate reports, modify reagent cartridge information, select programs to run, and initiate other functions. The central controller may also enable the user to manually initiate tissue processing for one or more of the stainers.

These and other features and advantages of the present invention will be appreciated from review of the following detailed description of the invention, along with the accompanying figures in which like reference numerals refer to like parts throughout.

BRIEF DESCRIPTION OF THE DRAWINGS

FIG. 11 is a display associated with system setup in accordance with the present invention;

FIG. 15 is a display associated with slide information table setup in accordance with the present invention;

FIG. 16 is a display associated with barcode format setup in accordance with the present invention;

FIG. 26 is a display associated with viewing cartridge information in accordance with the present invention;

FIG. 31 is a display associated with creating/editing a macro in accordance with the present invention;

FIG. 34 is a display associated with selecting a tray reagent in accordance with the present invention;

FIG. 35 is a display associated with adding a new tray reagent in accordance with the present invention;

FIG. 36 is a display associated with editing a tray reagent in accordance with the present invention;

FIG. 37 is a display associated with selecting a cartridge reagent in accordance with the present invention;

FIG. 38 is a display associated with adding a new cartridge reagent in accordance with the present invention;

FIG. 39 is a display associated with editing a cartridge reagent in accordance with the present invention;

FIG. 40 is a display associated with selecting a bulk solution in accordance with the present invention;

FIG. 41 is a display associated with adding a new bulk solution in accordance with the present invention;

FIG. 42 is a display associated with editing a bulk solution in accordance with the present invention;

FIG. 43 is a display associated with bulk solution bottles setup in accordance with the present invention;

FIG. 44 is a display associated with waste bottles setup in accordance with the present invention;

FIG. 45 is a display associated with creating a user account in accordance with the present invention;

FIG. 51 is a display associated with viewing bulk solution bottle information in accordance with the present invention;

DETAILED DESCRIPTION

In the following paragraphs, the present invention will be described in detail by way of example with reference to the figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 1:
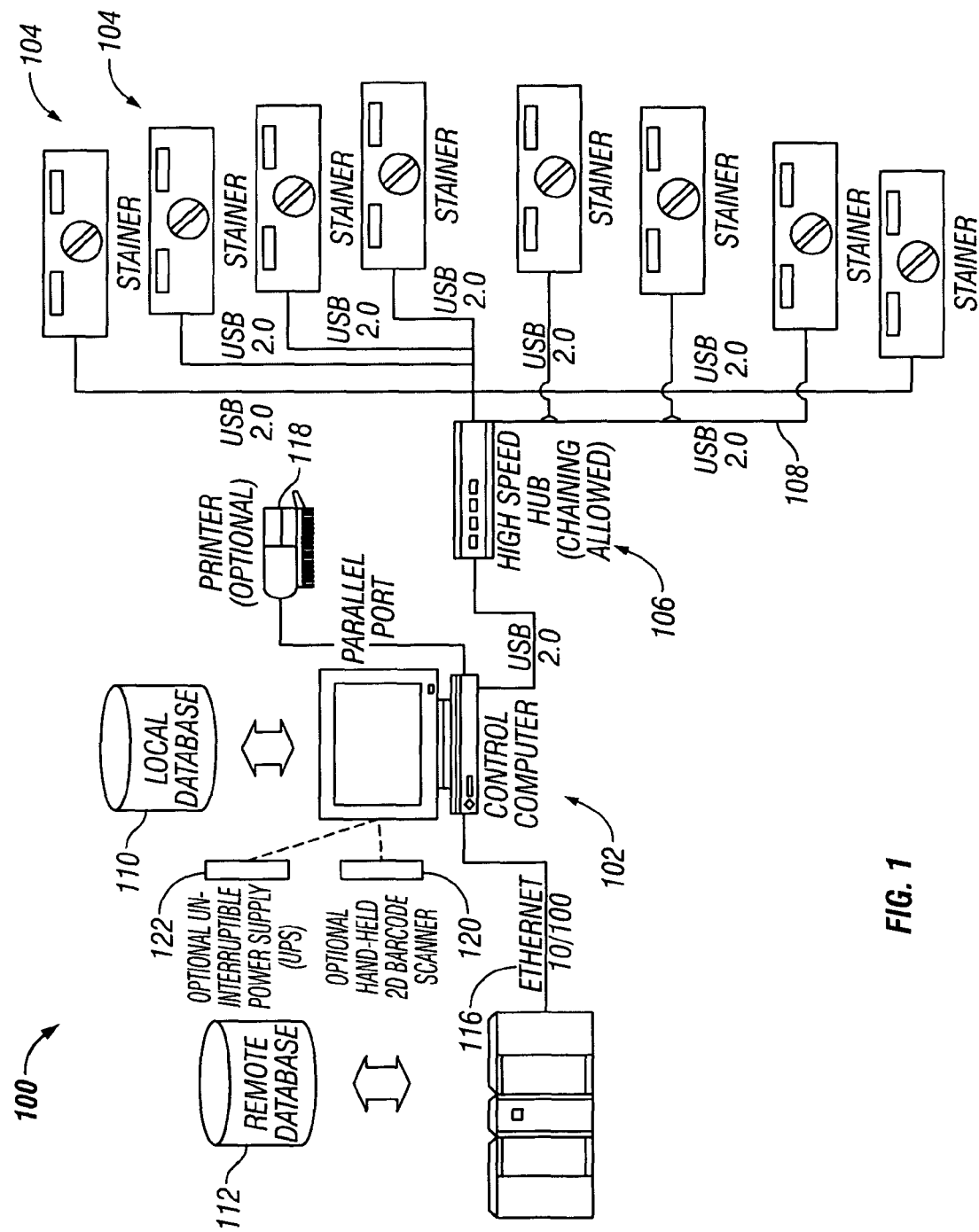
FIG. 1 is a schematic of an automated reagent dispensing system in accordance with the present invention.

FIG. 1 is an illustration of an automated reagent dispensing system 100 according to an embodiment of the present invention. A control computer 102 is in communication with a plurality of stainers 104 and may provide a centralized user interface for controlling the plurality of stainers 104. Stainers 104 may be used to process biological specimens as described below. Control computer 102 may communicate with stainers 104 in any manner known in the art, for example control computer 102 may communicate with stainers 104 via a high-speed hub 106. High-speed hub 106 enables dispensing system 100 to quickly convey information between the plurality of stainers 104 and the other components such as control computer 102. For example, stainers 104 may download staining protocols to be applied to slides placed in the stainers over a network formed by data lines 108 and high-speed hub 106. It shall be appreciated that control computer 102 and stainers 104 may be configured to communicate through hardwires or wirelessly, for example, the system may utilize data lines 108, as described above, which may be conventional conductors or fiber optics. Additionally, the components may communicate wirelessly such as using radio frequency communication, such as BLUETOOTH (a registered trademark of Bluetooth SIG, Inc., of Bellevue, Wash.), or any other wireless technology.

Control computer 102 may also communicate with one or more local databases 110 so that data may be transferred to or from local databases 110. For example, local database 110 may store a plurality of staining protocols that are designed to be performed by stainers 104. The staining protocols implemented by stainers 104 may be chosen based on information obtained from identifiers (e.g., barcodes, radio frequency identification devices (RFID), etc.) associated with slides and/or trays used in the stainers, as further described below. Control computer 102 may process identification data received from stainers 104 and retrieve staining protocols from local database 110 and transmit the staining protocols to stainers 104. Furthermore, control computer 102 may use local databases 110 for storage of information received from stainers 104, such as reports and/or status information.

Control computer 102 may also communicate with one or more remote databases 112 and/or a server 114. Control computer 102 may communicate with remote database 112 directly or through server 114, which may be a laboratory information system (LIS). Control computer 102 may communicate with server 114 via a network 116. As noted above, server 114 may communicate with remote database 112. Server 114 and remote database 112 maybe used to provide staining protocols to be used by stainers 104 in a similar fashion as local database 110 or to supplement the protocols provided by local database 110.

Automated reagent dispensing system 100 may optionally include one or more printers 118. Printer 118 may communicate directly with control computer 102, as shown, or directly with stainers 104. Furthermore, stainers 104 may each have a dedicated printer 118 that may be integrated into the stainers or free-standing, or multiple stainers 104 may share one or more printers.

Automated reagent dispensing system 100 may also include a hand-held or desktop scanner 120 for reading identifiers that may be included throughout the system components (e.g., on microscope slides, trays, reagent containers, etc.). Any type of scanner 120 may be utilized that is capable of interpreting the identifiers. For example, scanner 120 may be an RFID scanner, a 2D or 3D barcode scanner, or any other type of scanner known in the art. Scanner 120 may communicate directly with control computer 102 or stainers 104 and each component may have a dedicated scanner.

The system may also be powered by an uninterruptible power supply 122. Uninterruptible power supply 122 may be used to limit the susceptibility of the system to general power failures that may invalidate tests that are interrupted. Such an interruption in power could also result in the tissue samples becoming unusable which could require gathering additional specimens. Power supply 122 may be used to power any or all of the components of automated reagent dispensing system 100.

Although control computer 102 is shown networked with multiple stainers 104 in FIG. 1, it shall be appreciated that a stainer may combined in single unit with an onboard control computer, in addition to any other component described above in the automated reagent dispensing system. Such a combination may provide a compact, stand-alone unit that may be used to process lower volumes of biological specimens.

Figure 2:
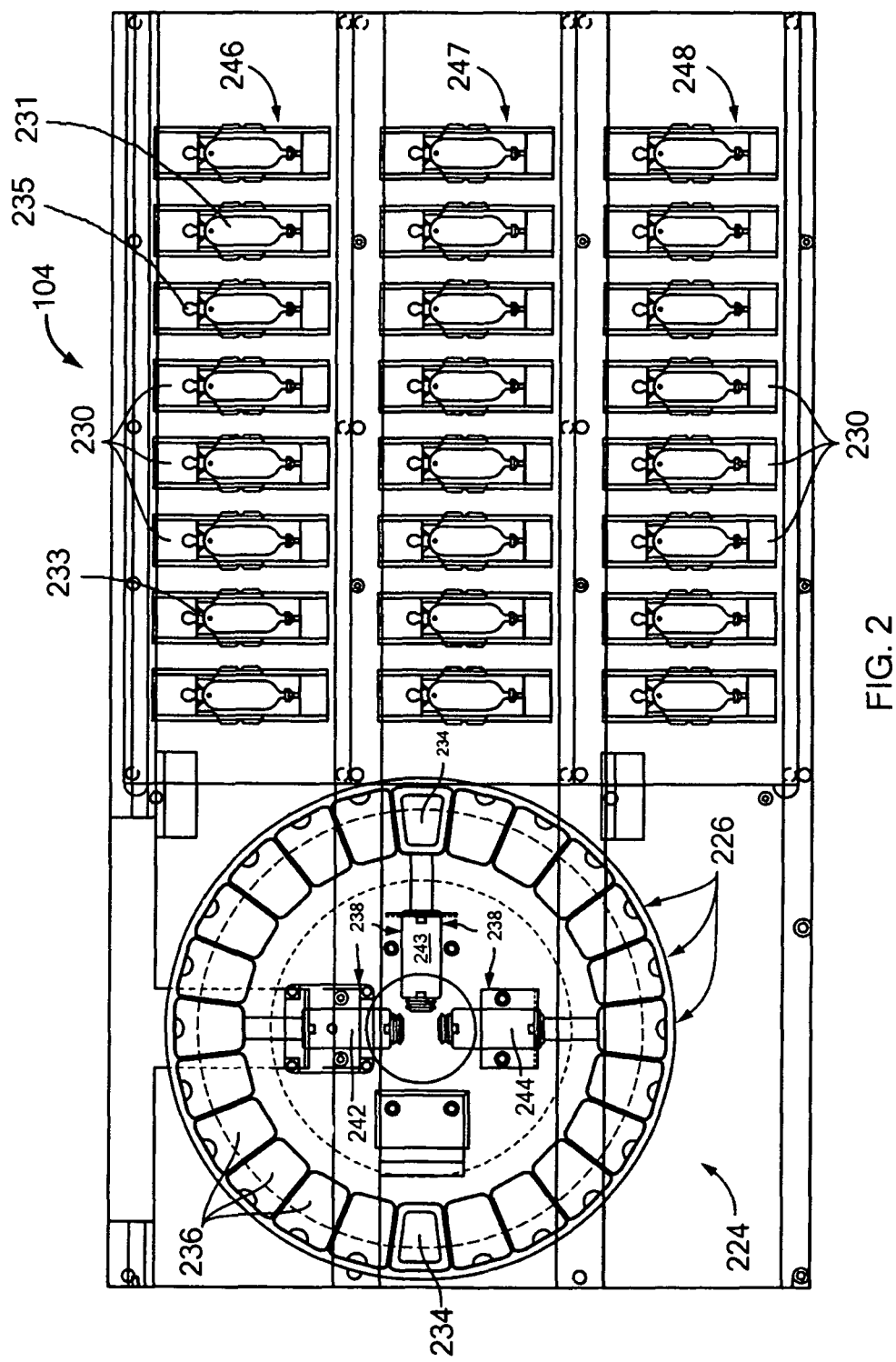
FIG. 2 is a top view of a tissue processing system suitable for use with one or more slide retaining trays in accordance with the present invention.
Figure 3:
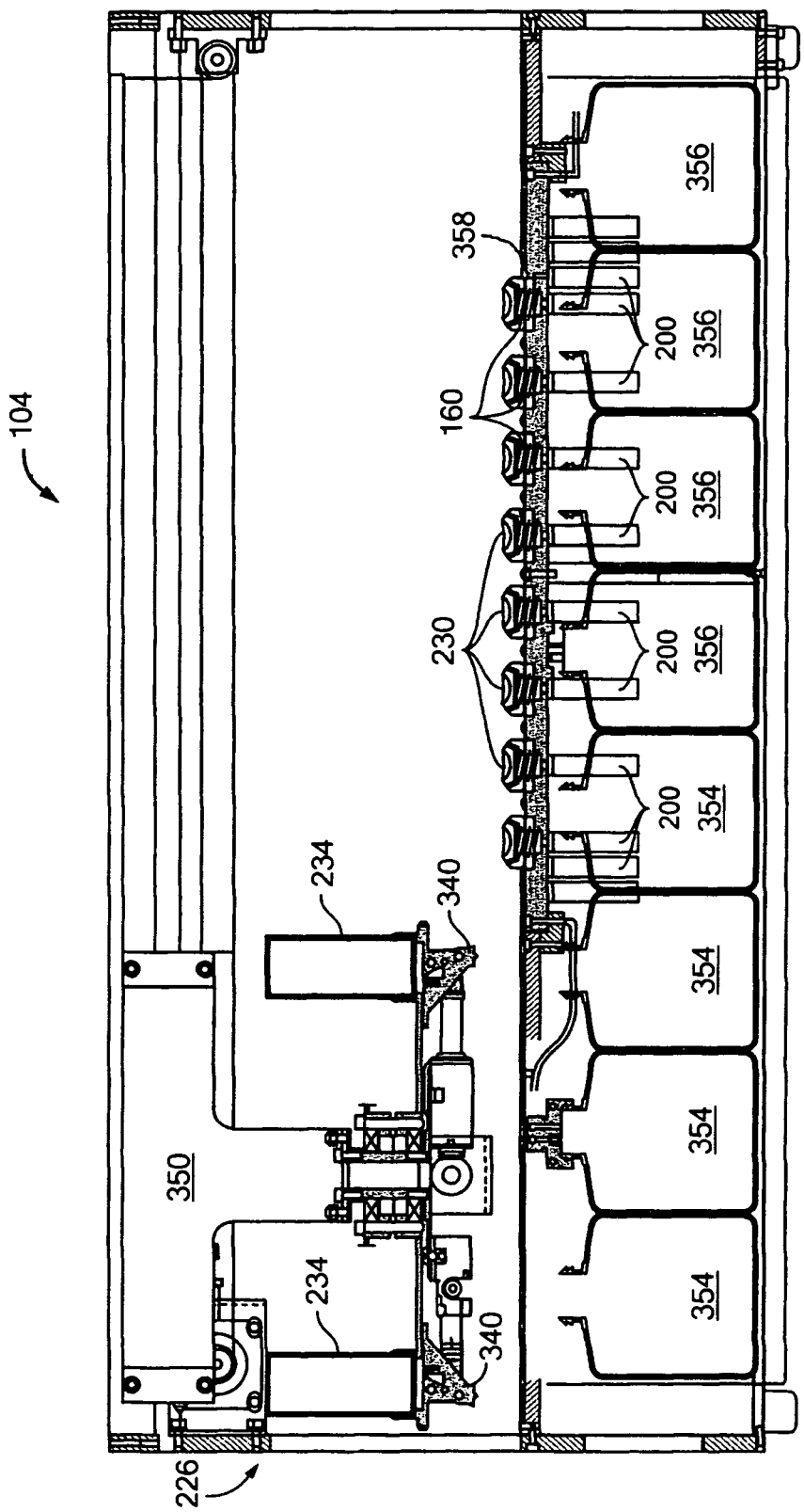
FIG. 3 is a side partial cross-sectional view of the tissue processing system of FIG. 1.

Referring to FIGS. 2 and 3, a stainer 104 suitable for use in automated reagent dispensing system 100 is shown. Stainer 104 generally includes a housing 224, a fluid dispensing apparatus 226 and a plurality of tray support-stations 228. Stainer 104 is configured so that multiple biological specimens each of which is supported by a retaining tray 230, may be efficiently processed. Housing 224 supports fluid dispensing apparatus 226 and tray support surface 228 and provides an enclosure in which the processing of the biological specimens may be contained.

Fluid dispensing apparatus 226 includes a plurality of stations 232 at which a plurality of fluid dispensing cartridges 234 may be mounted. Stations 232 include mounting apertures 236 selectively positioning a plurality of fluid dispensing cartridges 234 adjacent to an actuator assembly 238, which is used to trigger the ejection of a desired amount of a fluid, such as a secondary reagent or a de-waxing fluid, from a fluid dispenser 340 that may be integrated into fluid dispensing cartridge 234. An example of a fluid dispensing apparatus including a multiplicity of fluid dispensing cartridges is described in U.S. patent application Ser. No. 10/639,021, the content of which is hereby incorporated by reference in its entirety. Alternatively, a fluid dispensing system using tubing or pipetting may be used, such as the system described for example in U.S. Pat. No. 5,338,358.

Retaining trays 230 are positioned on tray support stations 228 and may be configured to hold microscope slides, as shown, and/or specimen containers. As shown in FIG. 3, retaining trays 230 are located in rows 246, 247, 248 generally beneath fluid dispensing apparatus 226. As a result, the system may take advantage of gravity to deliver fluids from a cartridge 234 onto a drip surface 233 of a desired retaining tray 230. Trays 230 may include a specimen support plateau 231 that is outlined by a raised sidewall and may include fluid inlet and outlet ports 237 and 239, respectively. When a microscope slide is placed onto tray 230 it is supported by the raised sidewall thereby forming a gap between plateau 231 and the slide. As described below, the specimen may be exposed to a fluid by flowing the fluid through the gap. Trays 230 may also include a reagent recess 235 for holding a reagent-containing gel or solid.

Preferably, fluid dispensing apparatus 226 and retaining trays 230 are movable with respect to one another so that cartridges 234 may be positioned to dispense fluids on any desired tray 230. Any combination of movability of fluid dispensing apparatus 226 and retaining trays 230 may be utilized. For example, both fluid dispensing apparatus 226 and retaining trays 230 may be movable or only one may be movable and the other stationary.

Actuator assembly 238 optionally includes a plurality of actuators 242, 243, 244, which may be used to selectively dispense fluid onto respective rows 246, 247, 248, of retaining trays 230. In the embodiment shown, dispensing actuator 242 is configured to dispense fluids onto retaining trays 230 disposed in row 246, dispensing actuator 243 is configured to dispense fluids onto retaining trays 230 disposed in row 247 and dispensing actuator 244 is configured to dispense fluids onto retaining trays 230 disposed in row 248. Of course, as will be understood by those of skill in the art, any number of actuators and/or slide retaining trays can be employed without departing from the scope of the present invention.

In an example of operation of stainer 104, fluid dispensing apparatus 226 is rotated so that individual cartridges 234 are selectively positioned adjacent actuators 242, 243, 244 of actuator assembly 238. Alternatively, an actuator may be positioned adjacent to each cartridge 234 such that rotation of the fluid dispensing apparatus 226 with respect to actuator assembly 238 is not required. Actuator assembly 238 may be any activation device that triggers cartridge 234 to emit a controlled amount of fluid. Preferably, fluid dispensing apparatus 226 may be both translated and rotated with respect to retaining trays 230 so that an individual cartridge 234 can be selectively positioned above any retaining tray 230. After cartridge 234 is positioned above a selected retaining tray 230, actuator assembly 238 triggers cartridge 234 to emit a controlled amount of fluid onto retaining tray 230.

In a preferred embodiment, the fluid dispensing apparatus 226 may be coupled to a support member 350 such that cartridges 234 maybe rotated with respect to actuator assembly 238. Actuator assembly 238 may be fixedly attached to support member 350, optionally beneath fluid dispensing cartridges 234. Preferably, support member 350 may be translated horizontally such that cartridges 234 can be both rotated and translated with respect to the trays 230. In this manner, any cartridge 234 can be selectively positioned above any retaining tray 230.

Retaining trays 230 preferably are mounted to tray support stations 228 on spring loaded heating/cooling pads 352, thereby providing selective and/or independent heating and/or cooling of retaining trays 230 and their associated slides and/or specimen containers. Additionally, heating/cooling pads 352 are capable of independently heating the plateau or platen region and the recess region. In an embodiment, each tray 230 has a corresponding heating and/or cooling element 352, maintaining retaining tray 230 at a particular desired temperature. In an alternative embodiment, there may be two or more heating and/or cooling elements for each retaining tray 230.

Stainer 104 optionally includes bulk fluid supply containers 354, waste fluid containers 356 and one or more fluid delivery manifolds 358. Supply containers 354 may be used to hold liquids such as water for rinsing or flushing the gap between a microscope slide, or specimen container, and platen, or plateau, 231 of a respective retaining tray 230. Fluid delivery manifold 358 preferably includes valves and switches (not shown) for directing the flow of fluids from supply containers 354, through an inlet port and conduit of manifold 358, to retaining trays 230. In addition, fluid delivery manifold 358 may include valves and switches (not shown) for directing the flow of excess fluids and waste material from fluid evacuation ports and conduits of manifold 358 into waste fluid containers 356.

Stainer 104 may also include a scanning device (not shown) for scanning identifiers included on retaining trays 230 or specimen slides or containers. The scanning device may be coupled to fluid dispensing apparatus 226, for example, so that information may be read from identifiers on retaining trays 230 as fluid dispensing apparatus 226 is translated over retaining trays 230. The scanning device may also be configured so that stations 232 for reagent cartridges 234 may be moved relative to the scanning device so that identifiers included on cartridges 234 may also be read by the scanning device.

Figure 4:
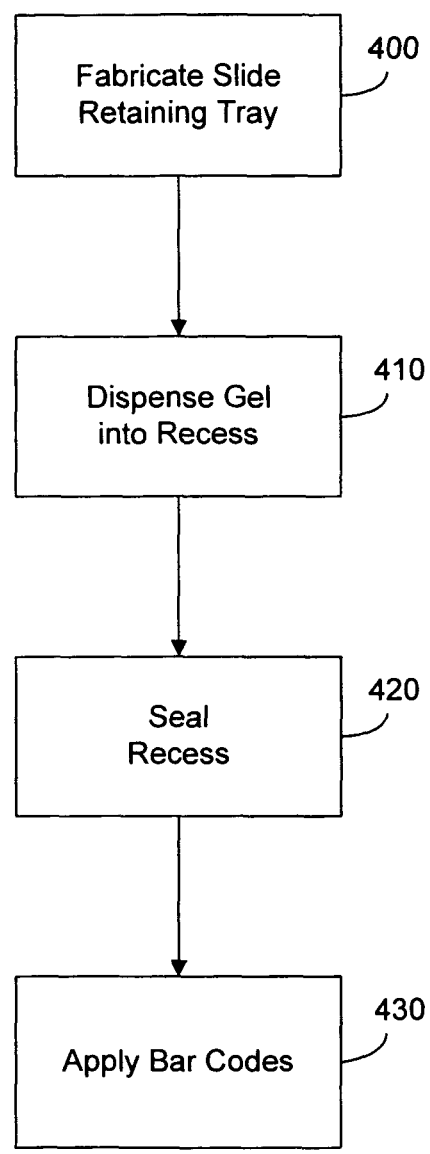
FIG. 4 is a flowchart depicting a method of manufacturing a retaining tray in accordance with the present invention.

A method of manufacturing a slide retaining tray 230 according to the principles of the present invention will now be described with respect to FIG. 4. As illustrated diagrammatically as box 400, the initial step involves fabricating retaining tray 230. According to a preferred embodiment, retaining tray 230 is fabricated from a polymeric material that is injection molded to form the desired structural shape. However, as would be understood to those of ordinary skill in the art, any fabrication process can be used or material selected that can achieve the desired structural features, without departing from the scope of the present invention. For example, retaining tray 230 may be constructed using any known technique such as injection molding, machining, vacuum/pressure forming, die casting, etc. Furthermore, any material known in the art may be used including polymeric and metallic materials. For example, tray materials may include urethane, polyurethane, acetal, stainless steel, aluminum, etc.

The next step involves dispensing a desired quantity of reagent into reagent recess 235 (shown in FIG. 2) as indicated by box 410. For example, a predetermined amount of a gel matrix containing a reagent may inserted through apertures in the bottom surface of the recess, or alternatively such a material can be inserted from above. Examples of the gel matrix include distilled water, distilled water with surfactant, buffering solution, etc.

After filling the recess, it may be sealed. As illustrated diagrammatically as box 420, the next step involves sealing the recess. The recess may be sealed in any way known in the art, for example the recess may be sealed by applying tape, or another sealing material such as a meltable material that can allow the recess to become open upon melting of the reagent containing matrix. Any form of seal may be selected that can retain the reagent in place and reduce vaporization and/or fluidic flow loss. For example, a mechanical seal can be applied as discussed above.

After a reagent is loaded into the reagent recess and the recess is sealed, an identifier may be affixed to the retaining tray as shown by box 430. The identifier may be used to track the location and processing of a particular biological specimen. It may also be used to correlate a biological specimen with the reagent contained in the recess of the retaining tray so that reagent specific processing may be performed. The identifier may also contain information about the specimen, requested processing and/or requesting physician. Any type of identifier may be used such as, for example, two or three dimensional barcodes, RFID devices, scanable microchips, etc. as will be appreciated by a person having ordinary skill in the art.

Figure 5:
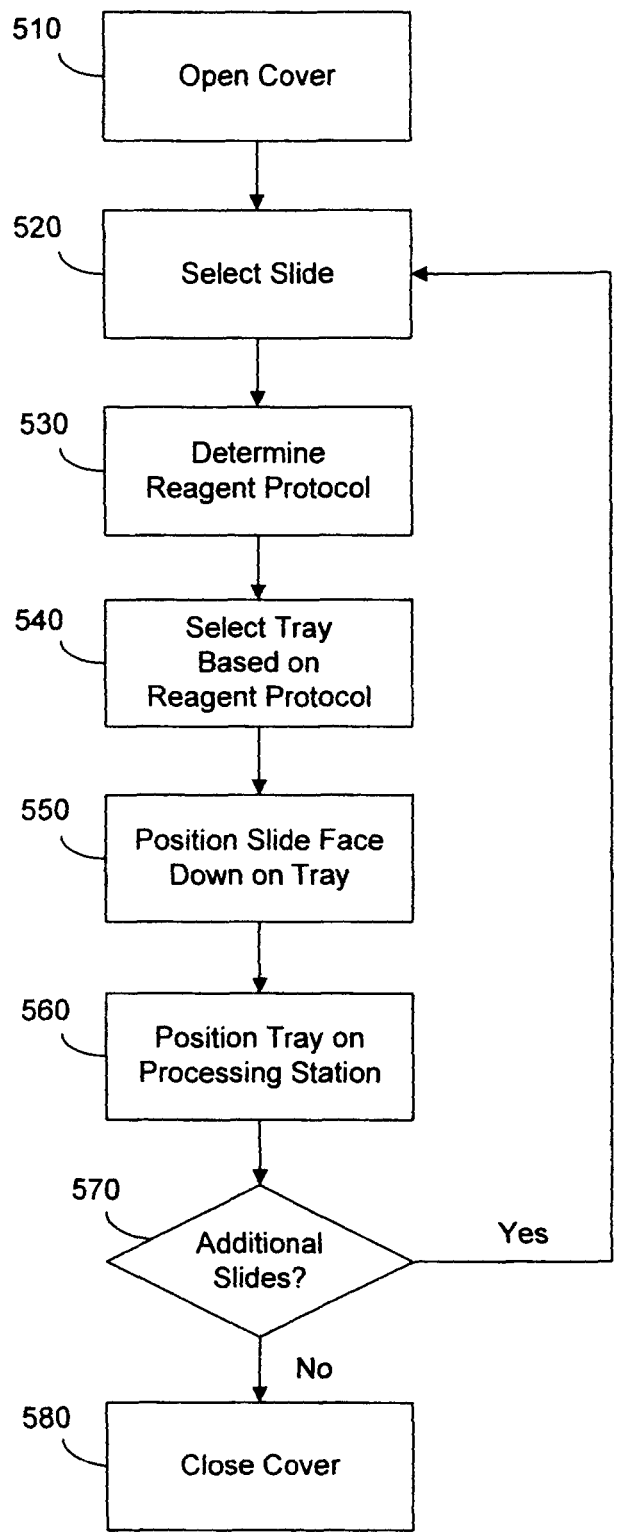
FIG. 5 is a flowchart depicting a tray loading procedure in accordance with the present invention.

Prior to initiating a procedure, specimens on retaining trays are loaded into a stainer that is included in the system. As shown in FIG. 5, a process for loading retaining trays into the system may be performed as shown. In the first step, a cover on the housing of a stainer is opened as indicated by box 510. Next, a slide containing a biological specimen or a specimen container holding a specimen is selected, as shown diagrammatically as box 520. After a slide or specimen container is selected a reagent protocol may be determined, as indicated by box 530, based on the tissue type, a diagnostician's or pathologist's directions, a predetermined procedure or in any other manner. A tray may then be selected based on the selected reagent protocol, as indicated by box 540. As described above, the retaining tray may be preloaded with a reagent containing matrix so the tray may be specific to certain reagent protocols. Therefore, preferably a tray is selected to match the selected reagent protocol. The slide, or specimen container, may then be loaded onto the selected tray, as shown by box 550. The slide may be placed on the retaining tray face down to facilitate the exposure of the specimen to fluids flowing through the retaining tray. After the slide or container is loaded onto the retaining tray, the retaining tray may be loaded into a stainer, or other processing apparatus, included in the automated system, as shown by box 560.

The steps of selecting a slide, determining a reagent protocol, selecting a tray, positioning the slide on a tray and positioning the tray on the stainer may be repeated until the tray capacity of the stainer is met as indicated by box 570. For example, in an embodiment, a stainer of the present system may have a twenty-four (24) tray capacity as shown in FIG. 2. Finally, after all of the desired specimens are loaded into the stainer, the operator may close the cover as indicated by box 580.

Figure 6:
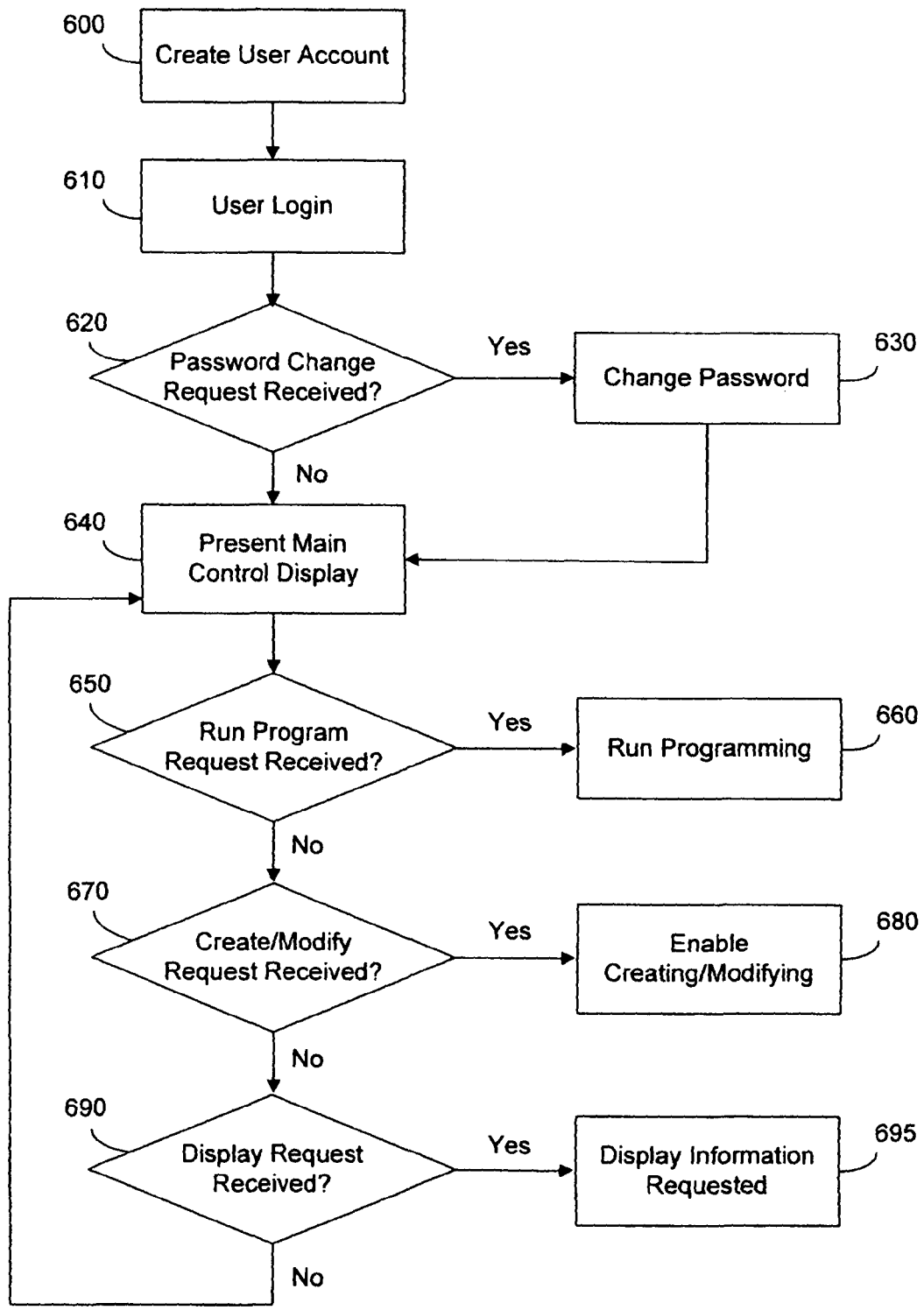
FIG. 6 is a flowchart depicting an overall system procedure in accordance with the present invention.
Figure 7:
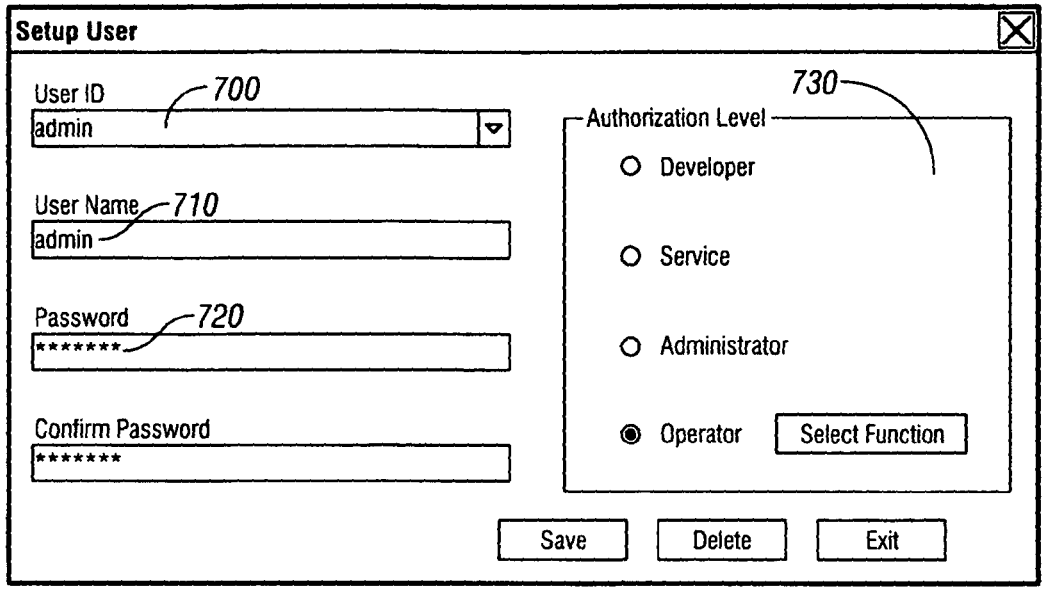
FIG. 7 is a display associated with creating a user account in accordance with the present invention.
Figure 8:
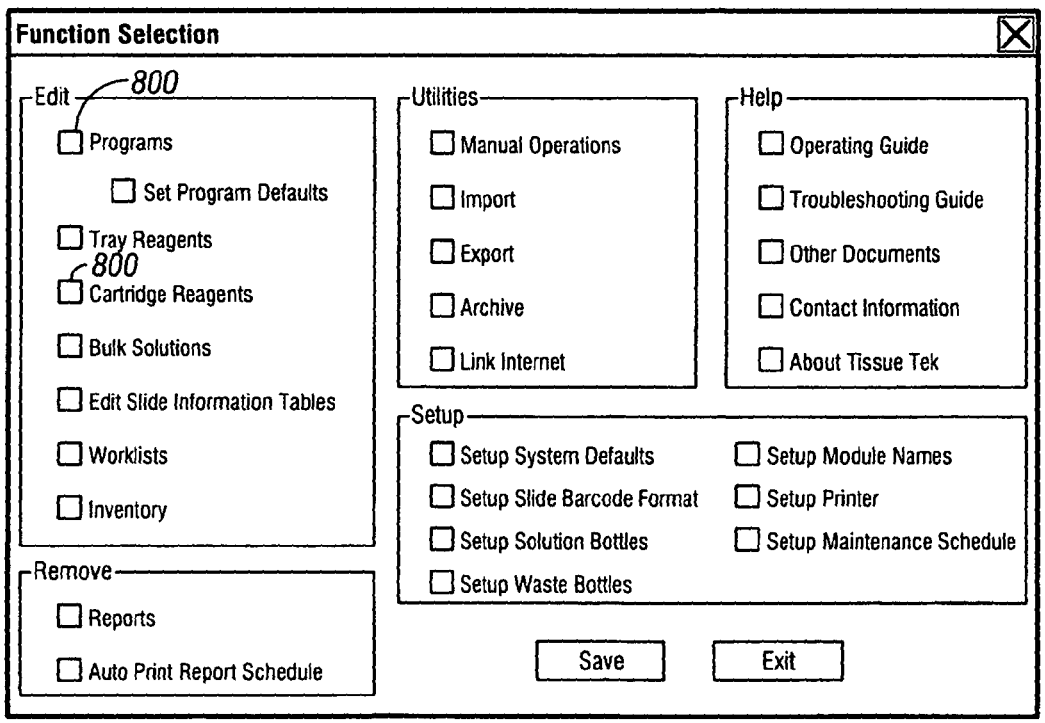
FIG. 8 is a display associated with creating a user account in accordance with the present invention.

FIG. 6 illustrates diagrammatically an overall system procedure according to one embodiment of the invention. An initial step, illustrated diagrammatically as box 600, a user account is created. Examples of displays associated with creating a user account are shown in FIGS. 7-8. A user account may be created by establishing a user identification 700, name 710 and password 720 through a user setup display shown in FIG. 7. Each user account may be assigned an authorization level 730. Such authorization levels 730 may include, for example, developer, service, administrator, operator, etc. Each authorization level 730 may have different privileges enabled for use with the system.

Additionally, an administrator setting up a user may manually limit that user's ability to perform various operations. For example, the administrator may prohibit the user from editing programs or performing manual operations. An administrator may limit the user's access to various operations through a function selection display, as shown in FIG. 8. The administrator may select the functions to which a particular user may have access, such as by selecting a checkbox 800 associated with the particular function. As shown, an administrator may control the ability of a user to edit programs, tray reagents, cartridge reagents, bulk solutions information tables worklists and inventory. The administrator may also control the user's ability to enter manual operations, import or export data, archive information, link to the internet, run reports, schedule reports, or to set up system defaults, barcode format, solution bottles, waste bottles, module names, printers or maintenance schedules. This may be performed by selecting a checkbox, radio button, toggle switch or other selectable feature adjacent a desired function. Any combination of functions may be selected.

Figure 9:
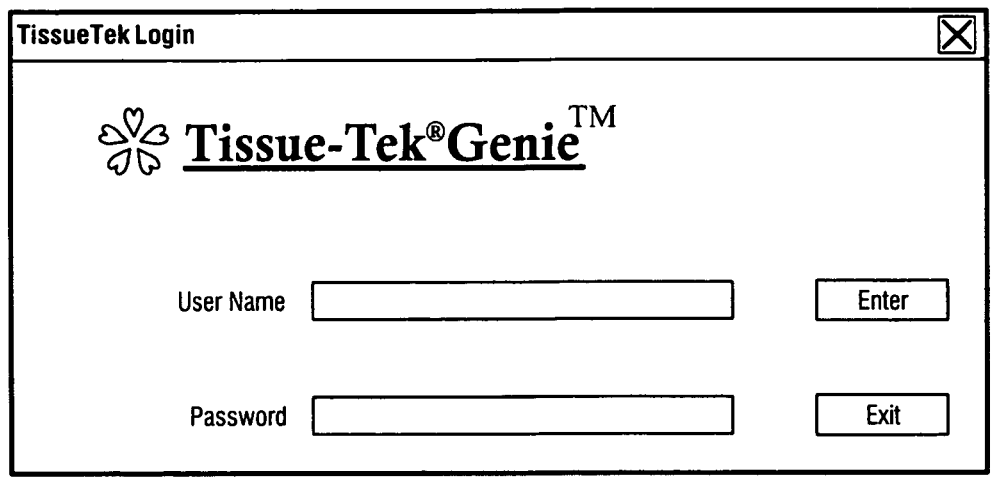
FIG. 9 is a display associated with a user login in accordance with the present invention.

After creating the user account, the user may login as illustrated diagrammatically as box 610 of FIG. 6. The user may be presented with a login display as shown in FIG. 9. The user may enter the username 710 and password 720 that were selected during step 600 of FIG. 6, during which a user account was created, to login to the automated system.

Figure 10:
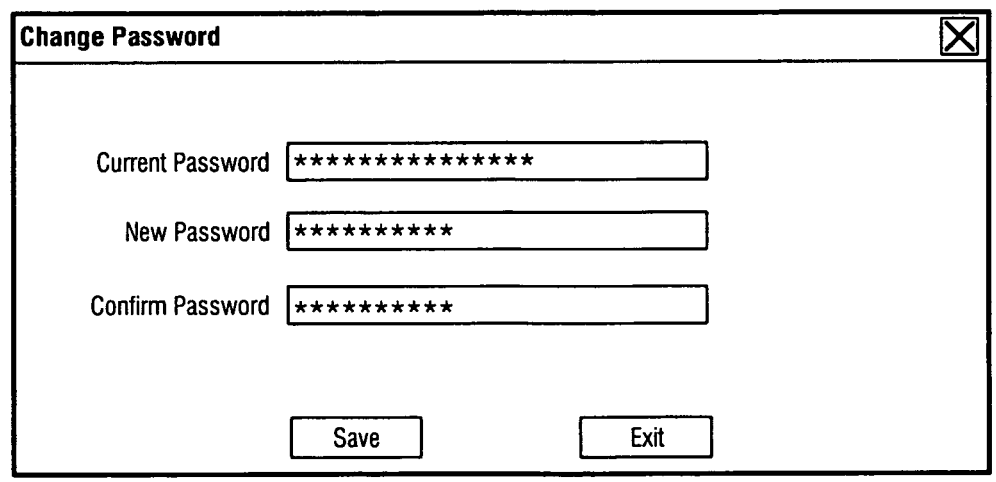
FIG. 10 is a display associated with changing a user password in accordance with the present invention.

Next, the user may elect or be required to change his/her password as indicated by box 620 in FIG. 6. In that step, a determination is made by the system to determine whether a password change request has been received. If a password change request has been received, a change password display, shown in FIG. 10, may be presented to the user as illustrated diagrammatically as box 630.

Figure 11:
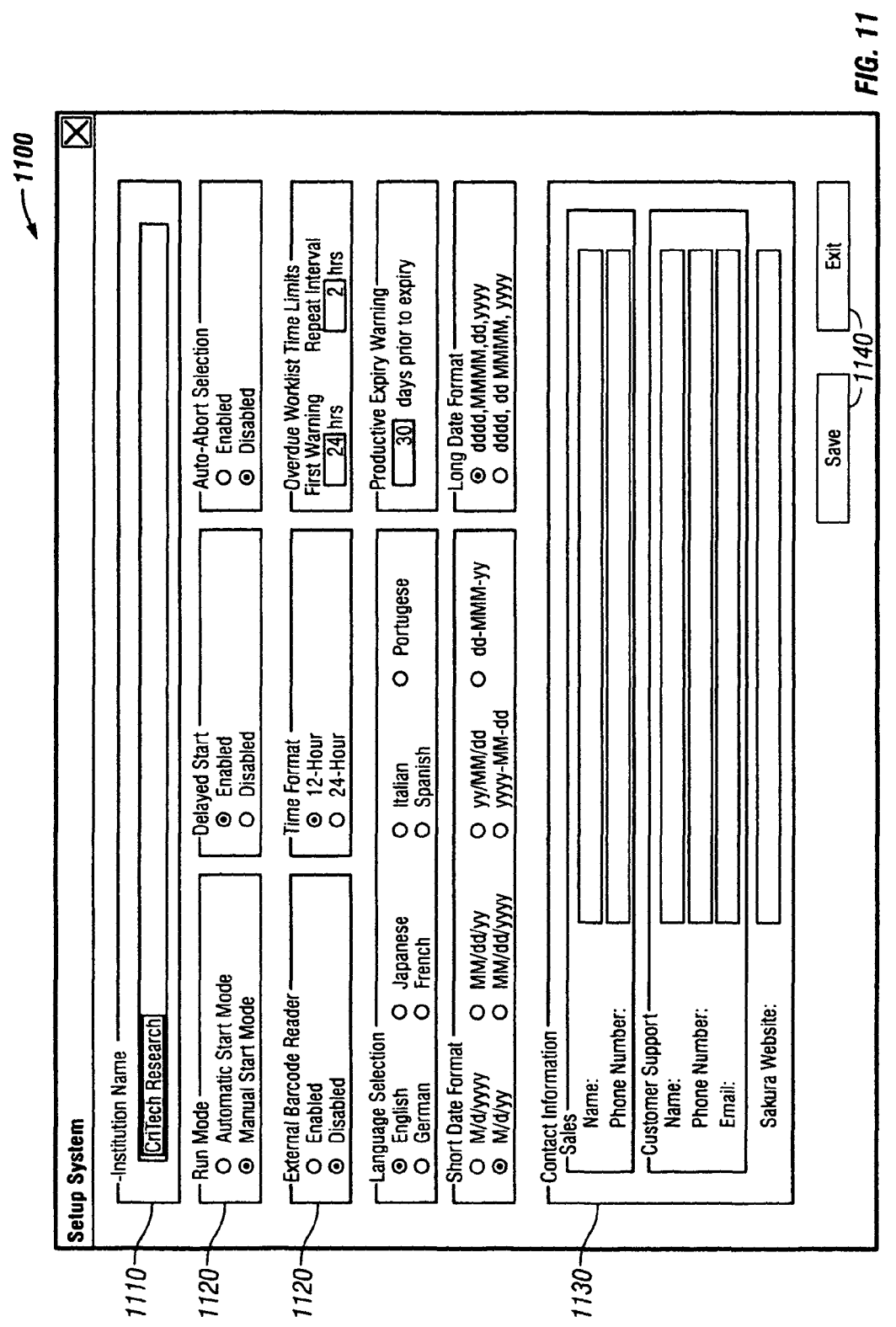

After a user has created an account, they may edit system preferences through a system setup display. FIG. 11 illustrates a display 1100 that may be presented to a user to during an initial system setup according to an embodiment of the present invention. The display 1100 may include a name section 1110 that enables the user to assign a name to a particular system setup. One or more preference sections 1120 may be provided to enable the user to assign system preferences. For example, the preference sections 1120 may enable the user to assign a run mode (automatic/manual start), external barcode reader status (enabled/disabled), language (English, German, Japanese, Italian, Spanish, French, Portuguese or other language), short date format (M/d/yyyy, MM/dd/yy, yy/MM/DD, dd-MMM-yy, M/d/yy, MM/dd/yyyy, and yyyy-MM-dd), long date format (dddd MMMM dd yyyy, ddd dd MMMM yyyy), auto-abort selection status (enabled/disabled), overdue worklist time limits (first warning (hrs.), time limits repeat interval (hrs)), and product expiry warning.

A contact information section 1130 may also be provided to enable the user to input contact information such as name, phone number, electronic mail address, web site or other information for a sales, customer support or other person associated with the system. Selectable function keys 1140 may also be presented to enable the user to save the settings and exit display 1100.

Figure 12:
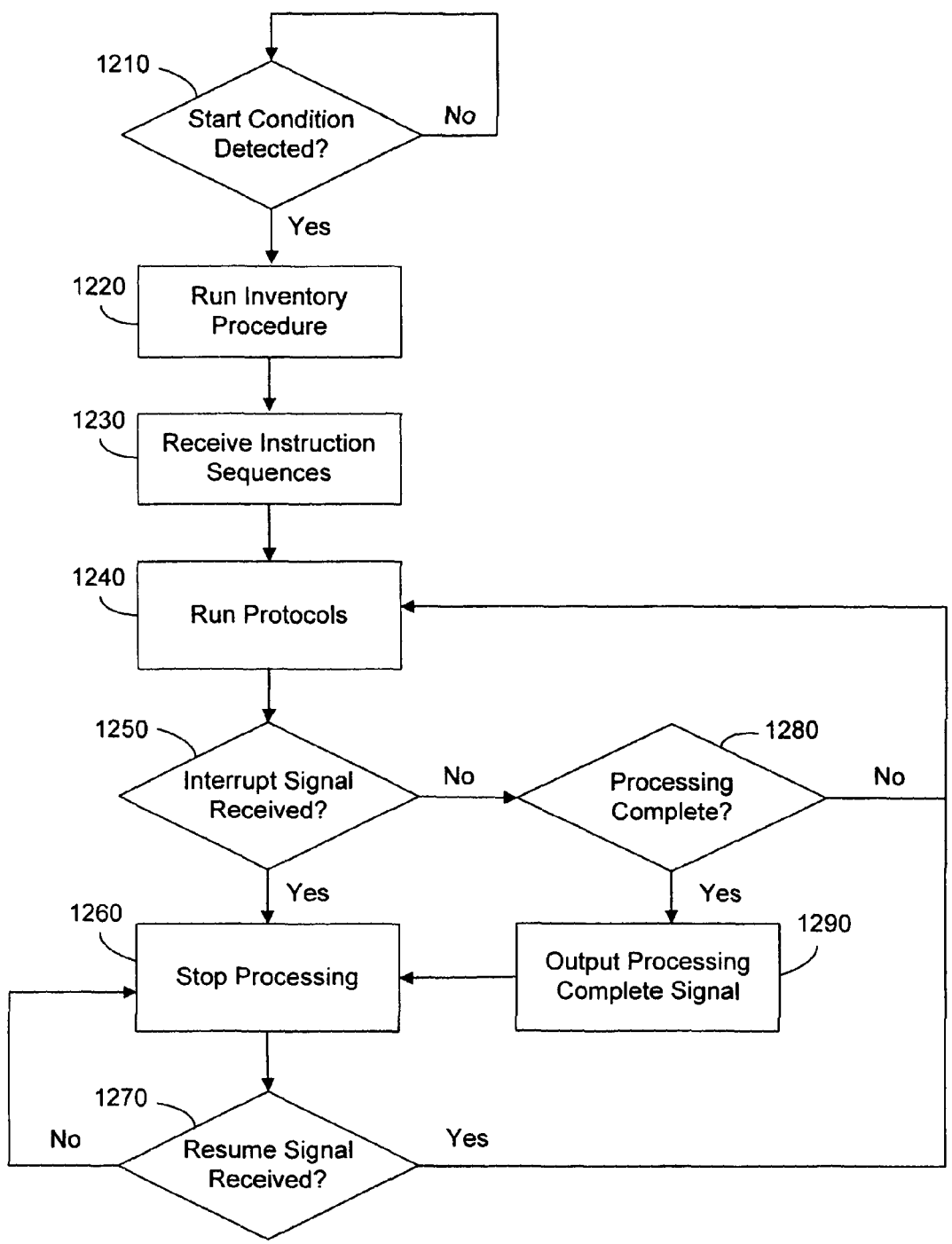
FIG. 12 is a flowchart depicting an initialization procedure in accordance with the present invention.

After changing the password, or if a password change request has not been received, the user may be presented with a main control display as illustrated diagrammatically as box 640 in FIG. 6. An initialization procedure may be run after the specimens are loaded into the stainer so that specimen and reagent information may be gathered by the system and presented in the main control display. An example of an initialization procedure in combination with processing protocols are shown in FIG. 12. The initialization procedure occurs after a start condition is detected as indicated by box 1210 and may include taking an inventory of the retaining trays and reagent cartridges and containers. A start condition may be, for example, closing the cover on the housing of a stainer included in the automated reagent dispensing system, receiving a start signal from a control computer, or any other condition. If a start condition is not detected, the automated reagent dispensing system may continually check whether a start condition is detected until a start condition is detected.

Figure 13:
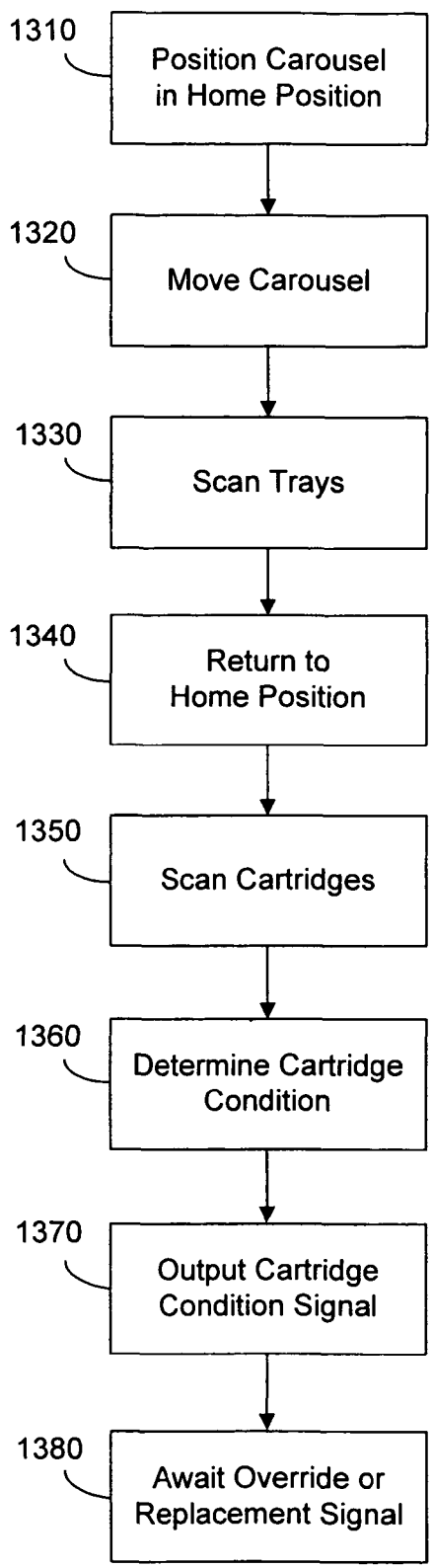
FIG. 13 is a flowchart depicting a scanning procedure in accordance with the present invention.

After detecting a start condition, an inventory procedure may be run as diagrammatically illustrated as box 1220. The inventory procedure may include the scanning procedure illustrated in FIG. 13. The scanning procedure scans all trays and cartridges provided in the automated reagent dispensing system to determine a status for the system. As illustrated diagrammatically as box 1310, a reagent carousel for the automated reagent dispensing system is positioned in a home position. The home position is preferably a zero (0), or start, position from which the carousel begins each scanning procedure. The start position may correspond to a location of the carousel with respect to the slides in addition to a rotational start position of the cartridges. For example, the start position may correspond to the position of the carousel shown in FIG. 2. The carousel moves by each tray as shown diagrammatically as box 1320. As described above, the carousel may include a scanner that scans an identifier associated with each tray as shown diagrammatically as box 1330. This enables the system to determine which trays include specimens. After scanning the tray identifiers, the carousel returns to the home position (box 1340).

Identifiers associated with reagent cartridges are then scanned as illustrated diagrammatically as box 1350. By scanning the reagent cartridges, the system may indicate the type and quantity of a reagent present in each reagent cartridge. A determination is made regarding a cartridge condition for each reagent cartridge (box 1360). The determination may indicate a particular type of reagent contained in the cartridge and that the quantity of reagent in the cartridge such as in percentage fill of the cartridge (e.g., cartridge is seventy-five (75) percent full).

Maintaining a history of the quantity of a reagent that has been dispensed may further assist in making the determination regarding the quantity of reagent that is present in the cartridge. For example, in an embodiment, a cartridge may have a one-hundred (100) milliliter capacity for reagent and in an embodiment each time reagent is dispensed from the cartridge using the automated reagent dispensing system, one (1) milliliter of reagent is dispensed. If the history indicates that reagent has been dispensed twenty-five (25) times from the cartridge, then seventy-five (75) milliliters (or seventy-five (75) percent) of the reagent remains in the cartridge. After determining the cartridge condition, a cartridge condition signal maybe output to provide the user with an indication regarding how much and what types of reagents are stored in the cartridges (box 1370). As an example of this, a number of dispenses is designated as a maximum for each cartridge. With each dispense a mechanical or software counter is incremented, and once the maximum number is reached or exceeded, a replace signal or other indicator is provided. In a further example, a cartridge depleted signal is provided which the system understands as requiring no further usage of the cartridge, and requiring replacement. Alternatively, the cartridge can continue being used, but a warning is provided, notifying an operator that a fresh cartridge should be installed. As a further example, the maximum number of dispenses for each cartridge is pre-programmed in a computer memory, or alternatively is noted on a readable (machine or human) indicator on a cartridge label. Different number of maximum dispenses can be set for different cartridges or different volume of dispensing chambers on particular cartridges.

If a determination is made that a cartridge is empty or that the cartridge contains an insufficient amount of reagent to perform a predetermined staining process, the automated reagent dispensing system may await an override or replacement signal as diagrammatically illustrated as box 1380. The override signal indicates that the user desires to continue with a staining process regardless of the cartridge conditions. The replacement signal indicates that one or more of the cartridges having an insufficient amount of reagent have been filled or replaced. In addition, the system may scan the bulk solution and waste containers to determine whether they require refilling, emptying or replacement.

Figure 14:
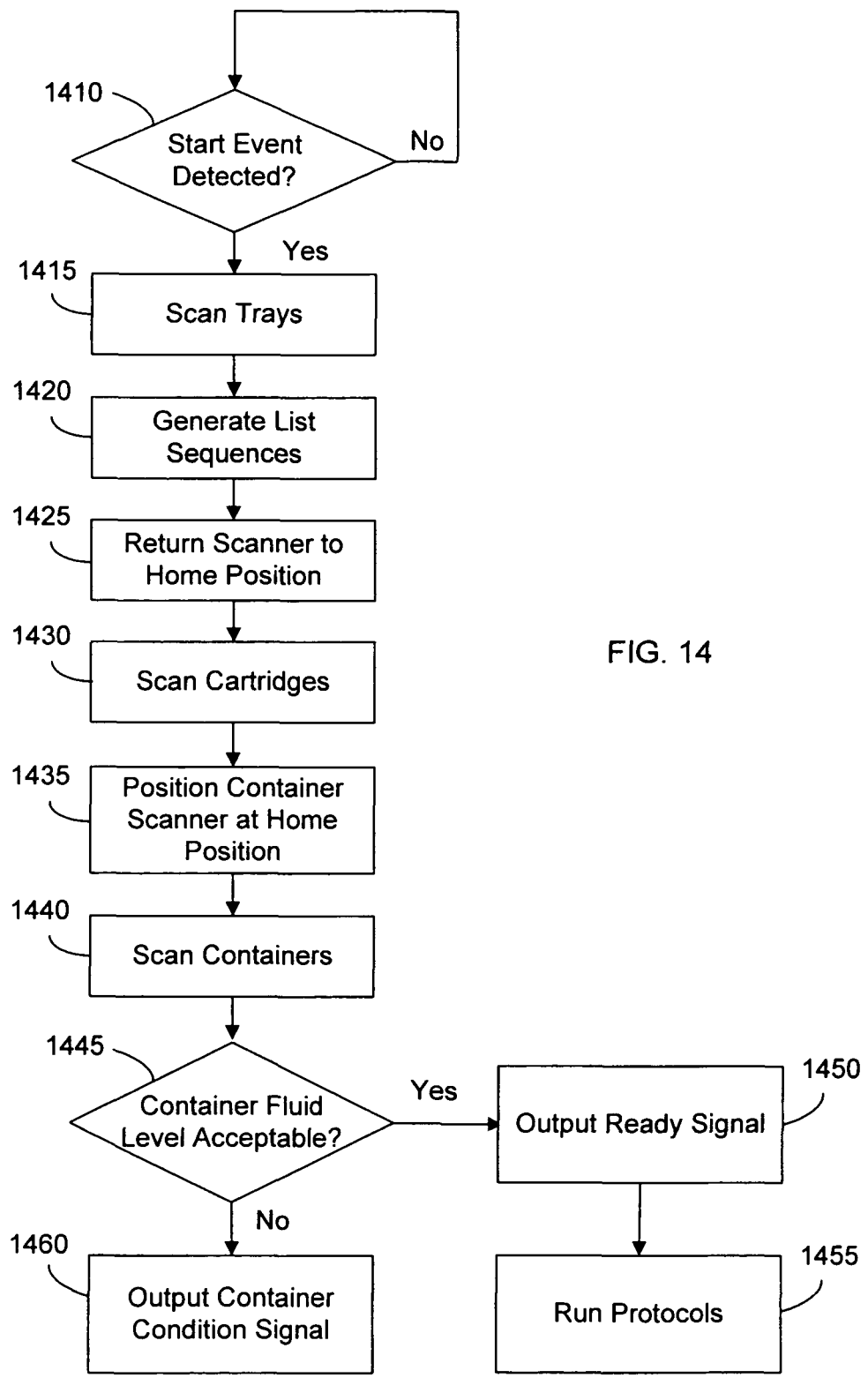
FIG. 14 is a flowchart depicting an inventory procedure in accordance with the present invention.

In another embodiment of an initialization process, shown in FIG. 14, an initial step of an initialization procedure, illustrated diagrammatically as box 1410, is to determine whether a start event (described above) has been detected. If a start event has not been detected, the automated reagent dispensing system may continually check whether a start event has been detected. After a start event has been detected, the automated reagent dispensing system may scan the trays (box 1415) to determine a status of the automated reagent dispensing system (described in further detail above). Based on information obtained during scanning of the trays, a list sequence may be generated as shown diagrammatically as box 1420.

A scanner of the automated reagent dispensing system is returned to a home position, provided the scanner is not already located at the home position, shown diagrammatically as box 1425. The scanner then scans the cartridges (box 1430). The cartridges are scanned to determine a number of cartridges present and what reagents are present in the cartridges. After scanning the cartridges, the scanner may be returned to the home position, illustrated diagrammatically as box 1435. The containers provided in the automated reagent dispensing system are then scanned to determine a number of containers and which reagents are present (box 1440).

Based on the scan of the containers, a determination is made regarding whether each of the containers has an acceptable fluid level, illustrated diagrammatically as box 1445. If a determination is made that the fluid levels in each of the containers is acceptable, a ready signal may be output to, for example, a controller of the automated reagent dispensing system (box 1450). The ready signal indicates that the automated reagent dispensing system is ready to operate and the staining protocols are run (box 1455).

If a determination is made that the fluid level in any of the containers is not acceptable, a container condition signal may be output as illustrated diagrammatically as box 1460. The automated reagent dispensing system may then await an override or replacement signal as described in further detail above with reference to FIG. 6.

The information that is gathered during the inventory procedures may be stored in one or more databases either locally or externally. The databases may be formatted through displays that allow the user to input and organize data. FIG. 15 illustrates a display 1500 that may be presented to a user to setup slide information tables. The display 1500 may include a name field 1510 that enables the user to assign a name to a slide information table and a description field 1520 that enables the user to input a description of the slide information table. For example, a table associating patient information with a particular slide may be created. In addition, a table associating physician information with a particular slide may be created. It should be appreciated that any information that would be useful to track may be recorded in a table, such as tissue type, dates of collection of a specimen and/or dates of performing steps in the processing protocols, etc. Selectable function keys 1530 may also be presented to enable the user to save slide information tables and exit the display 1500.

FIG. 16 illustrates a display 1600 that may be presented to a user to setup slide barcode format according to one embodiment of the present invention. The display 1600 may include a number field 1610 that indicates a number assigned to a slide barcode, a length field 1620 that enables the user to assign a length to the barcode, and a data format field 1630 that enables the user to assign a data format to the barcode. Selectable function keys 1640 may also be presented to enable the user to save slide barcode formats and exit the display 1600.

Figure 17:
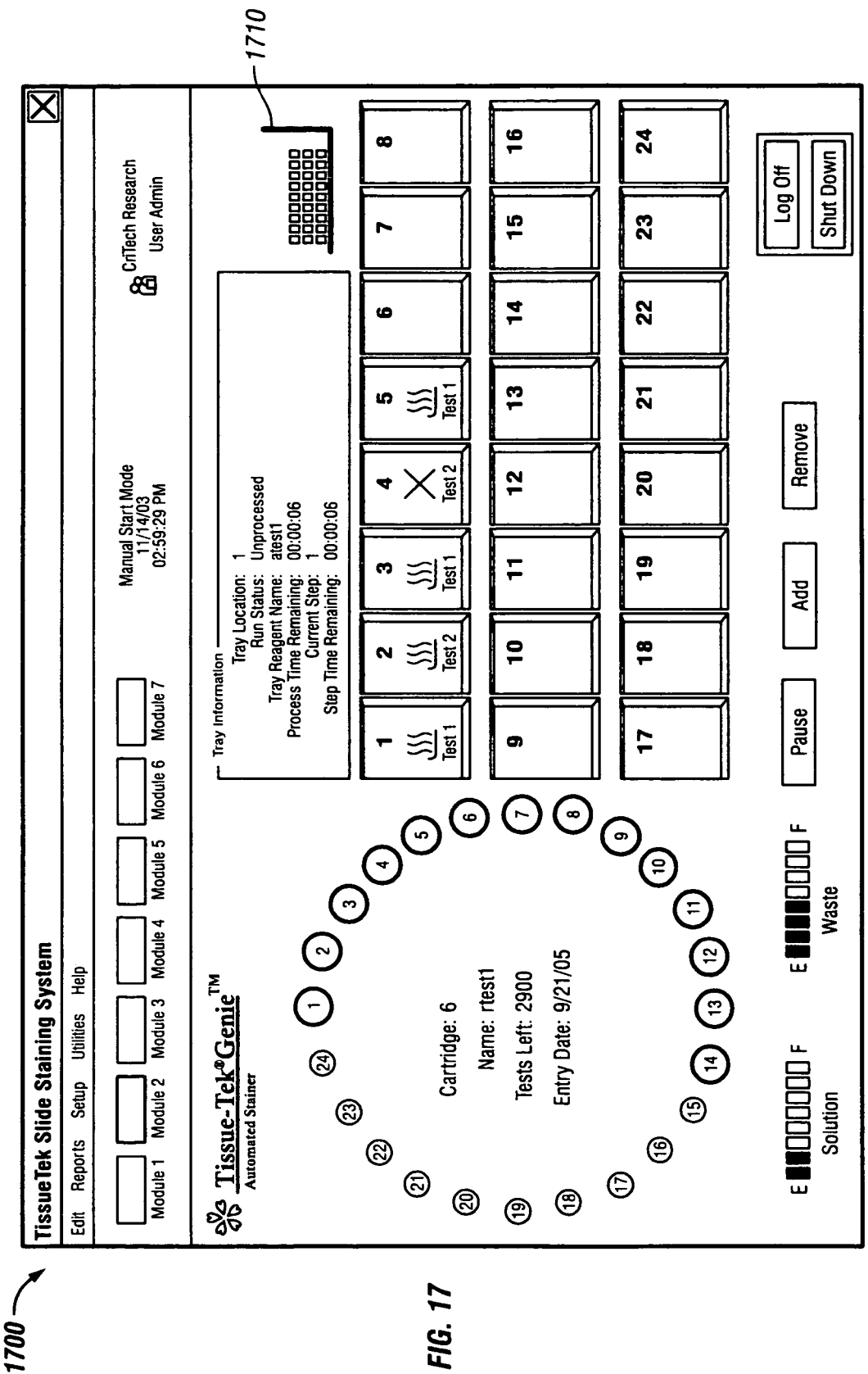
FIG. 17 is a display of a main control window in accordance with the present invention.
Figure 18:
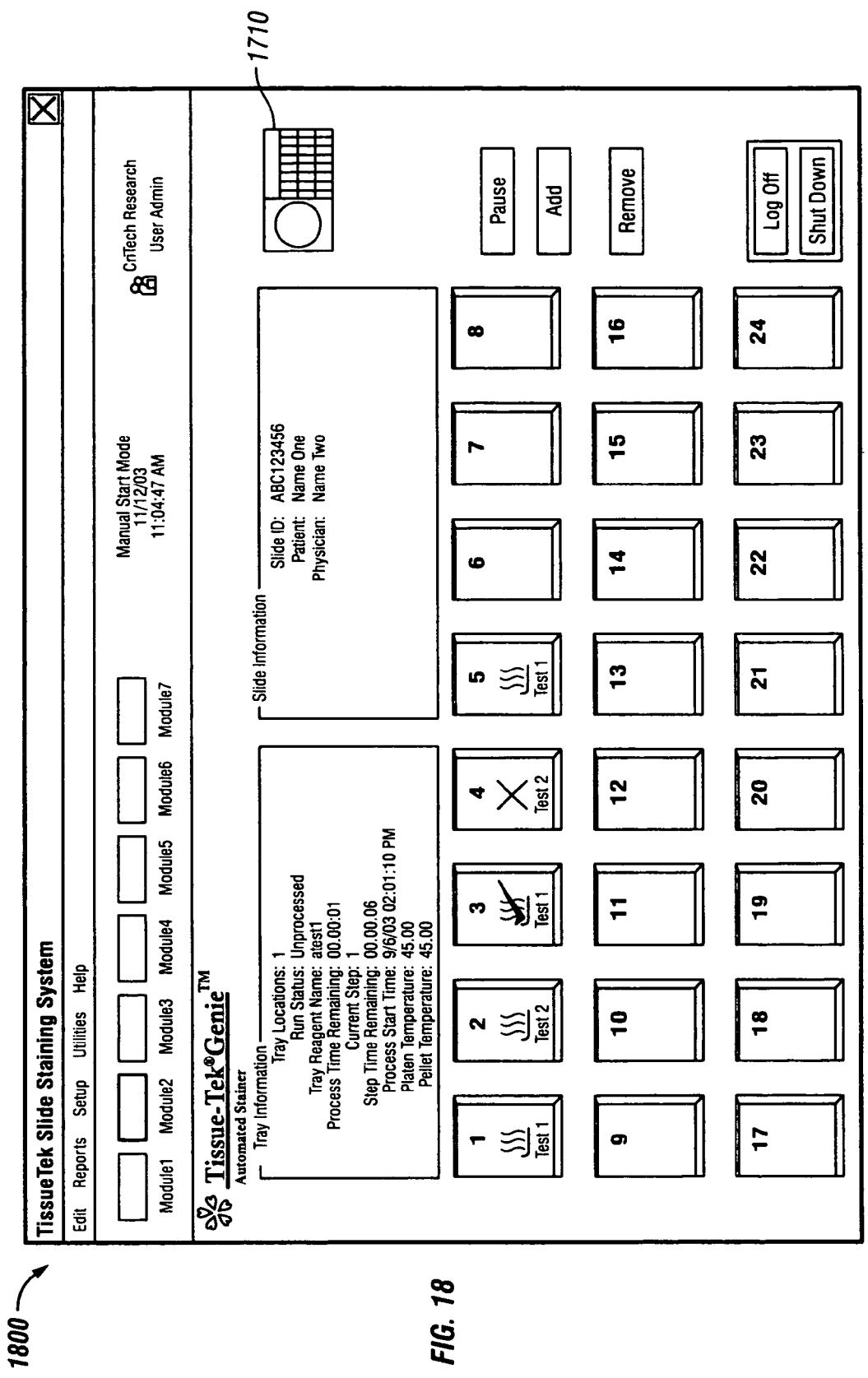
FIG. 18 is a display of a main control window in accordance with the present invention.

As mentioned above, after the system has run the inventory procedures it may display the gathered information through a main control display. Examples of main control displays 1700, 1800 are shown in FIGS. 17 and 18, respectively. The main control window preferably displays a substantial graphical replica of the automated reagent dispensing system. For example, display 1700 includes a circular graphical representation of cartridges and an array of retaining trays. Display 1800 also provides an illustration of the capacities of bulk solution waste bottles. Alternatively, main control display 1800 may only display retaining trays included in the automated reagent dispensing system, as shown in FIG. 18. It shall be appreciated that both displays may be available and a user may select the preferred display using a button 1710, toggle switch or other selector included on the displays.

The main control display preferably enables the user to view which trays and cartridges are in use, an amount of reagent available, an amount of waste collected, pause operation of the automated reagent dispensing system, add/remove trays/cartridges from operation, and other desired functions. The main control display preferably also provides a status of a staining protocol being run or the last staining protocol run. Additional information such as tray and/or slide information obtained by scanning associated identifiers may also be displayed.

Upon completion of the inventory procedure, the automated reagent dispensing system may receive instruction sequences from a controller as diagrammatically illustrated as box 1130. The instruction sequences define one or more staining processes to be applied to the specimens contained on the slides, or in the containers, provided on the retaining trays. The staining processes, as described above, identify the type and quantity of each reagent that will be applied to each specimen over a specified period.

During the process of using the system shown in FIG. 6, a determination is made regarding whether a request to run a program has been received, as illustrated diagrammatically as box 650. A user may make such a request through a main control display such as those illustrated in FIGS. 17 and 18. Using the main control display, the user may request that one or more pre-programmed routines and/or manual operations be run.

Figure 19:
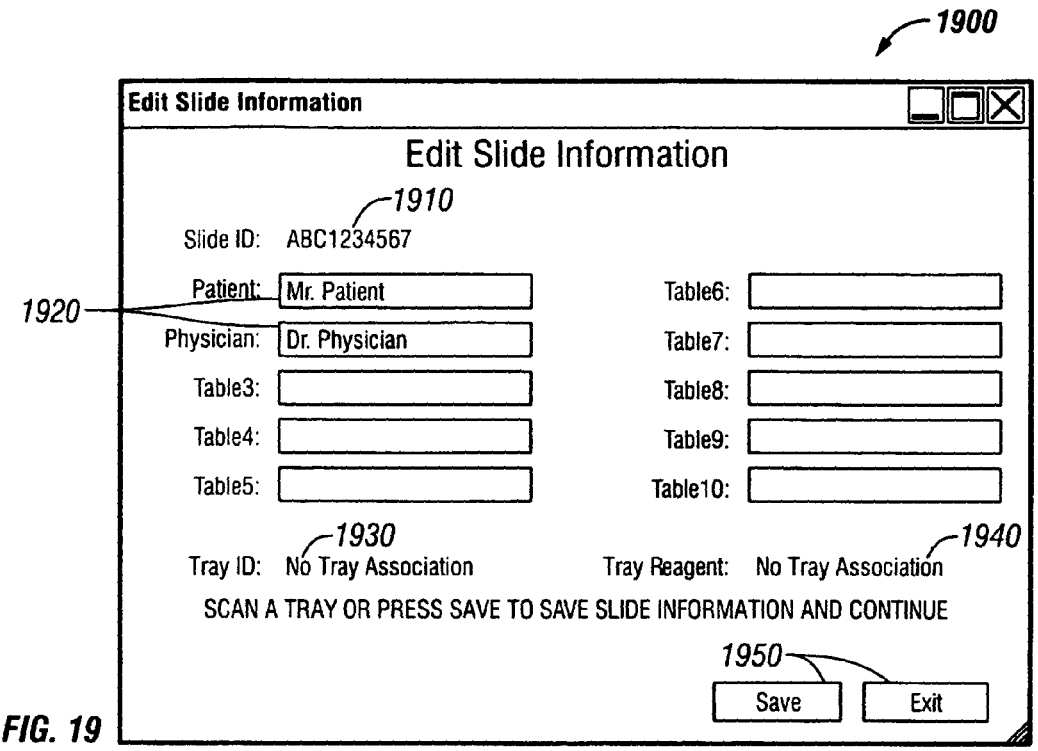
FIG. 19 is a display associated with editing slide information in accordance with the present invention.

After the slide information is scanned and displayed through the main control display. The user may be presented with displays that allow them to manually edit the gathered information. FIG. 19 is an illustration of a display 1900 that may be presented to enable the user to edit slide information according to one embodiment of the present invention. The display 1900 may include a slide identifier 1910. The slide identifier 1910 may be used to display a name or other identification for a particular slide. The display 1900 may also include one or more input fields 1920. The input fields 1920 enable the user to edit/input information regarding a particular slide. The input fields 1920 may include, for example, patient, physician, and table information. The display 1900 may also include a tray identifier 1930 and tray reagent identifier 1940 to identify a tray associated with the particular slide. Function keys 1950 may also be provided to enable the user to, for example, save information entered or exit the display 1900.

Figure 20:
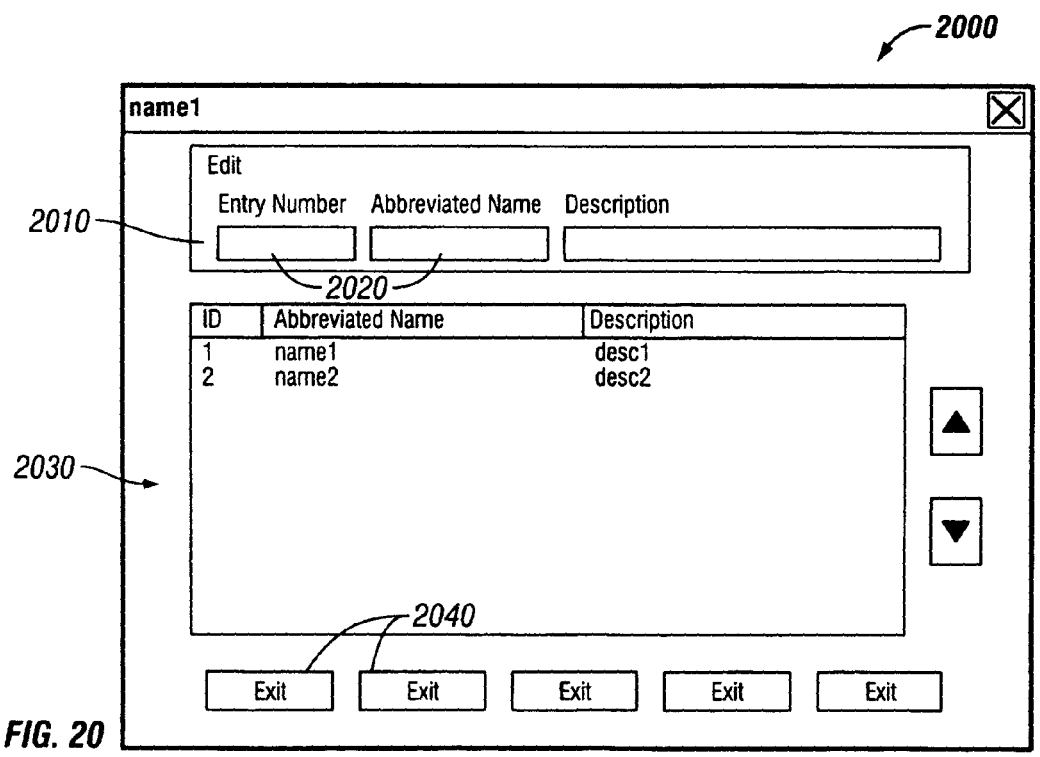
FIG. 20 is a display associated with editing slide information tables accordance with the present invention.

FIG. 20 illustrates a display 2000 that may be presented to a user to edit slide information tables according to an embodiment of the present invention. The display 2000 may include an edit section 2010 that includes one or more edit fields 2020. The edit fields 2020 may enable the user to edit slide information such as, for example, entry number, abbreviated name, and description. An information section 2030 may also be presented that identifies an entry number, abbreviated name, and description for one or more slides. One or more selectable function keys 2040 may be used to perform various functions. For example, the user may add, edit, delete or print a slide information table using the function keys 2040 or exit the display 2000.

After receiving a run program request, the automated reagent dispensing system runs the program request as illustrated diagrammatically as box 660 and as further detailed in FIG. 12. As shown in FIG. 12, upon receiving the instruction sequences (step 1230), staining protocols are run by the automated reagent dispensing system as diagrammatically illustrated as box 1240.

While the staining protocols are run, the automated reagent dispensing system determines whether an interrupt signal has been received, as indicated by box 1250. An interrupt signal may be caused by, for example, opening of the cover of the automated reagent dispensing system, a command received from the controller or other event. If an interrupt signal has been received, the automated reagent dispensing system stops processing as diagrammatically illustrated as box 1260. A determination is then made regarding whether a resume processing signal has been received (box 1270). If a resume processing signal has not been received, the automated reagent dispensing system continues to stall processing (box 1260). If a resume processing signal has been received, however, the automated reagent dispensing system continues to run the staining protocols as diagrammatically shown by box 1240.

If an interrupt signal has not been received, a determination is made whether processing has been completed, as indicated by box 1280. Processing may include completing all staining protocols for each of the tissue samples provided in the automated reagent dispensing system.

If the processing has not been completed, the automated reagent dispensing system continues to run the staining protocols as diagrammatically shown as box 1240. If a determination is made that processing is complete, a processing complete signal may be output to a controller (box 1290) and the automated reagent dispensing system stops processing as diagrammatically illustrated as box 1260.

Figure 21:
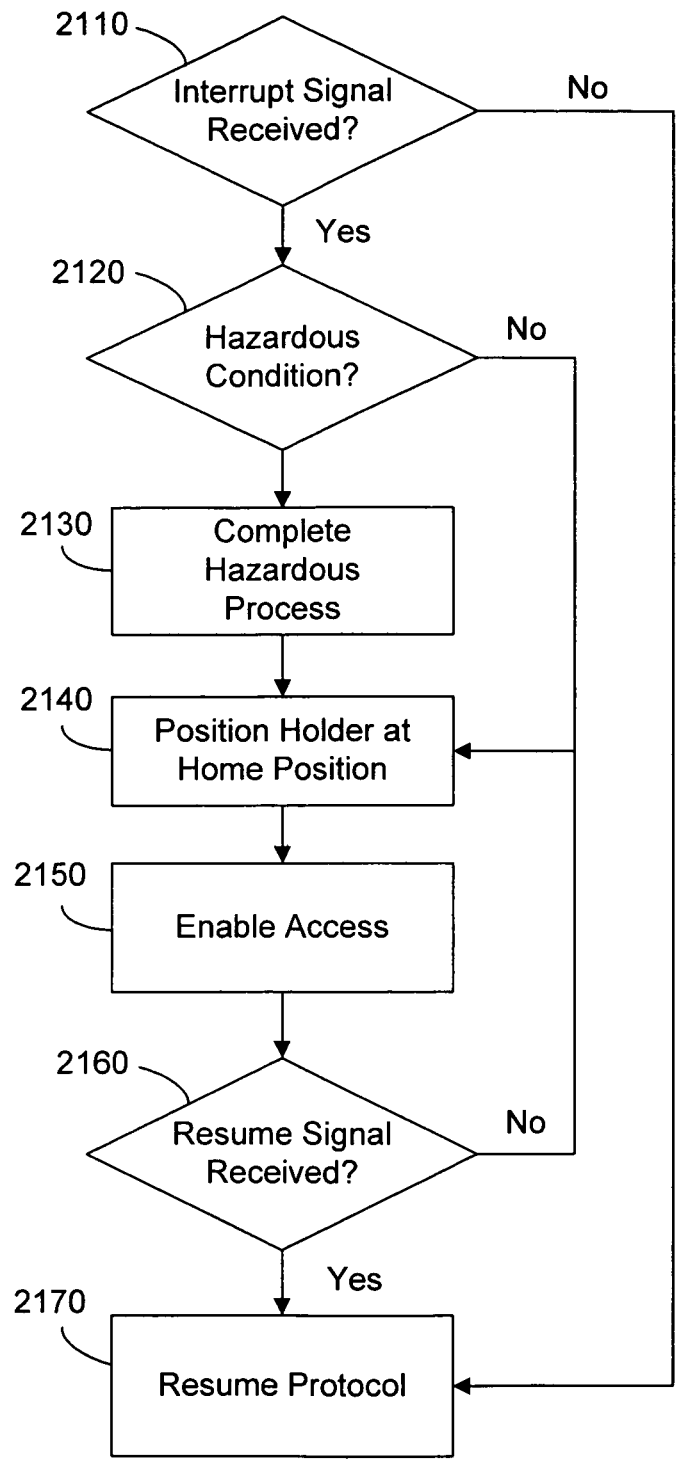
FIG. 21 is a flowchart depicting an interrupt event procedure in accordance with the present invention.
Figure 22:
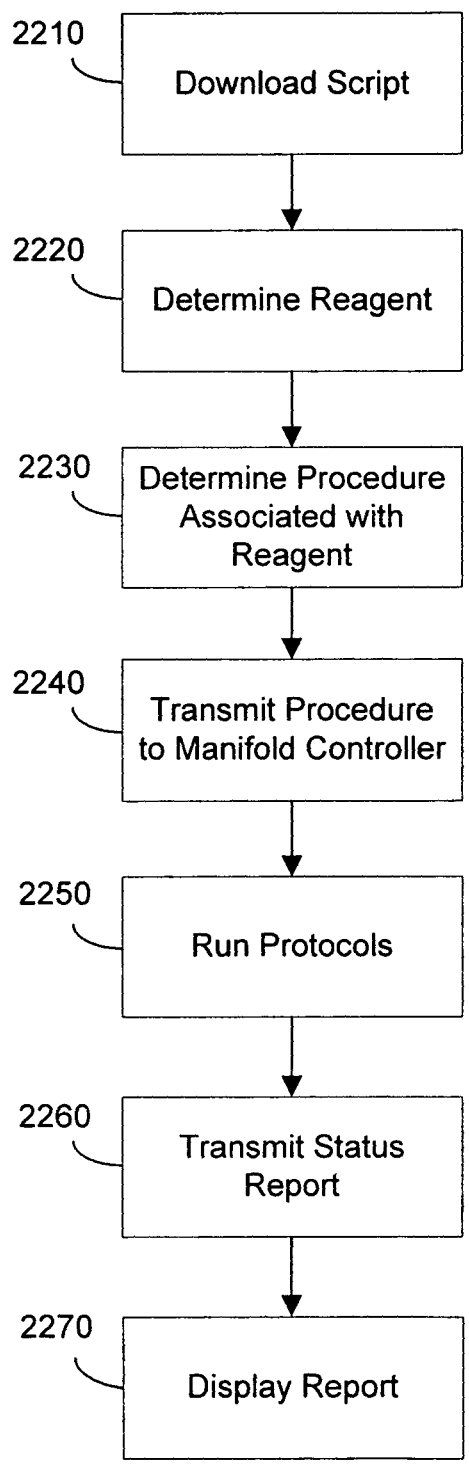
FIG. 22 is a flowchart depicting an overall procedure in accordance with the present invention.

FIG. 21 illustrates in further detail an interrupt event procedure according to an embodiment of the present invention. A determination is made regarding whether an interrupt signal has been received (shown diagrammatically as box 2110). If an interrupt signal has been received, a determination is made regarding whether a hazardous condition exists as illustrated diagrammatically as box 2120. A hazardous condition may be, for example, that a reagent having a poisonous gas associated therewith has just been dispensed. Should a user come in contact with the poisonous gas, the user may experience illness. If a determination is made that a hazardous condition exists, the hazardous process may be completed as illustrated diagrammatically as box 2130. A carousel or other reagent cartridge holder is then moved to a home position as shown diagrammatically as box 2140. The user is enabled access to an interior portion of the automated reagent dispensing system (box 2150). The user may be enabled access by, for example, unlocking a lock or other mechanism that prevents the cover of the automated reagent dispensing system from being opened.

The automated reagent dispensing system then determines whether a resume signal has been received as shown diagrammatically as box 2160. A resume signal may be caused by closing the cover or a command output by a controller as described above. If a resume signal has not been received, the automated reagent dispensing system continues to position the cartridge carousel or holder at a home position (box 2140). If, however, a resume signal has been received, the automated reagent dispensing system resumes the staining protocol(s) as illustrated diagrammatically as box 2170.

In another embodiment, the process may be fully automated. FIG. 11 illustrates diagrammatically a fully automated procedure that may be performed by an automated reagent dispensing system according to an embodiment of the invention. As an initial step, a script or processing program that defines the steps required to perform an automated staining procedure is downloaded from a controller. This step is illustrated diagrammatically as box 2210. The downloaded script may be based on information obtained by scanning an identifier associated with the slide as described above. A primary reagent to be applied to the slide is determined as shown diagrammatically as box 2220. The primary reagent information may also be obtained from the identifier associated with the slide. One or more staining protocols to be applied to a particular slide are determined based on the primary reagent identified as illustrated diagrammatically as box 2230. The staining protocol(s) determined are then transmitted to a manifold controller as shown diagrammatically as box 2240. The manifold controller controls the carousel on which the cartridges are mounted and the dispensing of reagents from the cartridges. The automated reagent dispensing system then runs the protocols, as diagrammatically illustrated as box 2250.

One or more status reports may be transmitted from the automated reagent dispensing system to, for example, a central controller such as a personal computer or other controller, as illustrated by box 2260. Status reports may be transmitted automatically, for example, on a periodic basis, or manually upon request by a user using the central controller. Upon receiving the status reports, the central controller may display the reports as diagrammatically illustrated by box 2270.

Figure 23:
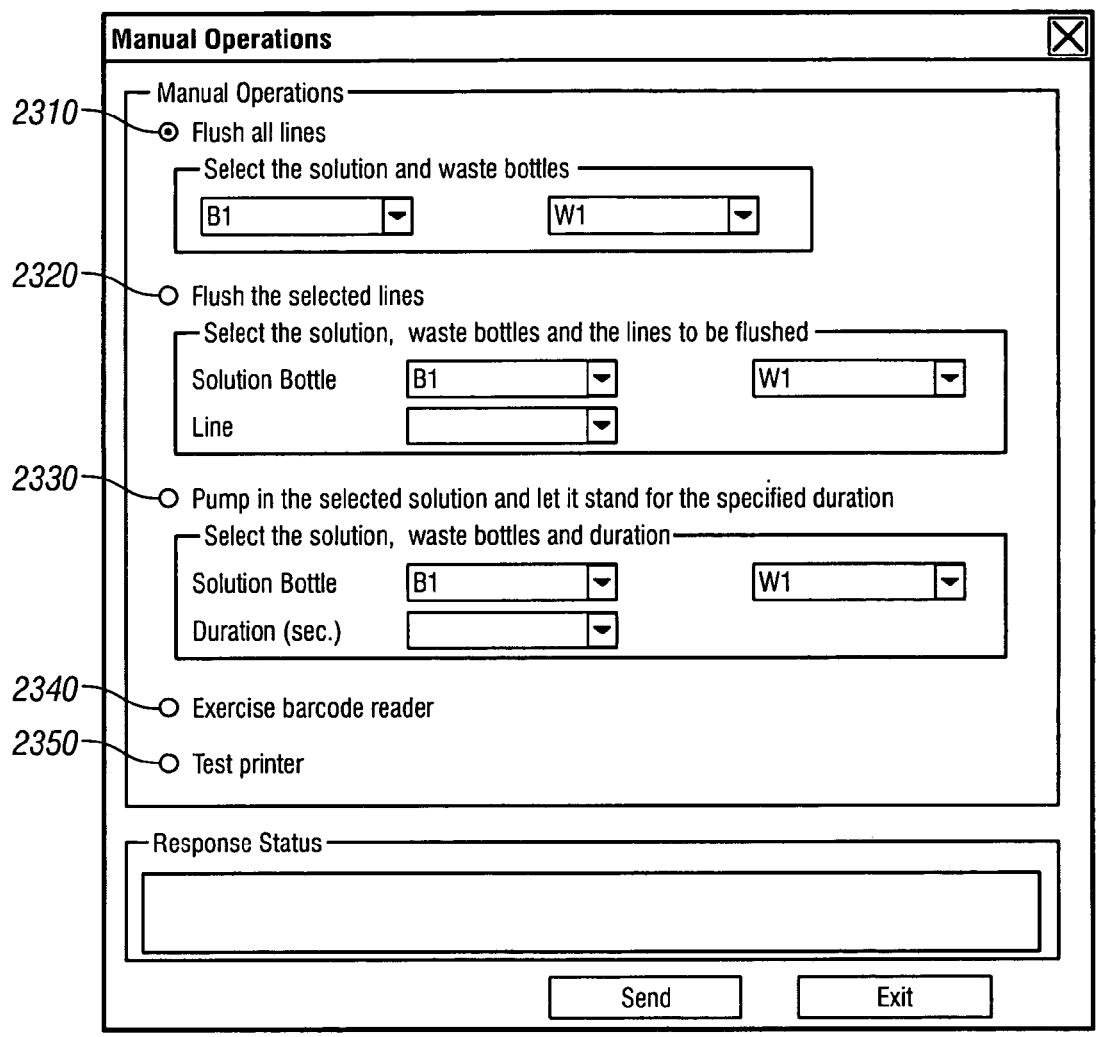
FIG. 23 is a display associated with manual operations in accordance with the present invention.

Referring back to FIG. 6, a user may elect to create or modify program requests that are received, as indicated by box 670. If the user requests that one or more manual operations be run, the system enables creating or modifying operations, indicated by box 680 and the user may be presented with a manual operations display as shown in FIG. 23. Manual operations that the user may initiate may include, for example, flush all lines 2310, flush selected lines 2320, pump selected solution 2330, exercise barcode reader 2340, test printer 2350, etc. The display may also present function keys 2360 that allow the user to send a manual operation request or to exit the screen. After all operation requests are received by the system, the user may elect that the system display the requests that were received as indicated by boxes 690 and 695 of FIG. 6.

Methods of processing tissue samples in accordance with the present invention may include various steps. In an embodiment, a method of processing a tissue sample using a slide retaining tray in accordance with the present invention is shown in to FIG. 24. As illustrated diagrammatically as box 2400, the initial step involves selecting a slide retaining tray based upon the type of gel or reagent(s) contained therein. Of course, the type of gel (i.e. reagent) contained within an individual tray is dependent upon the type of test to be performed on a tissue sample. In other words, the initial step of selecting a slide retaining tray may include the step of determining the type of test to be performed on the tissue sample.

As illustrated diagrammatically as box 2410, the next step involves optionally swiping a bar code on a slide or tray. It should be noted that such a step is not necessary, and alternatively, no slide data may be read or input, or slide data may be input manually. As illustrated diagrammatically as box 2420, the next step involves pulling the seal from the tray, thereby exposing the recess and reagent therein. Referring to box 2430, the next step involves positioning the slide on the tray. Preferably, the slide is positioned such that the tissue sample is disposed between the slide and a platen. As illustrated diagrammatically as box 2440, the next step involves optionally positioning the slide retaining tray on a spring loaded heating/cooling pad.

As illustrated diagrammatically as box 2450, the next step involves liquefying a reagent matrix (i.e., the gel). This step may include the step of heating the matrix to form a melt. Alternatively, the matrix may be soluble in a solvent, which is added to the recess to dissolve it. Thus, the step of liquefying the matrix alternatively may include the step of dissolving the gel using a solvent. Referring to box 2460, the next step involves flowing the liquefied reagent matrix over a drip surface into a gap, or reaction chamber, between the platen and the slide. This step may be accomplished with the assistance of gravity.

Referring to box 2470, the next step optionally involves flushing the gap with wash fluids to prepare the tissue sample for subsequent tissue processing steps. As illustrated diagrammatically as box 2480, the next step involves optionally dispensing non-primary reagents from the fluid dispensing apparatus onto the drip surface of the retaining tray. Finally, referring to box 2490, the next step involves drawing waste and excess fluid through a fluid return conduit into a waste reservoir.

Figure 24:
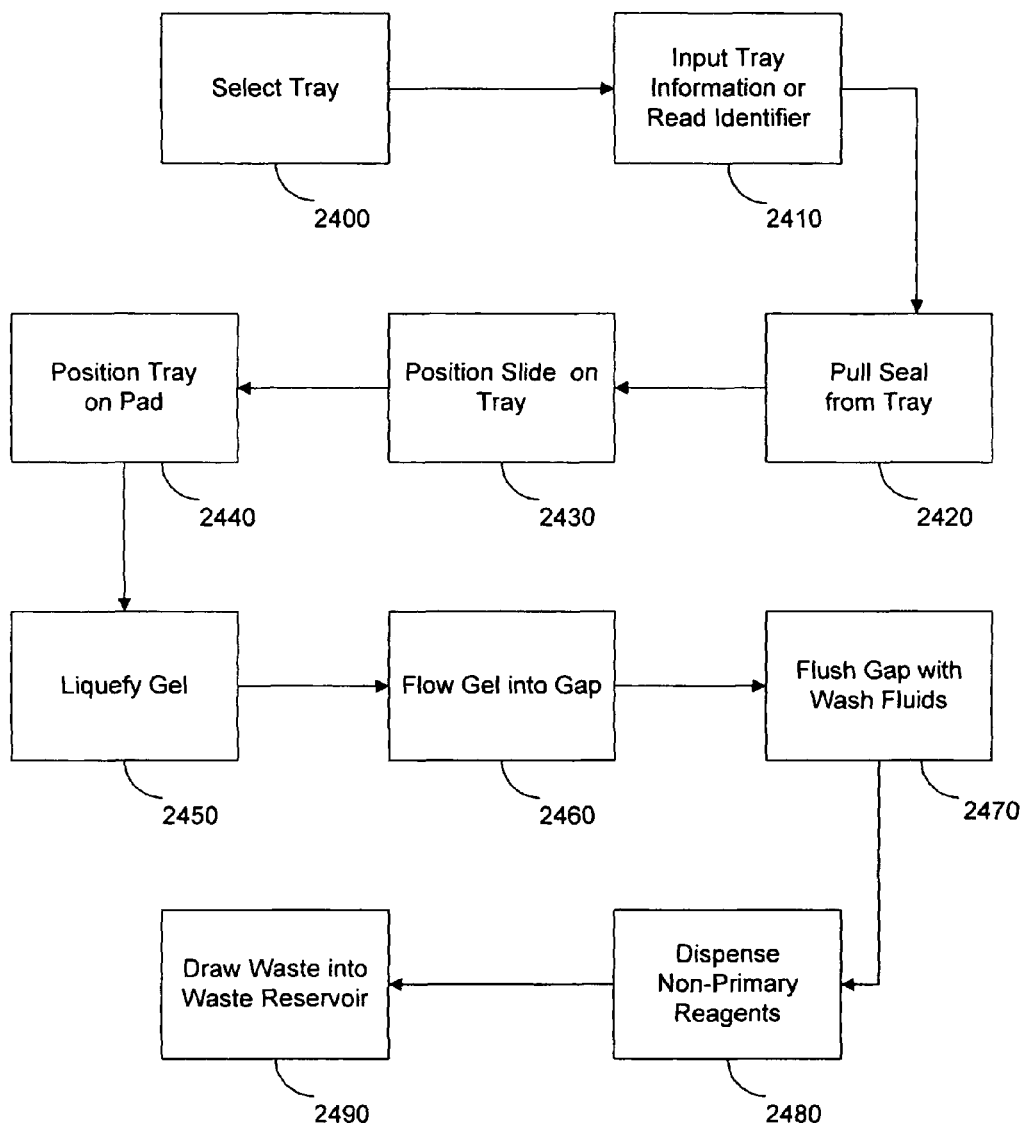
FIG. 24 is a flowchart depicting a method of using a slide retaining tray in accordance with the present invention.

With further reference to FIG. 24, the steps illustrated by boxes 2410, 2420, and 2430 may be performed in any order without departing from the scope of the present invention. Additionally, the step of swiping the bar code on the tray (box 2410) can optionally be performed after the step of positioning the slide on the tray (box 2430), and either of these steps can be eliminated. Further, the step of pulling the seal from the tray (box 2420) can be performed at any time after the initial step of selecting a tray based upon the type of gel contained therein (box 2400).

Figure 25:
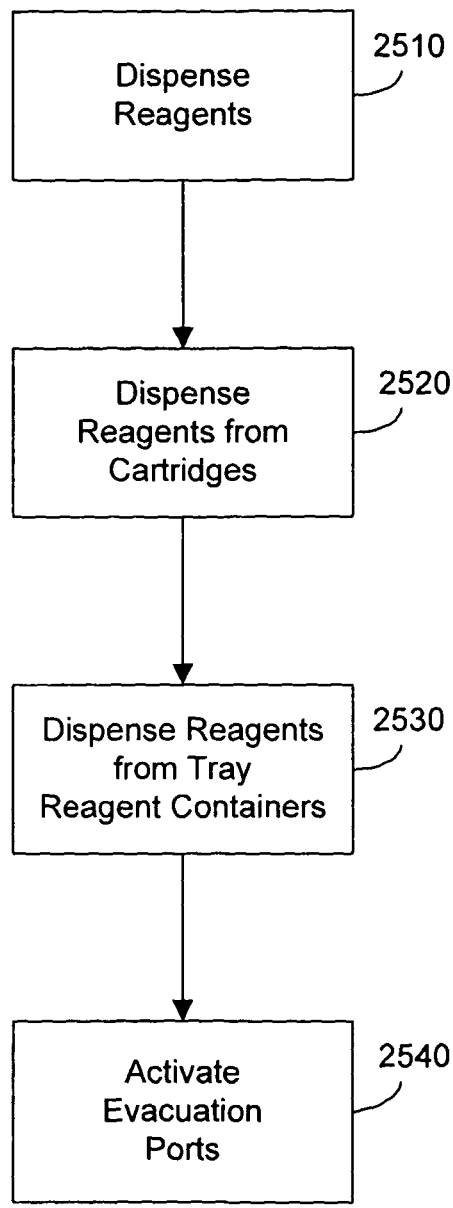
FIG. 25 is a flowchart depicting run protocols sub-steps in accordance with the present invention.
Figure 27:
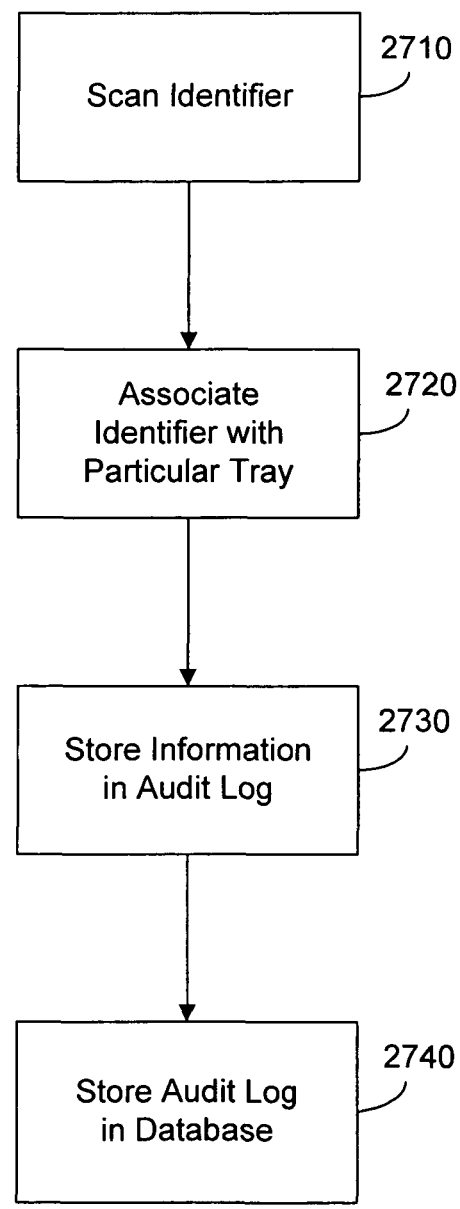
FIG. 27 is a flowchart depicting an audit logging procedure in accordance with the present invention.

FIG. 25 illustrates another embodiment of sub-steps associated with a processing procedure. According to the embodiment shown in FIG. 25, the processing procedure includes dispensing reagents, as shown diagrammatically as box 2510. This may include, for example, dispensing reagents from a bulk container to a reagent cartridge. The bulk containers may be used to supply the cartridges with additional reagent. The bulk containers may be operated manually such that user intervention is required to transfer the reagent from the bulk container to the cartridge. This may be done, for example, by operating a switch or other mechanism that causes the reagent to travel from the bulk container, through a supply line or other conduit, to the cartridge. Alternatively, the automated reagent dispensing system may automatically fill the cartridge. This may be performed after the scanning procedure described above with respect to the initialization procedures. For example, the scanning procedure may identify one or more cartridges that require reagent through a screen such as that shown in FIG. 26. The automated reagent dispensing system may initiate filling of the cartridge(s) by causing reagent from an appropriate bulk container to travel to the cartridge(s). This maybe performed using a pump or other known mechanism.

The processing procedure also includes dispensing reagents from the cartridges as illustrated diagrammatically as box 2520. The reagent may be dispensed from the cartridge using, for example, a pump. The cartridges may be provided with a pump that is actuated by a solenoid. If a particular reagent is required to be dispensed, the automated reagent dispensing system actuates the solenoid associated with that cartridge by transmitting a signal to the solenoid. The solenoid pushes the pump and causes a predetermined amount of reagent to be dispensed from the cartridge. Preferably, the reagent is dispensed at desired times and according to a staining protocol.

The automated reagent dispensing system may also dispense reagents from tray reagent containers, or recesses, as shown diagrammatically as box 2530.

Upon completion of a processing procedure, evacuation ports associated with the trays may be activated as illustrated diagrammatically as box 2540. The evacuation ports may be, for example, holes provided in the trays. A vacuum may be applied to the tray that causes reagent located on the tray to be sucked into a waste conduit. According to an embodiment of the present invention, the waste may be divided into hazardous and non-hazardous waste with each going into a respective waste container.

The system may also allow for an audit logging procedure to be performed, as shown in FIG. 12. In an embodiment, the audit logging procedure may begin by scanning or otherwise obtaining information from an identifier provided on a slide as diagrammatically illustrated as box 2710. The identifier may be a bar code or other identifier as described above. Based on information obtained from scanning the identifier, the slide having the identifier may be associated with a particular tray, as indicated by box 2720. Various pieces of information may be stored and related to that tray in an audit log, as indicated by box 2730. For example, a record of what processes were run at what time and for which patient may be maintained based on the slide, tray, and processing protocol information. The audit log may be stored in a database as shown diagrammatically as box 2740.

Figure 28:
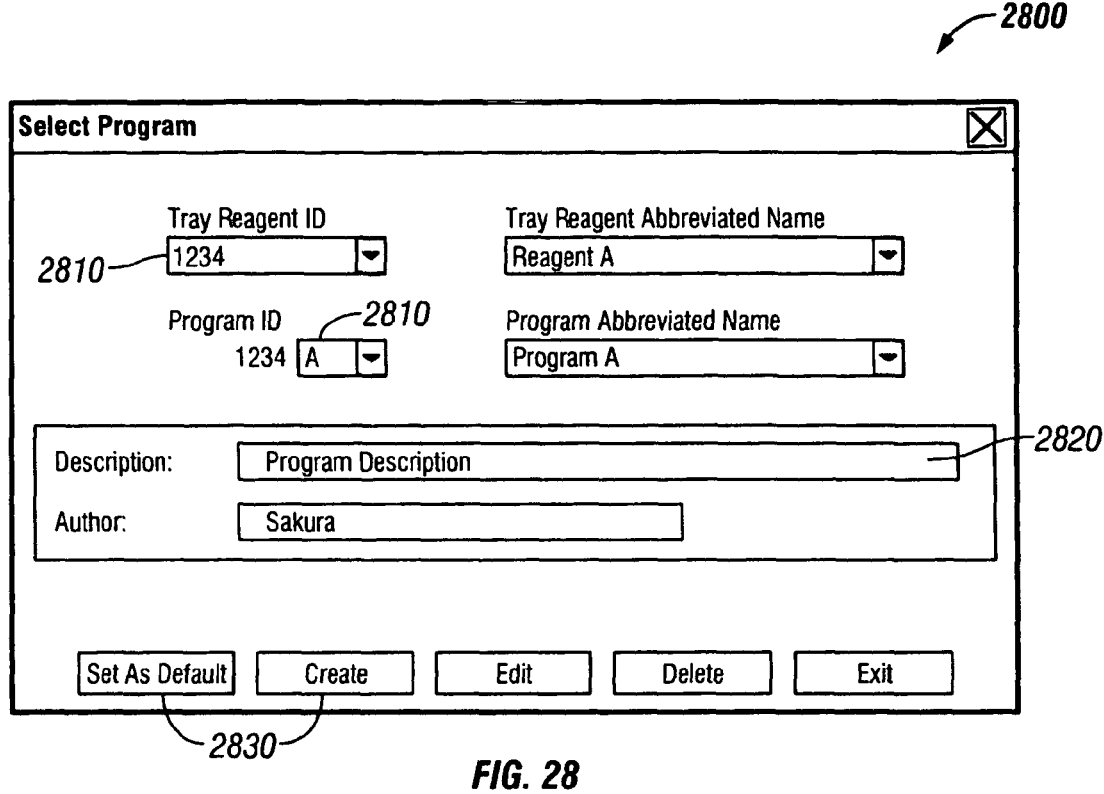
FIG. 28 is a display associated with selecting a program in accordance with the present invention.

Referring to FIGS. 28-64, various optional screens that may be presented to a user throughout the use of the system are described below. FIG. 28 is an illustration of a display 2800 that may be presented to enable the user to select a program according to an embodiment of the present invention. The display 2800 may include one or more selectable fields 2810. The selectable fields 2810 may include information relating to, for example, tray reagent identifiers, tray reagent abbreviated names, program identifiers, and program abbreviated names. The selectable fields 2810 may enable the user to select a particular program using the program identifier or the program abbreviated name or a program associated with a particular tray using the tray reagent identifier or the tray reagent abbreviated name. Upon selecting a program, information relating to the program may be presented in an information section 2820. The information section 2820 may include, for example, a program description and name of the author of the program. Other information may also be presented. The display 2800 may also include one or more selectable function keys 2830. The function keys 2830 may be used to, for example, create a new program, set a particular program as a default program, edit/delete a particular program, and exit the display 2800.

Figure 29:
FIG. 29 is a display associated with creating/editing a program in accordance with the present invention.

FIG. 29 illustrates a display 2900 that may be presented to enable a user to create/edit a program according to one embodiment of the present invention. The display 2900 may include a program information section 2910 that provides information regarding the program. The information may include, for example, a tray reagent identifier, tray reagent name, program identifier, program abbreviated name, program full name, author, editor, program description, creation date, and last modified date. The display 2900 may also include a macro section 2920. The macro section 2920 may include a macro identifier and a macro name associated with the program being created or edited. The macro section 2920 may also include a selectable edit macro function that enables the associated macro to be edited.

The display 2900 may also include a number of cycles section 2930, variability section 2940, and a hold time section 2950. The number of cycles section 2930 enables the user to indicate a minimum, maximum, and/or default number of cycles for the program to perform. The variability section 2940 enables the user to indicate a minimum, maximum, and/or default number for variability within the program. The hold time section 2950 enables the user to indicate a minimum, maximum, and/or default holding time for the program. The holding time may be indicated in seconds, minutes, hours or any other increment. The macro, number of cycles, variability, and hold time sections 2920, 2930, 2940, and 2950, respectively, may each have function keys 2960 associated therewith. The function keys 2960 may enable the user to add/edit/clear all/delete/undo information input into one or more of the macro, number of cycles, variability, and hold time sections 2920, 2930, 2940, and 2950, respectively.

The display 2900 may also include an information section 2970 and program type section 2980. The information section 2970 may include information relating to the program. The information may include, for example, step, function, reagent, hold time, platen temperature, and variability. The program type section 2980 may enable the user to select a particular program to run. The user may elect to use a particular program as the default program or allow the user to select a program during worklist development.

Figure 30:
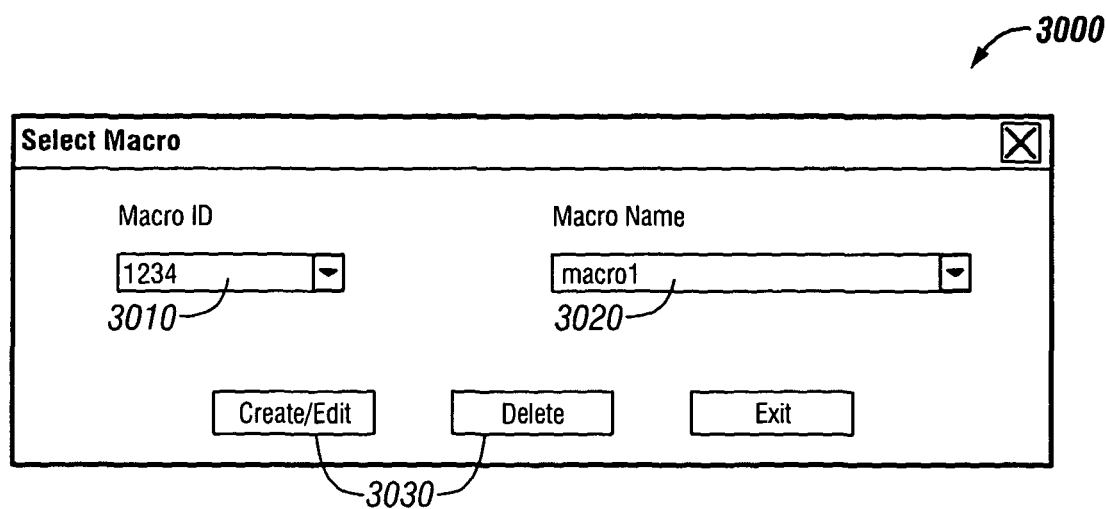
FIG. 30 is a display associated with selecting a macro in accordance with the present invention.

FIG. 30 illustrates a display 3000 that may be presented to a user to select a macro according to one embodiment of the present invention. The display 3000 may include an identifier field 3010 and a name field 3020 that indicates an identifier and a name for a particular macro. One or more selectable function keys 3030 may be used to perform various functions. For example, the user may create, edit or delete a macro using the function keys 3030 or exit the display 3000.

FIG. 31 illustrates a display 3100 that may be presented to a user to create/edit a macro according to one embodiment of the invention. The display 3100 may include a plurality of data fields 3110 that enables the user to input or edit information regarding a particular macro. The data fields 3110 may include, for example, macro identifier, macro name, revision, reagent A, reagent B, waste bottle identifier, minimum cycles, maximum cycles, default cycles, variability, emergency substitution solution name, emergency substitution solution temperature, extended incubation, minimum hold time, maximum hold time, default hold times, minimum hold temperature, maximum hold temperature, and default hold temperature.

Data fields 3110 may also be provided for each reagent associated with the macro. Data fields 3110 regarding reagent information may provide information pertaining to cartridge reagent identifier, cartridge reagent abbreviated name, bulk solution identifier and bulk solution abbreviated name. Other information may also be provided in data fields 3110 such as, for example, step sequence number, action, total units, platen temperature, pellet recess temperature, cycle step, criticality factor, and time.

An information section 3120 may be provided that provides additional information regarding one or more of the data fields 3110. Selectable function keys 3130 may also be presented to enable the user to create/edit/delete/save a particular macro, undo/clear information input, and exit the display 3100.

Figure 32:
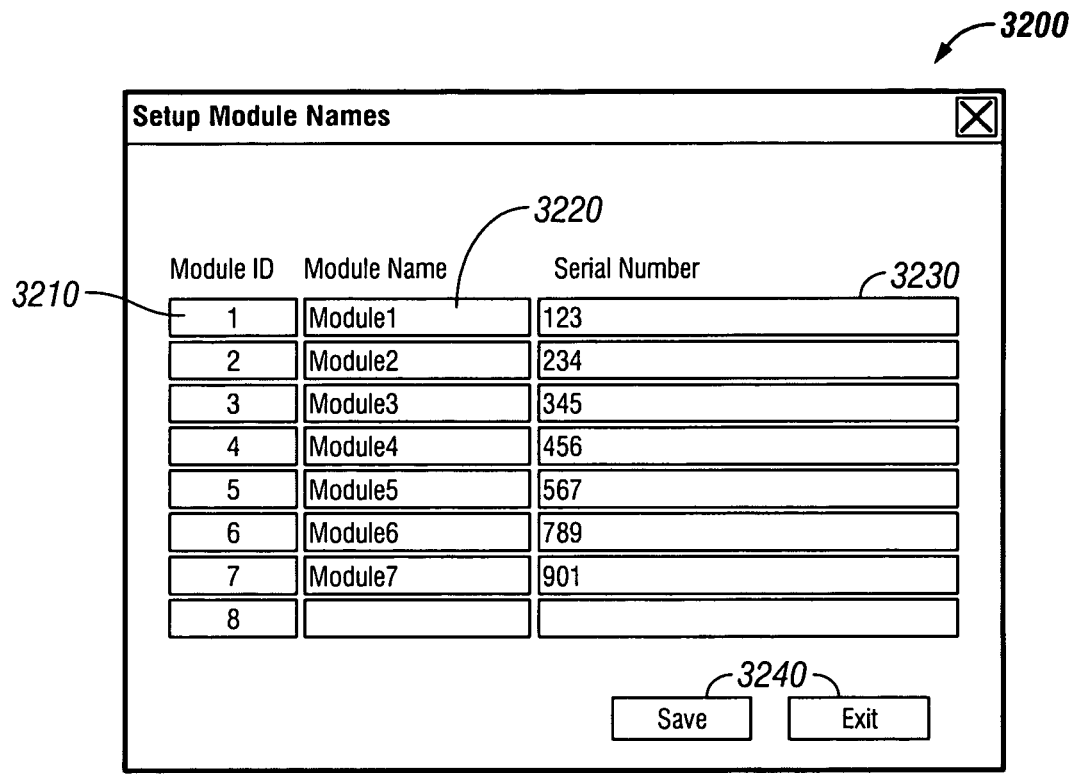
FIG. 32 is a display associated with module information setup in accordance with the present invention.

FIG. 32 illustrates a display 3200 that may be presented to a user to setup module names according to one embodiment of the present invention. The display 3200 may include a module identification field 3210 that indicates a module identifier assigned to a module. A name field 3220 may be provided that enables the user to assign a name to the module. A serial number field 3230 may be provided that enables the user to assign a serial number to the module. Selectable function keys 3240 may also be presented to enable the user to save module information and exit the display 3200.

Figure 33:
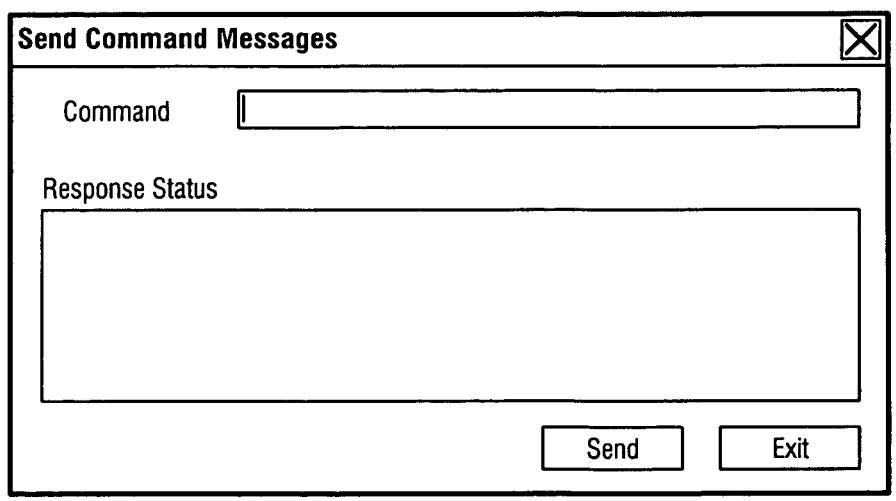
FIG. 33 is a display associated with sending commands in accordance with the present invention.

The user may use a send commands display as shown in FIG. 33 to input specific commands. The user may input a particular command and receive a response status from the automated reagent dispensing system regarding the particular command.

FIG. 34 illustrates a display 3400 that may be presented to a user to select a tray reagent according to one embodiment of the present invention. The display 3400 may include an identifier field 3410 and a name field 3420 that indicates an identifier and a name for a particular tray reagent. One or more selectable function keys 3430 may be used to perform various functions. For example, the user may create, edit or delete a tray reagent using the function keys 3430 or exit the display 3400.

FIGS. 35-36 illustrates displays 3500, 3600 that maybe presented to a user to create and edit a tray reagent, respectively, according to one embodiment of the invention. The displays 3500,3600 may include a plurality of data fields 3510, 3610 that enable the user to input or edit information regarding a particular tray reagent. The data fields 3510, 3610 may include, for example, tray reagent identifier, tray reagent full name, abbreviated name, antibody type, antibody source, clone, dilution, primary pretreatment, incubation time, detection system, hazard level, waste type, stability, price, inventory, minimum stock quantity, and last received date.

Information sections 3520, 3620 maybe provided that provides additional information regarding one or more of the data fields 3510, 3610. Selectable function keys 3530, 3630 may also be presented to enable the user to save a particular tray reagent and exit the displays 3500, 3600. Furthermore, tray reagent category selectors 3540, 3640 may also be provided. The tray reagent category selectors 3540, 3640 enable the user to indicate whether the tray reagent is a basic tray reagent or a user-defined tray reagent.

FIG. 37 illustrates a display 3700 that may be presented to a user to select a cartridge reagent according to one embodiment of the present invention. The display 3700 may include an identifier field 3710 and a name field 3720 that indicates an identifier and a name for a particular cartridge reagent. One or more selectable function keys 3730 maybe used to perform various functions. For example, the user may create, edit or delete a cartridge reagent using the function keys 3730 or exit the display 3700.

FIGS. 38-39 illustrate displays 3800, 3900 that maybe presented to a user to create and edit a cartridge reagent, respectively, according to one embodiment of the invention. The displays 3800, 3900 may include a plurality of data fields 3810, 3910 that enable the user to input or edit information regarding a particular cartridge reagent. The data fields 3810, 3910 may include, for example, cartridge identifier, full name, abbreviated name, reagent type, reagent source, hazard level, waste type, product code, package, stability, on-board stability, price, inventory, minimum stock quantity, and last received date.

Information sections 3820, 3920 maybe provided that provides additional information regarding one or more of the data fields 3810, 3910. Selectable function keys 3830, 3930 may also be presented to enable the user to save a particular cartridge reagent and exit the displays 3800, 3900. Furthermore, cartridge reagent category selectors 3840, 3940 may also be provided. The cartridge reagent category selectors 3840, 3940 enable the user to indicate whether the cartridge reagent is a basic cartridge reagent or a user-defined cartridge reagent.

FIG. 40 illustrates a display 4000 that may be presented to a user to select a bulk solution according to one embodiment of the present invention. The display 4000 may include an identifier field 4010 and a name field 4020 that indicates an identifier and a name for a particular bulk solution. One or more selectable function keys 4030 may be used to perform various functions. For example, the user may create, edit or delete a bulk solution using the function keys 4030 or exit the display 4000.

FIGS. 41-42 illustrate displays 4100, 4200 that may be presented to a user to create and edit a bulk solution, respectively, according to one embodiment of the invention. The displays 4100, 4200 may include a plurality of data fields 4110, 4210 that enable the user to input or edit information regarding a particular bulk solution. The data fields 4110, 4210 may include, for example, solution identifier, full name, abbreviated name, solution type, hazard level, waste type, product code, package size, stability, price, inventory, minimum stock quantity, and last received date.

Information sections 4120, 4220 may be provided that provides additional information regarding one or more of the data fields 4110, 4210. Selectable function keys 4130, 4230 may also be presented to enable the user to save a particular bulk solution and exit the displays 4100, 4200. Furthermore, bulk solution category selectors 4140, 4240 may also be provided. The bulk solution category selectors 4140, 4240 enable the user to indicate whether the bulk solution is a basic bulk solution or a user-defined bulk solution.

FIG. 43 illustrates a display 4300 that may be presented to a user to setup bulk solution bottles according to one embodiment of the present invention. The display 4300 may include a bottle identification field 4310 that indicates an identifier assigned to a bulk solution bottle. A bulk solution identification field 4320 may be provided to enable the user to indicate an identifier of a bulk solution stored in the bulk solution bottle. A bulk solution abbreviated name field 4330 may be provided to enable the user to indicate an abbreviated name for the bulk solution. A source field 4340 may be provided to enable the user to indicate a source for the bulk solution. A capacity field 4350 may be provided to enable the user to indicate a capacity, for example, liters, of the bulk solution bottle. Selectable function keys 4360 may also be presented to enable the user to save bulk solution bottle information and exit the display 4300.

FIG. 44 illustrates a display 4400 that may be presented to a user to setup waste bottles according to one embodiment of the present invention. The display 4400 may include a bottle identification field 4410 that indicates an identifier assigned to a waste bottle. A waste type identification field 4420 may be provided to enable the user to indicate an identifier for a type of waste stored in the waste bottle. A waste type field 4430 maybe provided to enable the user to indicate a type of waste stored in the waste bottle. A location field 4440 may be provided to enable the user to indicate a location of the waste bottle. A capacity field 4450 may be provided to enable the user to indicate a capacity, for example, liters, of the waste bottle. Selectable function keys 4460 may also be presented to enable the user to save bulk solution bottle information and exit the display 4400.

FIG. 45 is an illustration of a display 4500 that may be presented to enable the user to create a worklist according to one embodiment of the present invention. The display 4500 may include a worklist identifier 4510 such as a name that identifies the worklist created. A table 4520 may include sections, rows, columns, etc. providing slide information 4530 and tray information 4540. The slide information 4530 may include, for example, slide identification. The tray information 4540 may include, for example, tray reagent identification, tray reagent abbreviated name, program identification, program abbreviated name, and whether all or a portion of the tray information 4540 has changed. Other types of slide information 4530 and tray information 4540 may also be provided.

The display 4500 may also include selectable function keys 4550 that perform a desired function when selected. The keys 4550 may enable users to display slide details, adjust program variables, delete entry, print worklist, and close worklist. The keys 4550 may be used in conjunction with information provided in the table 4520. For example, the user may select information related to a particular slide. This selection may be indicated by having a row in which the information lies be highlighted. The user may then select one of the keys 4550 to perform a particular function related to the information selected. For example, the user may select information regarding a particular slide and choose to delete information regarding that slide. The user then selects delete entry key 4550 to delete the information regarding that slide. Optionally, the user may be presented with a confirmation message requesting confirmation from the user that the information selected is to be deleted.

Figure 46:
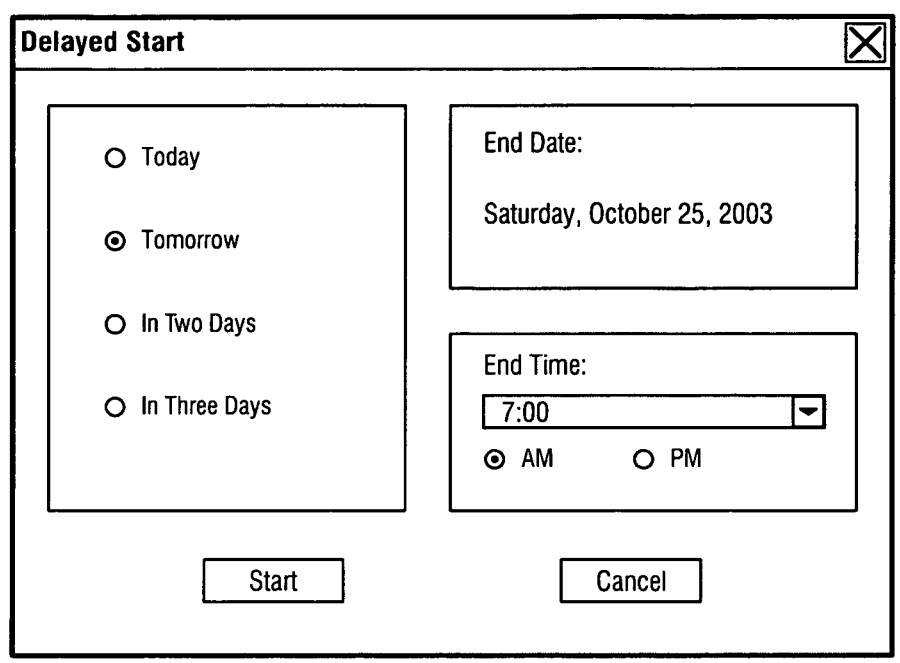
FIG. 46 is a display associated with a delayed start in accordance with the present invention.

The user may also elect to begin a particular program at a later time. The user may use a delayed start function to achieve this. If the user desires to begin a particular program at a later time, the user may be presented with a delayed start display as shown in FIG. 46. The user may elect to run a program later the same day, the following day, in two (2) days, in three (3) days, etc.

Figure 47:
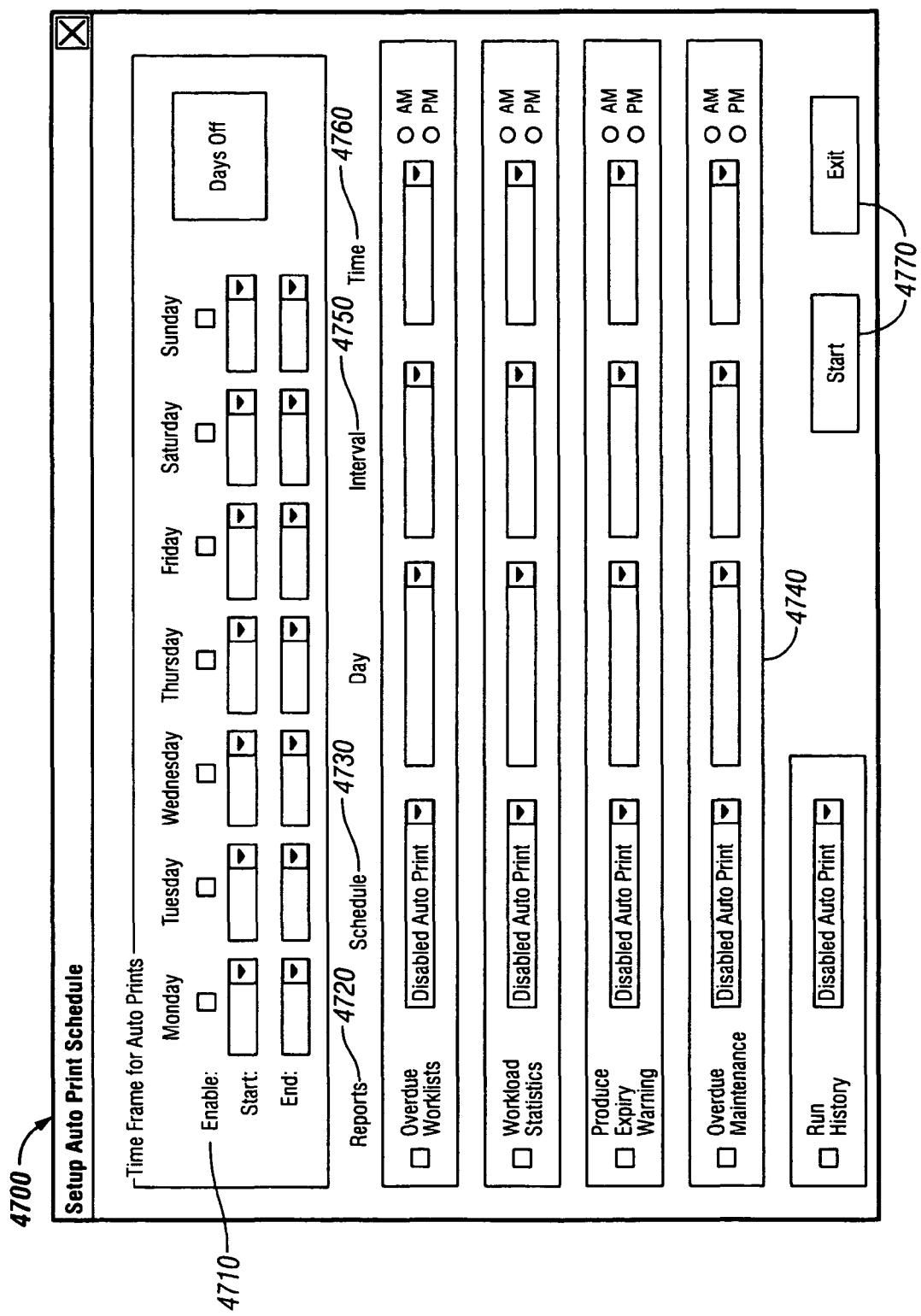
FIG. 47 is a display associated with setting up an auto print schedule in accordance with the present invention.

FIG. 47 illustrates a display 4700 that may be presented to a user to setup an auto print schedule according to one embodiment of the present invention. The display 4700 may include a time frame for auto prints section 4710. The time frame for auto prints section 4710 may enable the user to select a day of the week, start times, end times, and days off. The user may select one or more days of the week to automatically print a schedule by, for example, selecting a check box adjacent a named day of the week. The user may also select start and ends times by, for example, selecting a time listed in a pull-down menu.

The display 4700 may also include reports fields 4720, schedule fields 4730, days fields 4740, interval fields 4750, and time fields 4760. The report fields 4720 may provide a list of reports for which to automatically schedule to print a particular report. For example, the user may select to automatically print reports for overdue worklists, workload statistics, product expiry warning, overdue maintenance, run history, and other reports. The schedule fields section 4730 may provide pull-down menus, radio buttons, check boxes or other selectable option to disable or enable scheduled auto prints for a particular report. The day fields 4740, interval fields 4750, and time fields 4760 may also enable the user to select a day, interval, and time on which to automatically print a particular report. Selectable function keys 4770 may also be presented to enable the user to save an auto print schedule and exit the display 4700.

Figure 48:
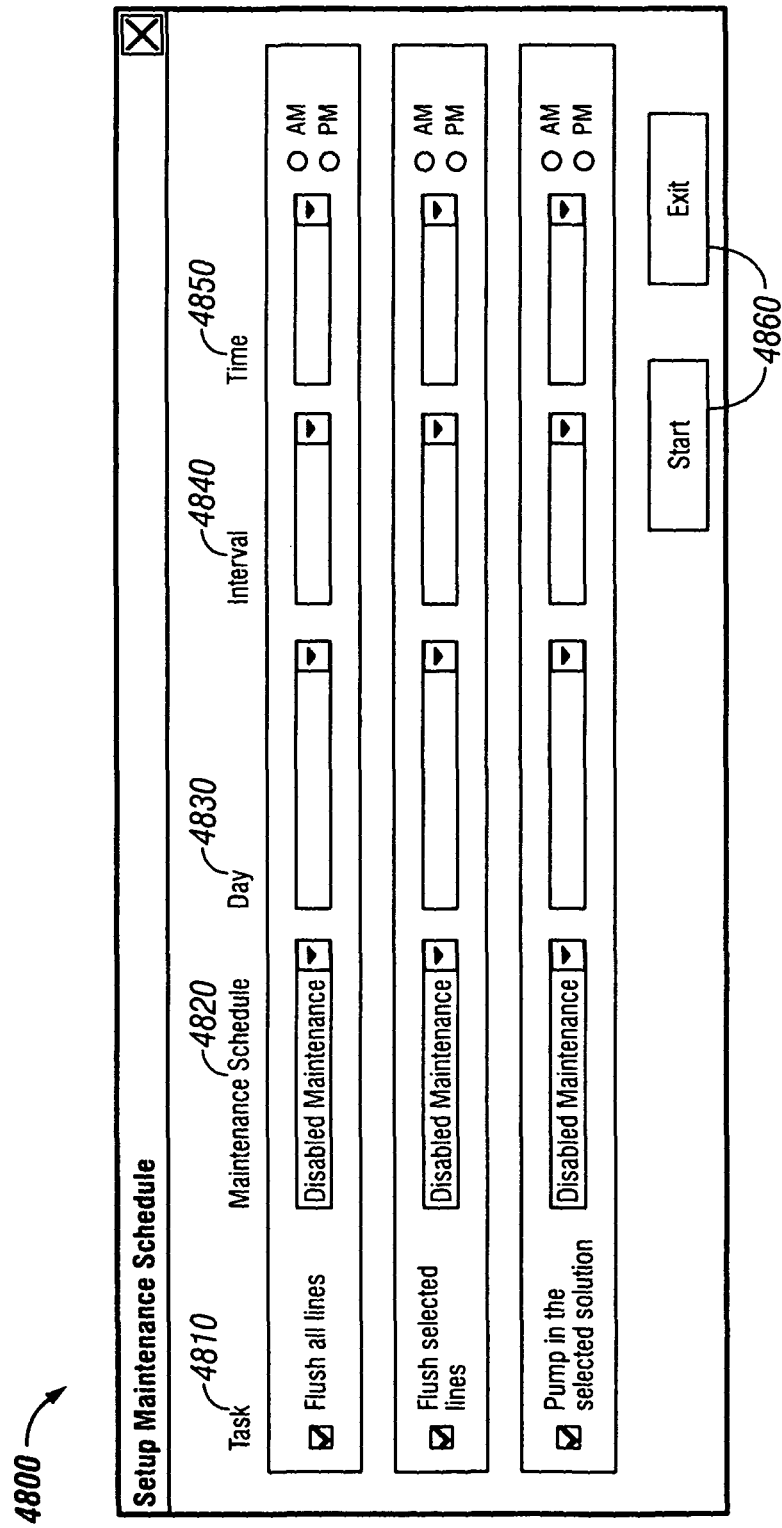
FIG. 48 is a display associated with scheduled maintenance setup in accordance with the present invention.

FIG. 48 illustrates a display 4800 that may be presented to a user to setup maintenance schedules according to one embodiment of the present invention. The display 4800 may include task fields 4810 that enable the user to select one or more tasks for which to setup a maintenance schedule. The tasks may include, for example, flush all lines, flush selected lines, pump in selected solution, etc. A maintenance schedule field 4820 may be provided to enable or disable a maintenance schedule for a particular task. A day field 4830 may be provided to enable the user to select a day of the week on which to perform the task. An interval field 4840 may be provided to enable the user to indicate an interval at which to perform the task. A time field 4850 may be provided to indicate a time at which to perform the task. Selectable function keys 4860 may also be presented to enable the user to save the maintenance schedule and exit the display 4800.

Figure 49:
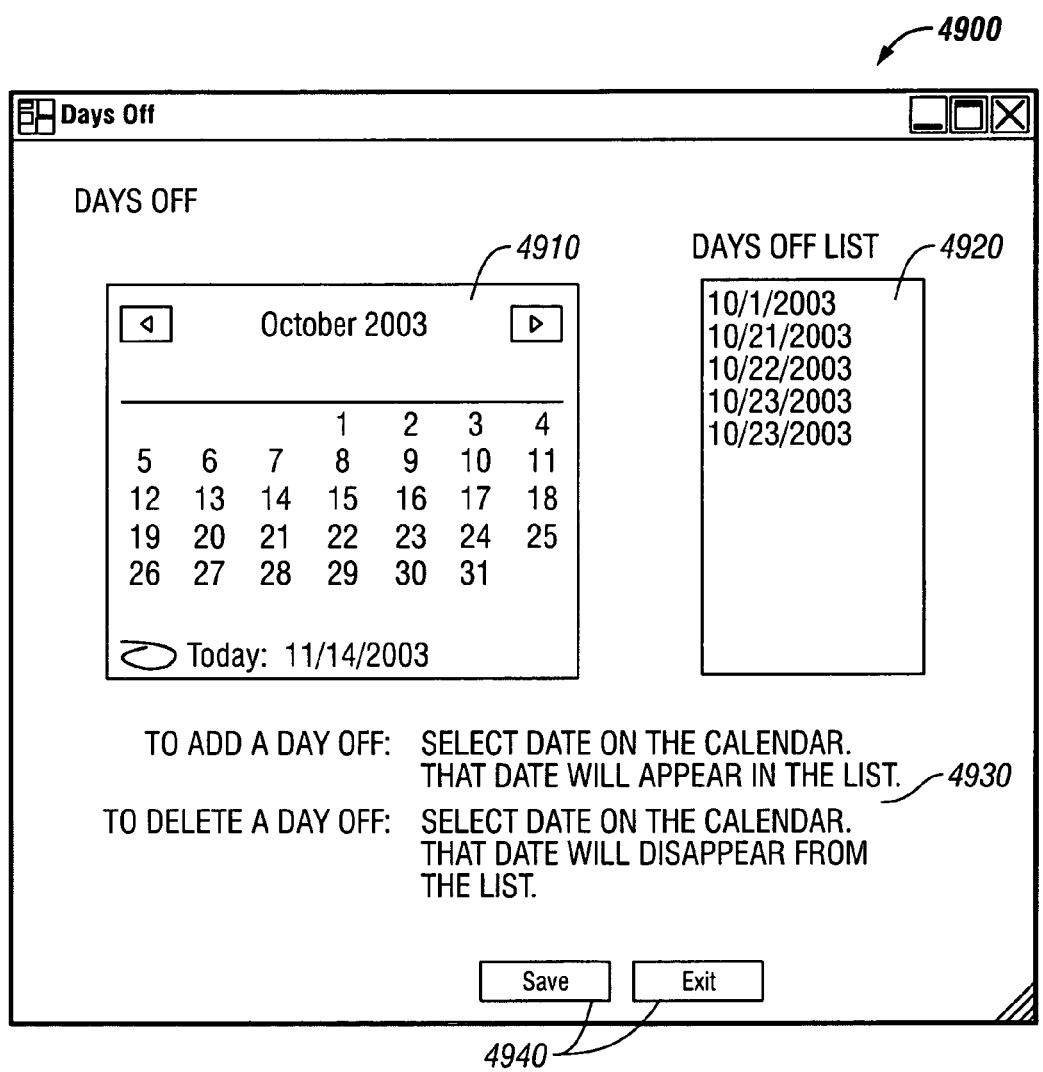
FIG. 49 is a display associated with setting up days off in accordance with the present invention.

FIG. 49 illustrates a display 4900 that may be presented to a user to enable selecting auto print schedule days off according to one embodiment of the present invention. The display 4900 may include a calendar view 4910 that enables the user to select a particular day on the calendar to designate as a day off. The days off selected by the user may be presented in a days off list 4920. Instructions 4930 regarding how to add and delete a day off may also be presented in the display 4900. Selectable function keys 4940 may also be presented to enable the user to save a days off list and exit the display 4900.

Figure 50:
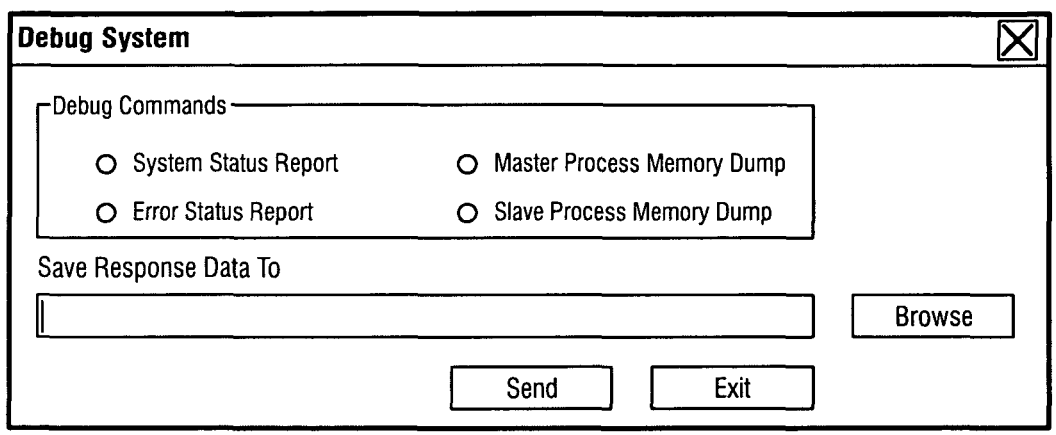
FIG. 50 is a display associated with debugging the system in accordance with the present invention.

The user may also request that debug commands be run and that response data be saved to a particular location. The user may request the debug commands be run using a debug system display as shown in FIG. 50. Debug commands may include, for example, system status report, error status report, master process memory dump, slave process memory dump, etc.

Figure 52:
FIG. 52 is a display associated with viewing waste bottle information in accordance with the present invention.

Referring to FIGS. 51-52, screens showing status of bulk solution bottles and waste bottles may be displayed. The screens generally indicate information about the bottles such as bottle identification. They may also indicate the type of solution or waste, as appropriate. Additionally, they may provide information regarding the capacity, for example in graphical form.

Figure 53:
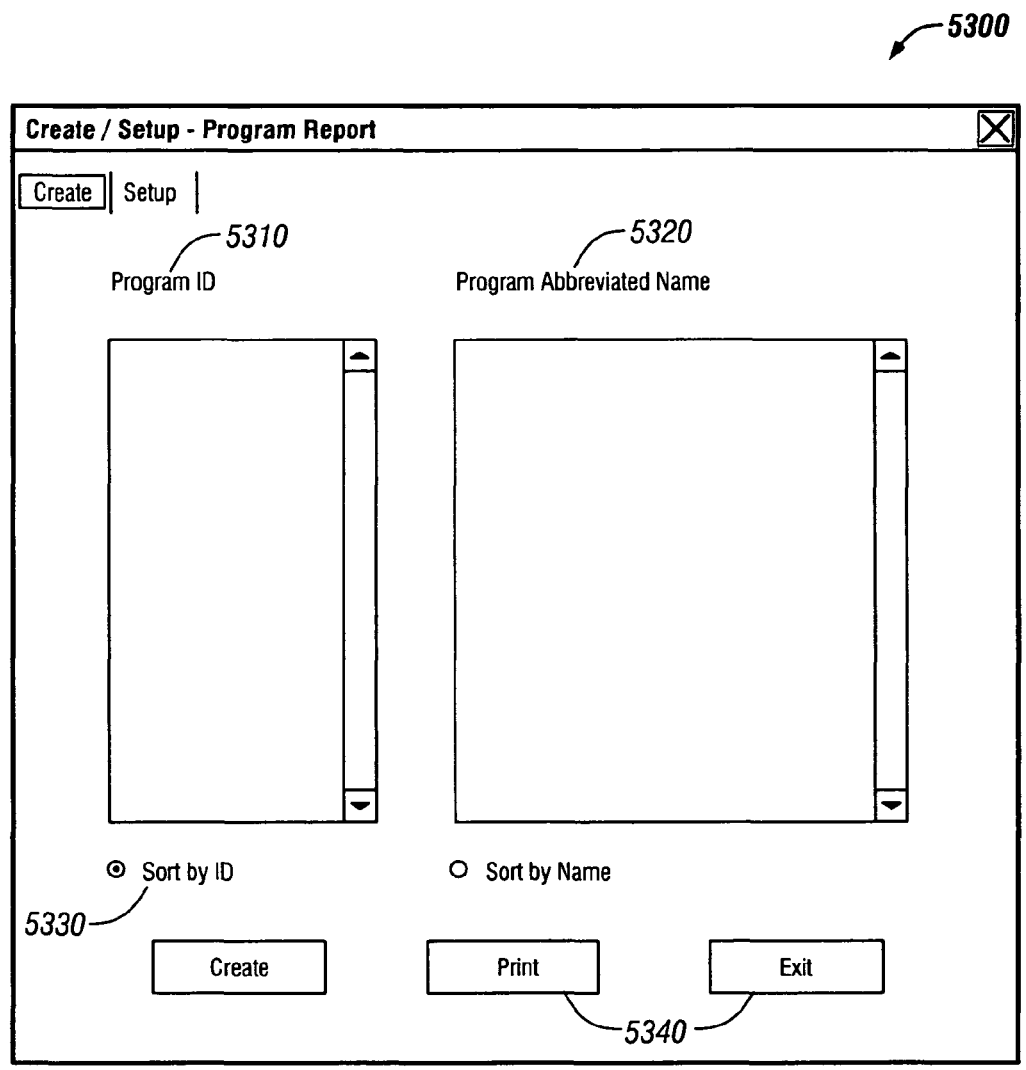
FIG. 53 is a display associated with creating a program report in accordance with the present invention.

FIG. 53 illustrates a display 5300 that may be presented to a user to create a program report according to one embodiment of the present invention. The display 5300 may include a program identifier section 5310 and a program abbreviated name section 5320. The program identifier section 5310 and program abbreviated name section 5320 may provide lists of program identifiers and abbreviated names, respectively, for which the user may create or print a program report. The lists of program identifiers and abbreviated names may be sorted by identifier and name, respectively, using sort options 5330. Selectable function keys 5340 may also be presented to enable the user to create or print one or more program reports and exit the display 5300.

Figure 54:
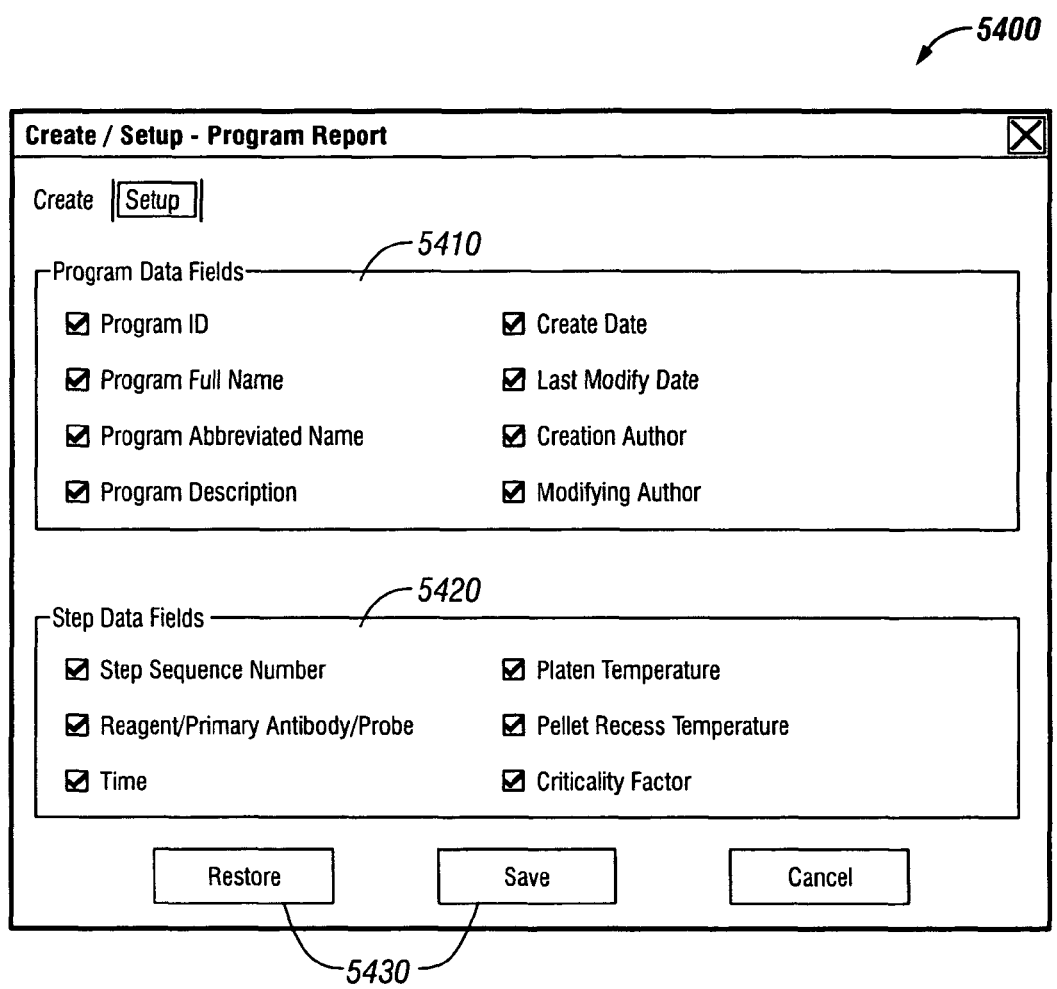
FIG. 54 is a display associated with setting up a program report in accordance with the present invention.

FIG. 54 illustrates a display 5400 that may be presented to a user to setup a program report according to one embodiment of the present invention. The display 5400 may be used to customize information provided in program reports created by the user. The display 5400 may include a program data fields section 5410 that includes one or more data fields that the user may select to customize a program report. For example, the program data fields section 5410 may include selectable options that enable the user to select particular information to be included in the report. The information may include, for example, program identifier, program full name, program abbreviated name, program description, creation date, last modify date, creation author, and modifying author.

The display 5400 may also include a step data fields section 5420 that includes one or more fields regarding step data that may be included in the report. The step data may include, for example, step sequence number, reagent/primary antibody/probe, time, platen temperature, pellet recess temperature, and criticality factor. Selectable function keys 5430 may also be presented to enable the user to restore or save a program report setup and exit the display 5400.

Figure 55:
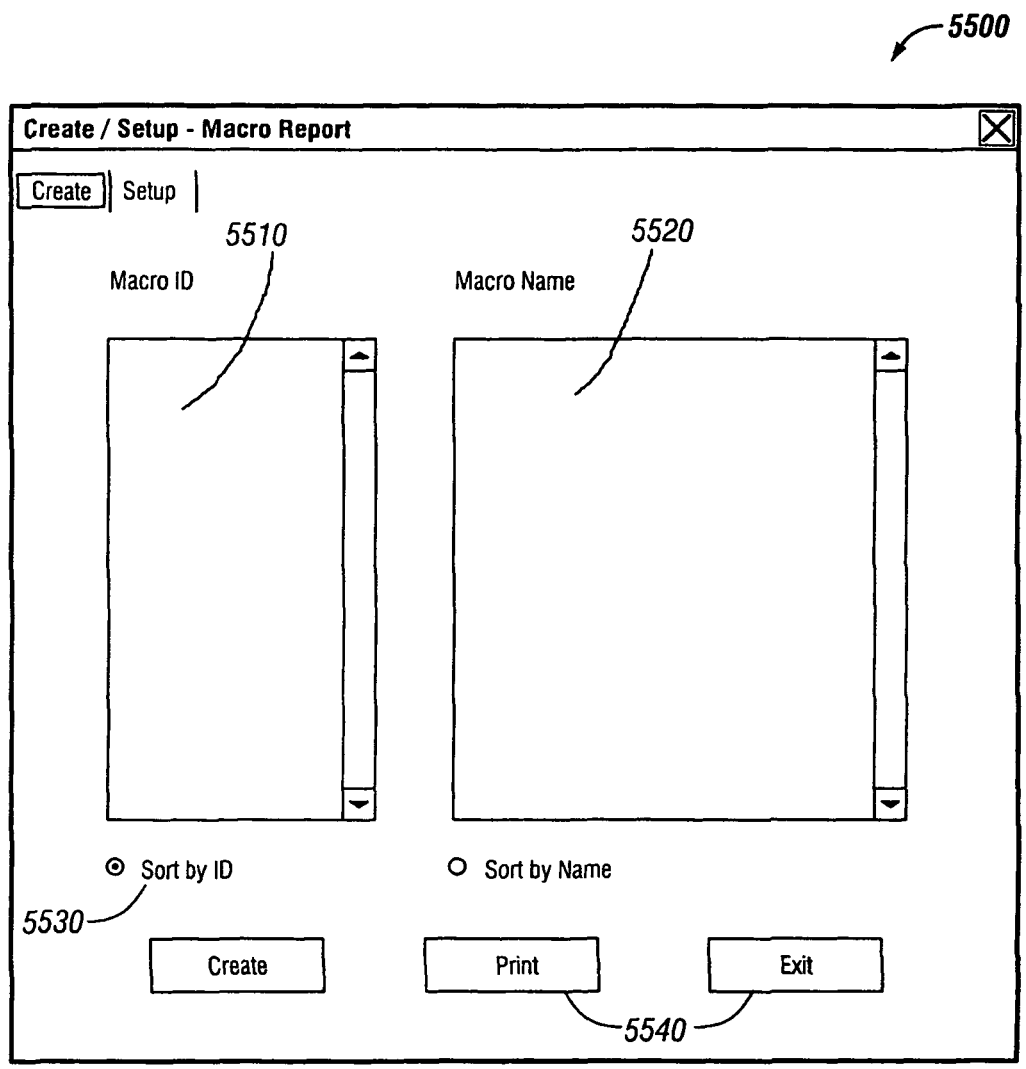
FIG. 55 is a display associated with creating a macro report in accordance with the present invention.

FIG. 55 illustrates a display 5500 that may be presented to a user to create a macro report according to one embodiment of the present invention. The display 5500 may include a macro identifier section 5510 and a macro name section 5520. The macro identifier section 5510 and macro name section 5520 may provide a list of macro identifiers and names, respectively, for which the user may create or print a macro report. The lists of macro identifiers and names may be sorted by identifier and name, respectively, using sort options 5530. Selectable function keys 5540 may also be presented to enable the user to create or print one or more macro reports and exit the display 5500.

Figure 56:
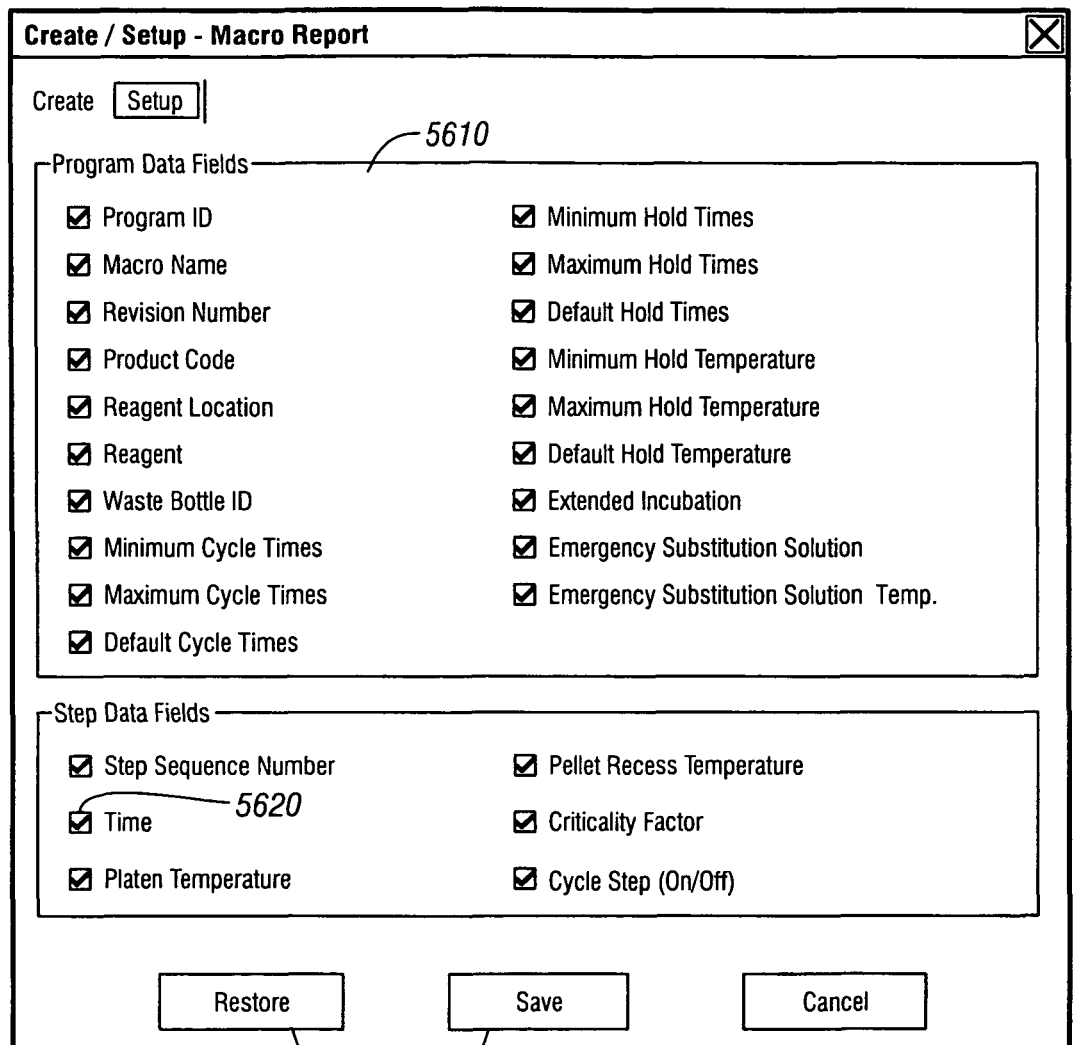
FIG. 56 is a display associated with setting up a macro report in accordance with the present invention.

FIG. 56 illustrates a display 5600 that may be presented to a user to setup a macro report according to one embodiment of the present invention. The display 5600 may be used to customize information provided in macro reports created by the user. The display 5600 may include a macro data fields section 5610 that includes one or more data fields that the user may select to customize a macro report. For example, the macro data fields section 5610 may include selectable options that enable the user to select particular information to be included in the report. The information may include, for example, macro identifier, macro name, revision number, product code, reagent location, reagent, waste bottle identifier, minimum cycle times, maximum cycle times, default cycle times, minimum hold times, maximum hold times, default hold times, minimum hold temperature, maximum hold temperature, default hold temperature, extended incubation, emergency substitution solution, and emergency substitution solution temperature.

The display 5600 may also include a step data fields section 5620 that includes one or more fields regarding step data that may be included in the report. The step data may include, for example, step sequence number, time, platen temperature, pellet recess temperature, criticality factor, and cycle step (on/off). Selectable function keys 5630 may also be presented to enable the user to restore or save a macro report setup and exit the display 5600.

Figure 57:
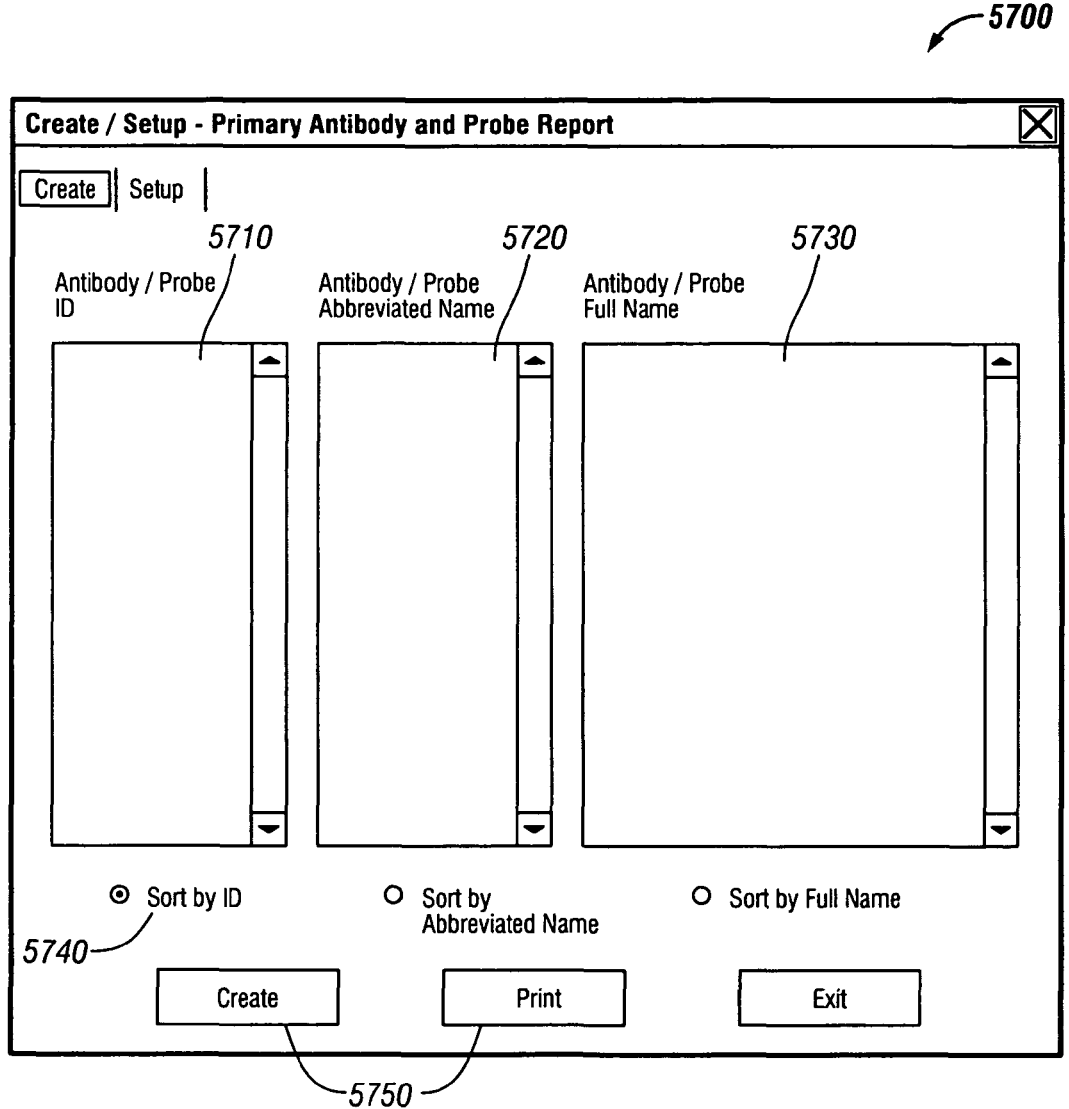
FIG. 57 is a display associated with creating a primary antibody/probe report in accordance with the present invention.

FIG. 57 illustrates a display 5700 that may be presented to a user to create a primary antibody and probe report according to one embodiment of the present invention. The display 5700 may include an antibody/probe identifier section 5710, an antibody/probe abbreviated name section 5720, and an antibody/probe full name section 5730. The antibody/probe identifier section 5710, antibody/probe abbreviated name section 5720, and antibody/probe full name section 5730 may provide lists of antibody/probe identifiers, abbreviated names, and full names, respectively, for which the user may create or print a primary antibody/probe report. The lists of antibody/probe identifiers, abbreviated names, and full names may be sorted by identifier, abbreviated name, and full name, respectively, using sort options 5740. Selectable function keys 5750 may also be presented to enable the user to create or print one or more primary antibody/probe reports and exit the display 5700.

Figure 58:
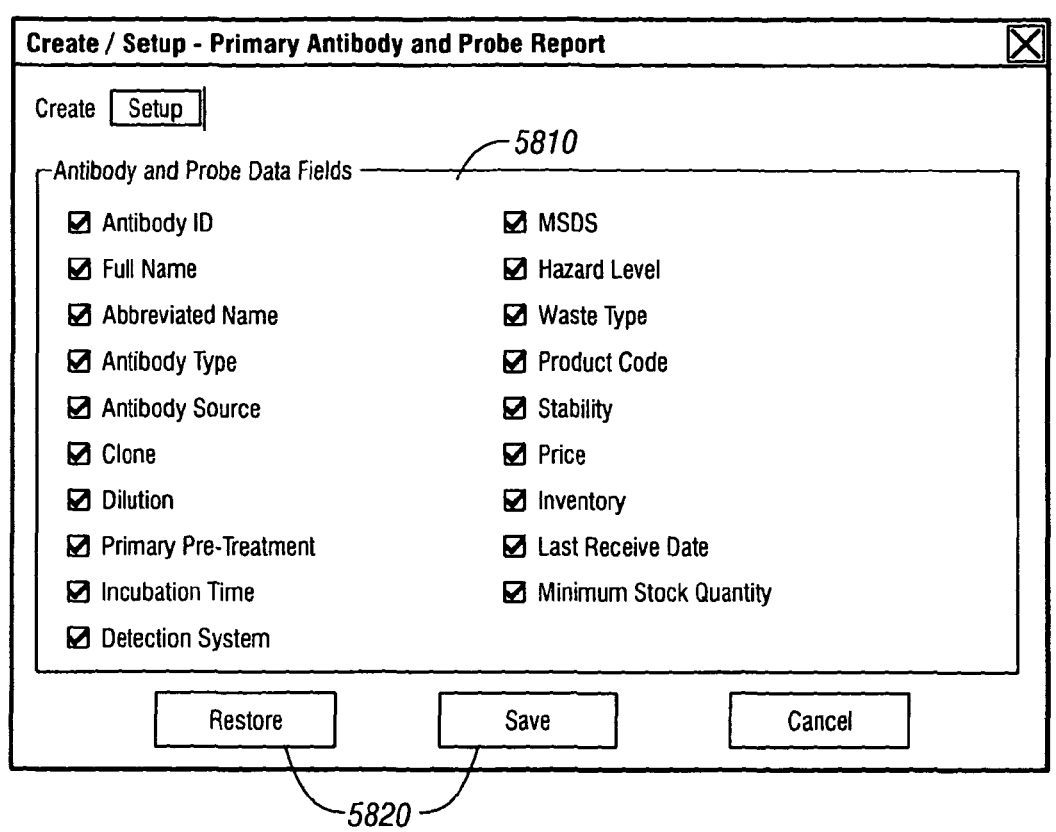
FIG. 58 is a display associated with setting up a primary antibody/probe report in accordance with the present invention.

FIG. 58 illustrates a display 5800 that may be presented to a user to setup a primary antibody/probe report according to one embodiment of the present invention. The display 5800 may be used to customize information provided in primary antibody/probe reports created by the user. The display 5800 may include an antibody and probe data fields section 5810 that includes one or more data fields that the user may select to customize a primary antibody/probe report. For example, the antibody/probe data fields section 5810 may include selectable options that enable the user to select particular information to be included in the report. The information may include, for example, antibody identifier, full name, abbreviated name, antibody type, antibody source, clone, dilution, primary pre-treatment, incubation time, detective system, MSDS, hazard level, waste type, product code, stability, price, inventory, last receive date, and minimum stock quantity. Selectable function keys 5820 may also be presented to enable the user to restore or save a primary antibody and probe report setup and exit the display 5800.

Figure 59:
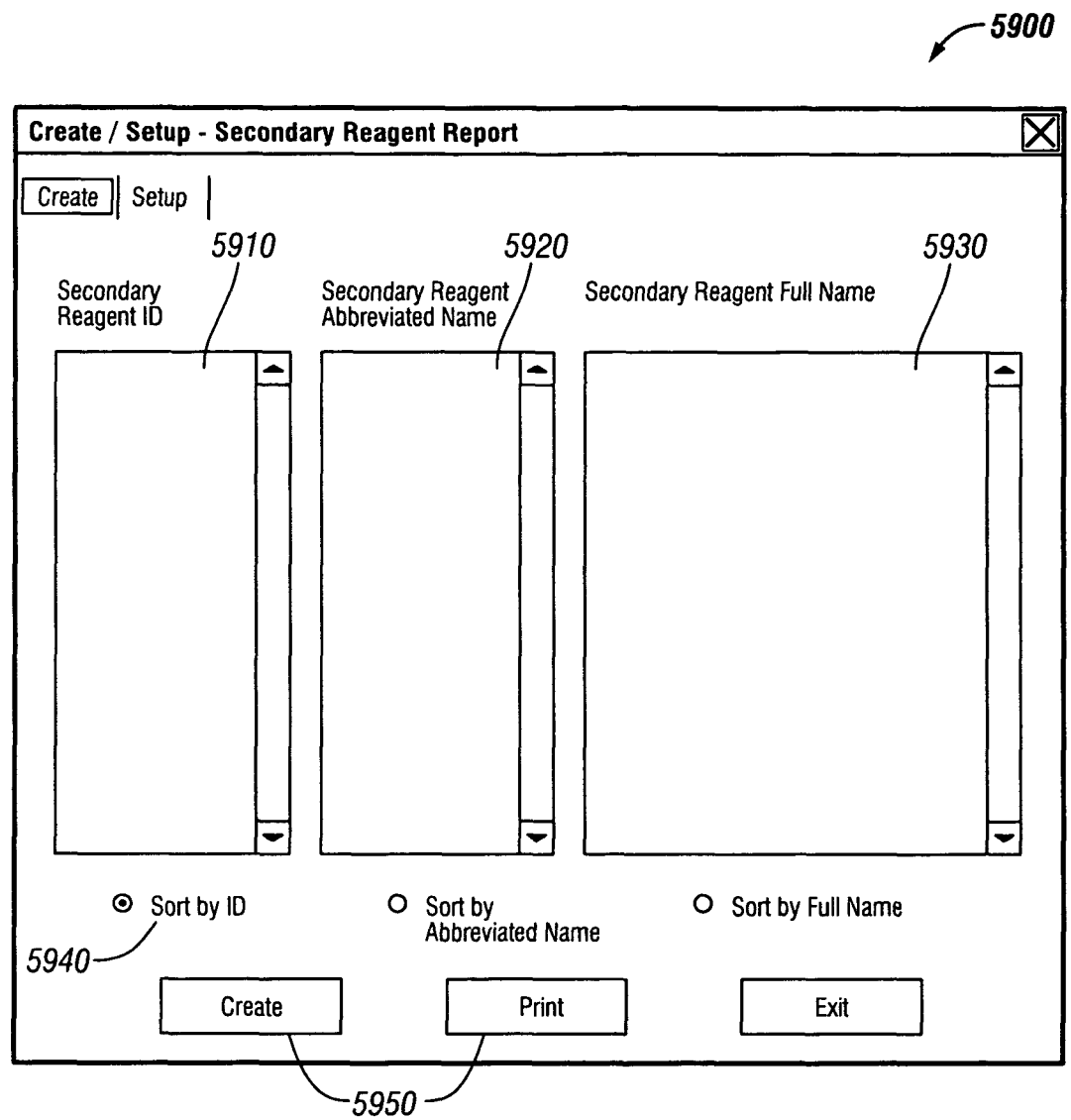
FIG. 59 is a display associated with creating a secondary reagent report in accordance with the present invention.

FIG. 59 illustrates a display 5900 that may be presented to a user to create a secondary reagent report according to one embodiment of the present invention. The display 5900 may include a secondary reagent identifier section 5910, a secondary reagent abbreviated name section 5920, and a secondary reagent full name section 5930. The secondary reagent identifier section 5910, secondary reagent abbreviated name section 5920, and secondary reagent full name section 5930 may provide lists of secondary reagent identifiers, abbreviated names, and full names, respectively, for which the user may create or print a secondary reagent report. The lists of secondary reagent identifiers, abbreviated names, and full names may be sorted by identifier, abbreviated name, and full name, respectively, using sort options 5940. Selectable function keys 5950 may also be presented to enable the user to create or print one or more secondary reagent reports and exit the display 5900.

Figure 60:
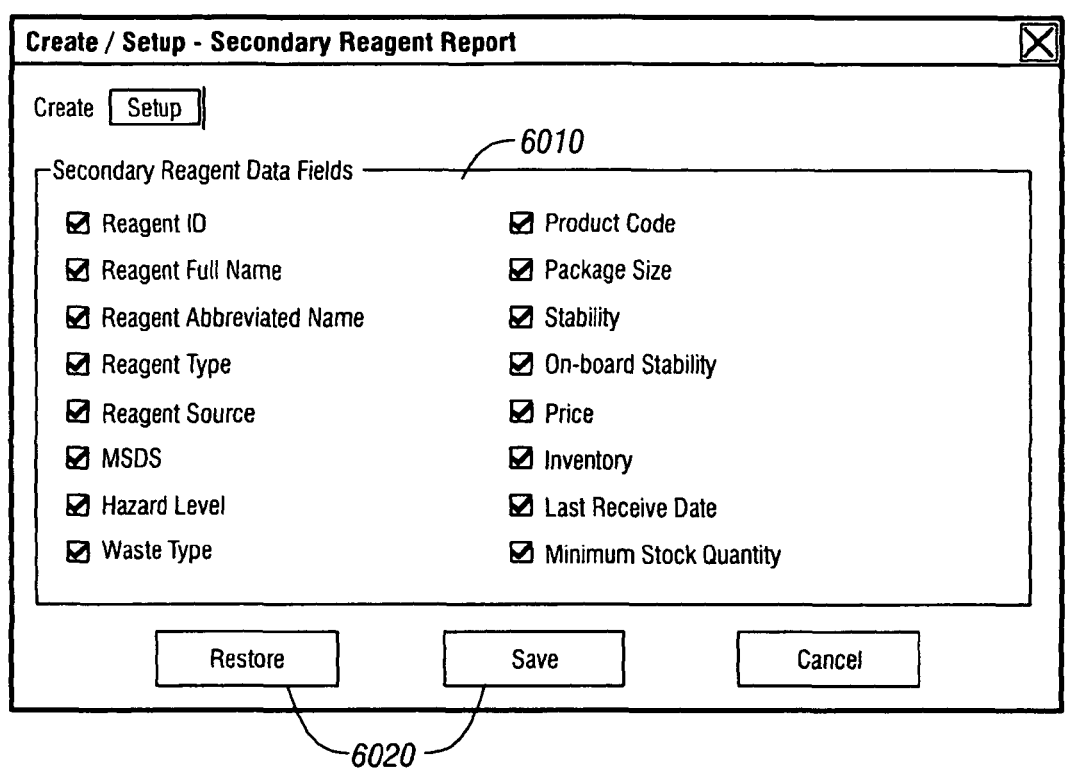
FIG. 60 is a display associated with setting up a secondary reagent report in accordance with the present invention.

FIG. 60 illustrates a display 6000 that may be presented to a user to setup a secondary reagent report according to one embodiment of the present invention. The display 6000 may be used to customize information provided in secondary reagent reports created by the user. The display 6000 may include a secondary reagent data fields section 6010 that includes one or more data fields that the user may select to customize a secondary reagent report. For example, the secondary reagent data fields section 6010 may include selectable options that enable the user to select particular information to be included in the report. The information may include, for example, reagent identifier, reagent full name, reagent abbreviated name, reagent type, reagent source, MSDS, hazard level, waste type, product code, package size, stability, on-board stability, price, inventory, last receive date, and minimum stock quantity. Selectable function keys 6020 may also be presented to enable the user to restore or save a secondary reagent report setup and exit the display 6000.

Figure 61:
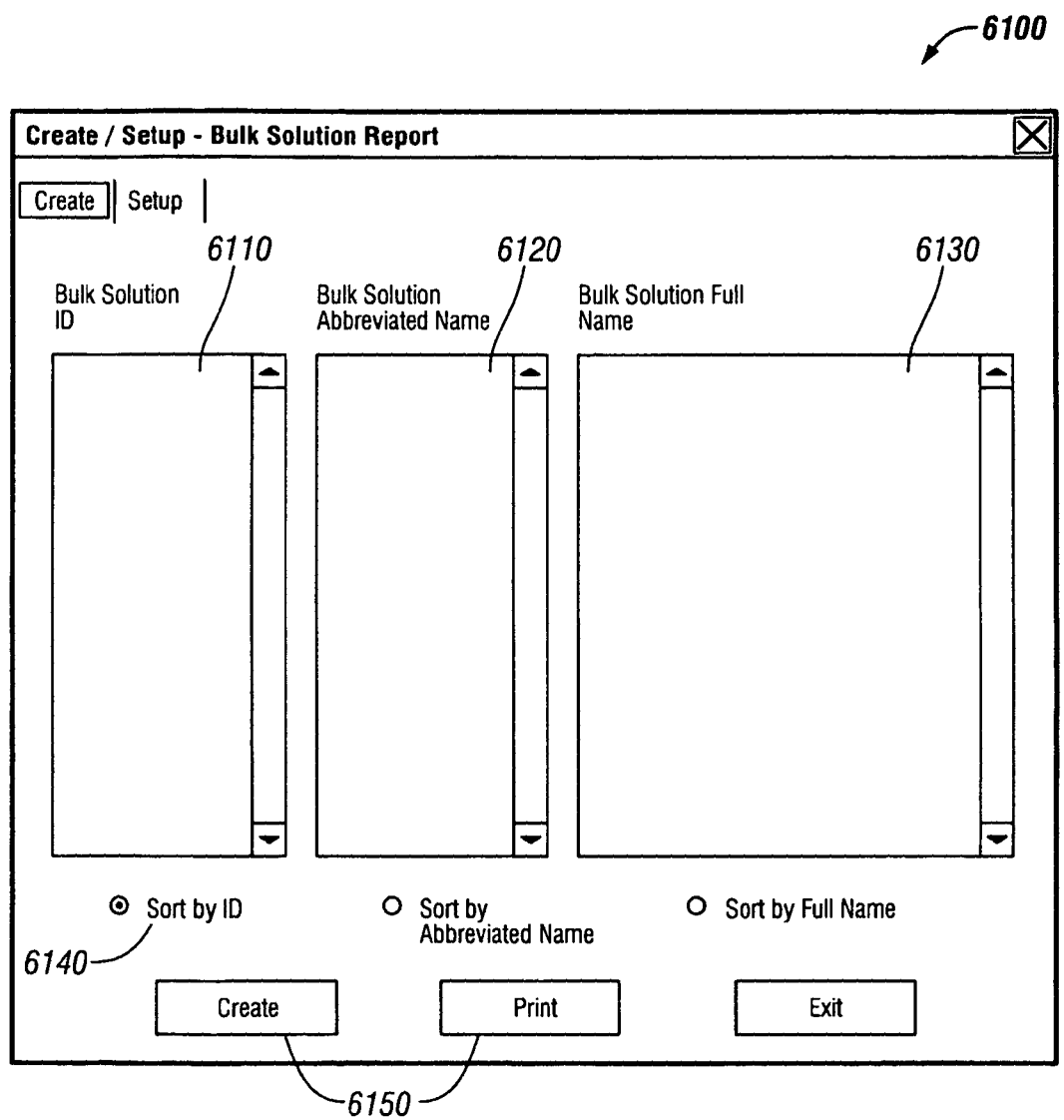
FIG. 61 is a display associated with creating a bulk solution report in accordance with the present invention.

FIG. 61 illustrates a display 6100 that may be presented to a user to create a bulk solution report according to one embodiment of the present invention. The display 6100 may include a bulk solution identifier section 6110, a bulk solution abbreviated name section 6120, and a bulk solution full name section 6130. The bulk solution identifier section 6110, bulk solution abbreviated name section 6120, and bulk solution full name section 6130 may provide lists of bulk solution identifiers, abbreviated names, and full names, respectively, for which the user may create or print a bulk solution report. The lists of bulk solution identifiers, abbreviated names, and full names may be sorted by identifier, abbreviated name, and full name, respectively, using sort options 6140. Selectable function keys 6150 may also be presented to enable the user to create or print one or more bulk solution reports and exit the display 6100.

Figure 62:
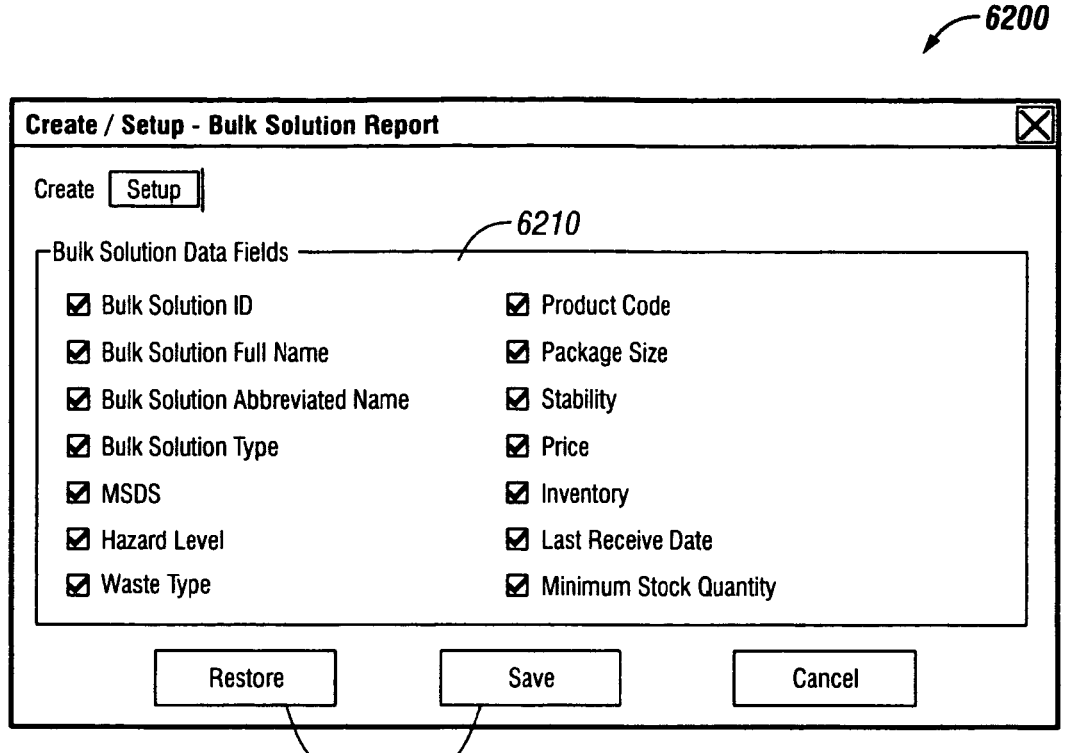
FIG. 62 is a display associated with setting up a bulk solution report in accordance with the present invention.

FIG. 62 illustrates a display 6200 that may be presented to a user to setup a bulk solution report according to one embodiment of the present invention. The display 6200 may be used to customize information provided in bulk solution reports created by the user. The display 6200 may include a bulk solution data fields section 6210 that includes one or more data fields that the user may select to customize a bulk solution report. For example, the bulk solution data fields section 6210 may include selectable options that enable the user to select particular information to be included in the report. The information may include, for example, bulk solution identifier, bulk solution full name, bulk solution abbreviated name, bulk solution type, MSDS, hazard level, waste type, product code, package size, stability, price, inventory, last receive date, and minimum stock quantity.

Selectable function keys 6220 may also be presented to enable the user to restore or save a bulk solution report setup and exit the display 6200.

Figure 63:
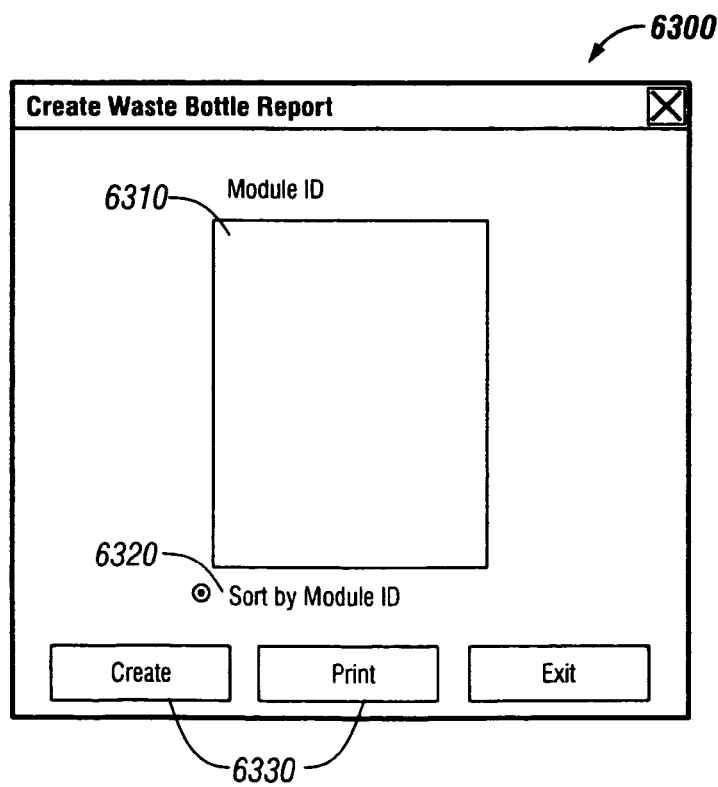
FIG. 63 is a display associated with creating a waste bottle report in accordance with the present invention.
Figure 64:
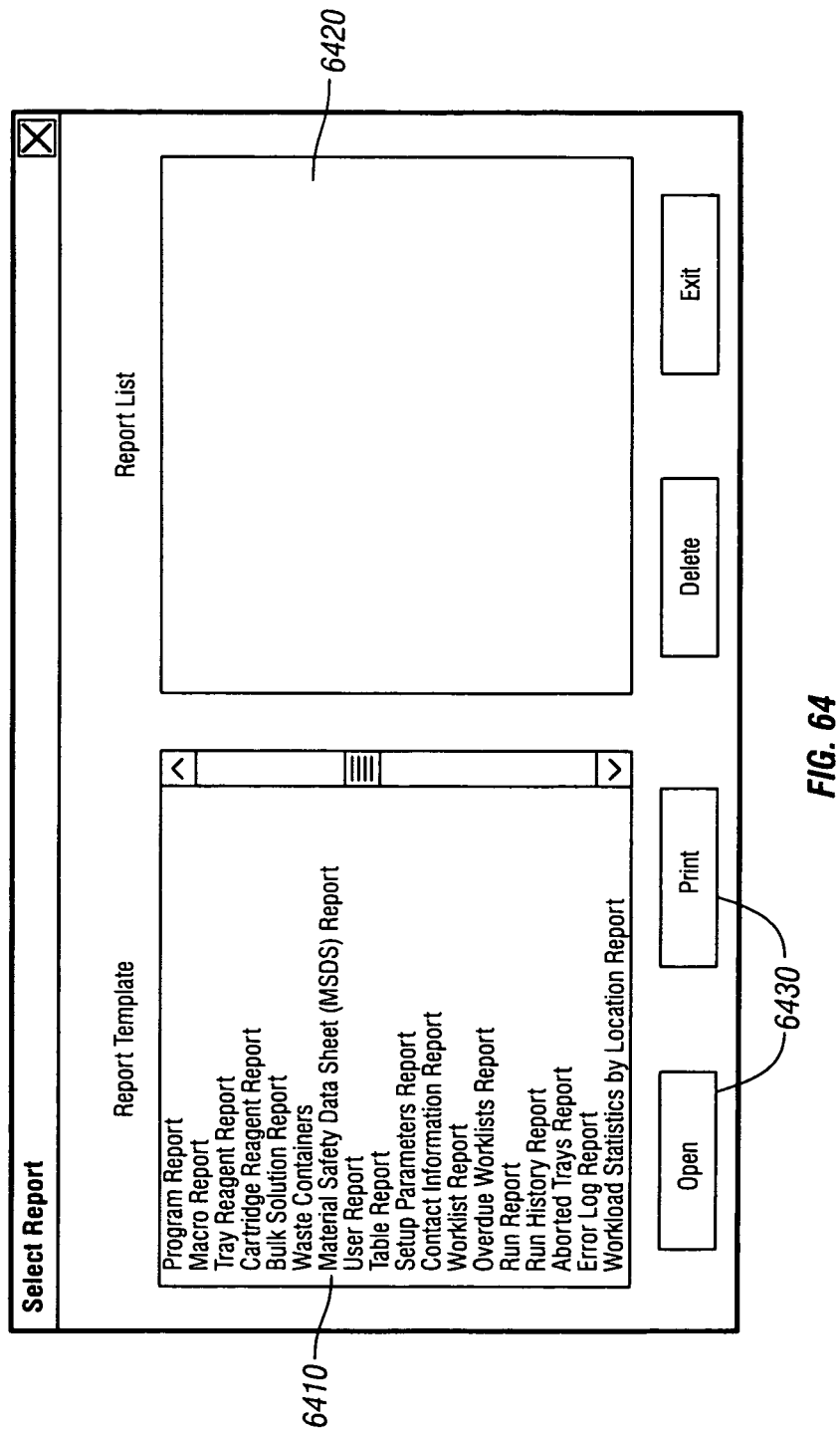
FIG. 64 is a display associated with viewing reports in accordance with the present invention.

FIG. 63 illustrates a display 6300 that may be presented to a user to create a waste bottle report according to one embodiment of the present invention. The display 6300 may include a module identifier section 6310. The module identifier section 6310 may provide a list of module identifiers for which the user may create or print a module report. The list of module identifiers may be sorted by identifier using sort option 6320. Selectable function keys 6330 may also be presented to enable the user to create or print one or more module reports and exit the display 6300.

Finally, the user may be presented with a screen that allows them to manually print any of the reports described above, as indicated in FIG. 64. The screen provides the user with a list of reports 6410 that the user may select to create. A list of the reports selected by the user is also presented (6420). Finally, function keys 6430 maybe provided that allow the user to open a particular report, print a report, delete a report or exit the screen.

Thus, it is seen that an automated reagent dispensing system and method is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. A method of dispensing reagent, comprising:
   determining an inventory of an automated reagent dispensing system comprising a plurality of stainers, the determining an inventory comprising retrieving information from an identifier on at least one slide retaining tray for retaining a slide in the automated reagent dispensing system, the information identifying a reagent contained in the tray;
   downloading, by the automated reagent dispensing system, a processing program from a central controller, the processing program comprising steps for performing an automated staining procedure;
   determining, by the automated reagent dispensing system, a reagent staining protocol for reagents based on the identified reagent;
   transmitting the determined reagent staining protocol to a manifold controller of the automated reagent dispensing system;
   operating, by the manifold controller, the automated reagent dispensing system to perform the determined reagent staining protocol based on the processing program and independently of the central controller and independent of additional communication with the central controller during performance of the reagent staining protocol, wherein the reagent staining protocol comprises a staining process to dispense one or more reagents to a sample in the at least one slide retaining tray; and
   dispensing at least one of the reagents from a reagent container into the at least one slide retaining tray according to the reagent staining protocol.

2. The method of claim 1 further wherein determining an inventory further comprises scanning an identifier included on at least one of a reagent container and a waste container that are used in the automated reagent dispensing system.

3. The method of claim 1 further comprising generating a status report corresponding to a status of the automated reagent dispensing system, wherein the automated reagent dispensing system generates the status report.

4. The method of claim 1, further comprising:
   determining a reagent container fluid level; and
   outputting a reagent container condition signal, wherein the reagent container condition signal indicates an amount of reagent in the reagent container.

5. The method of claim 1 further comprising:
   receiving an interrupt signal;
   determining whether a hazardous condition exists; and
   stopping processing of the processing program upon detection of the hazardous condition.

6. The method of claim 1 further comprising:
   activating at least one evacuation port of the slide retaining tray.

7. The method of claim 1 further comprising creating an audit log, wherein creating is performed by the automated reagent dispensing system, wherein the audit log stores information related to the slide retaining tray.

8. The method of claim 1, wherein the automated reagent dispensing system comprises tools for a user to create the processing program, the method further comprising providing the tools for a user, wherein the user creates the processing program with the tools.

9. The method of claim 1, wherein the automated reagent dispensing system comprises tools for a user to modify the processing program, the method further comprising providing the tools for a user, wherein the user modifies the processing program with the tools.

10. The method of claim 5, wherein the hazardous condition includes at least that a reagent having a poisonous gas associated therewith has been dispensed.

11. The method of claim 6, wherein waste evacuated through the activated at least one evacuation port is divided into hazardous and non-hazardous waste with each going into a respective waste container.

12. A method of dispensing reagent, comprising:
    determining an inventory of an automated reagent dispensing system comprising a plurality of stainers, the determining an inventory comprising retrieving information from an identifier on at least one slide retaining tray for retaining a slide in the automated reagent dispensing system by the automated reagent dispensing system, the information identifying a reagent contained in the tray;
    downloading, by the automated reagent dispensing system, a processing program from a central controller, the processing program comprising steps for performing an automated staining procedure;
    determining, by the automated reagent dispensing system, a reagent staining protocol for reagents based on the identified reagent; and
    transmitting the reagent staining protocol to a manifold controller of the automated reagent dispensing system;
    operating, by the manifold controller, the automated reagent dispensing system based on the processing program to perform the reagent staining protocol and independently of the central controller and independent of additional communication with the central controller during performance of the reagent staining protocol, wherein the reagent staining protocol comprises a staining process to dispense one or more reagents to a sample in the at least one slide retaining tray, the operating comprising:

dispensing at least one of the reagents from a reagent container into the at least one slide retaining tray according to the reagent staining protocol.

13. The method of claim 12 further wherein determining an inventory further comprises scanning an identifier included on at least one of a reagent container and a waste container that are used in the automated reagent dispensing system.

14. The method of claim 12 further comprising generating a status report corresponding to a status of the automated reagent dispensing system, wherein the automated reagent dispensing system generates the status report.

15. The method of claim 12, further comprising:
   determining a reagent container fluid level; and
   outputting a reagent container condition signal, wherein the reagent container condition signal indicates an amount of reagent in the reagent container.

16. The method of claim 12 further comprising:
   receiving an interrupt signal;
   determining whether a hazardous condition exists; and
   stopping processing of the processing program upon detection of the hazardous condition.

17. The method of claim 12 further comprising:
   activating at least one evacuation port of the slide retaining tray.

18. The method of claim 12 further comprising creating an audit log, wherein creating is performed by the automated reagent dispensing system, wherein the audit log stores information related to the slide retaining tray.

19. The method of claim 12, wherein the automated reagent dispensing system comprises tools for a user to create the processing program, the method further comprising providing the tools for a user, wherein the user creates the processing program with the tools.

20. The method of claim 12, wherein the automated reagent dispensing system comprises tools for a user to modify the processing program, the method further comprising providing the tools for a user, wherein the user modifies the processing program with the tools.

* * * * *